(12) United States Patent
Bolli et al.

(10) Patent No.: US 7,750,040 B2
(45) Date of Patent: Jul. 6, 2010

(54) THIOPHENE DERIVATIVES

(76) Inventors: Martin Bolli, Bachgrabenweg 21, Allschwil (CH) CH-4123; Daniel Bur, Im Rosengarten 24, Therwil (CH) CH-4106; Martine Clozel, Winterhalde 3b, Binningen (CH) CH-4102; Walter Fischli, Obertorweg 64, Allschwil (CH) CH-4123; David Lehmann, Turnerstrasse 9, Basel (CH) CH-4058; Boris Mathys, Baumgartenstrasse 3, Egerkingen (CH) CH-4622; Claus Mueller, Wittlinger Strasse 37, Weil am Rhein (DE) D-79576; Oliver Nayler, Hangstrasse 38, Arlesheim (CH) CH-4144; Michael Scherz, Eigenweg 11, Ettingen (CH) CH-4107; Thomas Weller, Hoelzlistrasse 58, Binningen (CH) CH-4102

( * ) Notice: Subject to any disclaimer, the term of this patent is extended or adjusted under 35 U.S.C. 154(b) by 363 days.

(21) Appl. No.: 11/572,801

(22) PCT Filed: Jul. 20, 2005

(86) PCT No.: PCT/EP2005/007892

§ 371 (c)(1),
(2), (4) Date: Jan. 26, 2007

(87) PCT Pub. No.: WO2006/010544

PCT Pub. Date: Feb. 2, 2006

(65) Prior Publication Data

US 2008/0064740 A1  Mar. 13, 2008

(30) Foreign Application Priority Data

Jul. 29, 2004  (WO) ............... PCT/EP2004/008501

(51) Int. Cl.
*A61K 31/381*  (2006.01)
*C07D 333/78*  (2006.01)

(52) U.S. Cl. .................. 514/443; 549/43; 549/48
(58) Field of Classification Search .......... 549/43, 549/48; 514/443
See application file for complete search history.

(56) References Cited

U.S. PATENT DOCUMENTS

| 4,808,599 A | 2/1989 | Dubroeucq et al. |
| 6,156,787 A | 12/2000 | Broughton et al. |
| 2004/0058894 A1 | 3/2004 | Doherty et al. |
| 2006/0293252 A1 | 12/2006 | Glombik et al. |
| 2008/0005421 A1 | 1/2008 | Chang et al. |
| 2008/0176926 A1 | 7/2008 | Bolli et al. |
| 2008/0194670 A1 | 8/2008 | Bolli et al. |
| 2008/0300294 A1 | 12/2008 | Bolli et al. |
| 2008/0318955 A1 | 12/2008 | Bolli et al. |

FOREIGN PATENT DOCUMENTS

| EP | 0 310 321 | 4/1989 |
| EP | 0 476 646 A1 | 3/1992 |
| GB | 2 336 588 | 10/1999 |
| WO | WO-91/15583 A1 | 10/1991 |
| WO | WO-99/46277 A1 | 9/1999 |
| WO | WO-03/014107 A1 | 2/2003 |
| WO | WO 03/062248 | 7/2003 |
| WO | WO-03/062248 A2 | 7/2003 |
| WO | WO-03/105771 | 12/2003 |
| WO | WO-2004/007517 A1 | 1/2004 |
| WO | WO-2004/010949 A2 | 2/2004 |
| WO | WO-2004/035538 | 4/2004 |
| WO | WO-2004/103279 | 12/2004 |
| WO | WO-2005/014525 A2 | 2/2005 |
| WO | WO-2005/032465 A2 | 4/2005 |
| WO | WO-2005/058848 A1 | 6/2005 |
| WO | WO-2006/010379 A1 | 2/2006 |
| WO | WO-2006/100631 | 9/2006 |
| WO | WO-2006/131336 A1 | 12/2006 |
| WO | WO-2006/137019 A1 | 12/2006 |
| WO | WO-2007/085451 A2 | 8/2007 |
| WO | WO-2008/076356 A1 | 6/2008 |
| WO | WO-2008/091967 A1 | 7/2008 |

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Incv., 1999, 1-2, 183-226.*
U.S. Appl. No. 11/909,440.
U.S. Appl. No. 11/909,436.
U.S. Appl. No. 11/909,429.
U.S. Appl. No. 11/993,563.
U.S. Appl. No. 12/160,520.
Brinkmann, V. et al.; "The Immune Modulator FTY720 Targets Sphingosine 1-Phospate Receptors"; The Journal of Biological Chemistry, vol. 277, No. 24, Jun. 14, 2002, pp. 21453-21457.
Matloubian, M. et al.;"Lymphocyte egress from thymus and peripheral lymphoid organs is dependent on S1P receptor 1"; Nature, vol. 427, Jan. 22, 2004, pp. 355-360.
Christl, M. et al.; "Einige Valene von benzanellierten fuenfgliedrigen Heteroarenen—Synthesen and NMR-Spektren"; Angewandte Chemie, vol. 102, No. 6, 1990, pp. 704-706.

(Continued)

Primary Examiner—Patricia L Morris
(74) Attorney, Agent, or Firm—Hoxie & Associates LLC

(57) ABSTRACT

The invention relates to novel thiophene derivatives, their preparation and their use as pharmaceutically active compounds. Said compounds particularly act as immunosuppressive agents.

16 Claims, No Drawings

OTHER PUBLICATIONS

Actelion: "Company Presention"; Internet Article, Nov. 2005, pp. 23-25.
Hla, T. et al.;"An Abundant Transcript Induced in Differentiating Human Endothelial Cells Encodes a Polypeptide with Structural Similarities to G-protein-coupled Receptors"; The Journal of Biological Chemistry, vol. 265, No. 16, Jun. 5, 1990, pp. 9308-9313.
Berge, S. et al.; "Pharmaceutical Salts"; Journal of Pharmaceutical Sciences, vol. 66, No. 1, Jan. 1977, pp. 1-19.
Gould, P.L.; "Salt selection for basic drugs"; *International Journal of Pharmaceutics*, 33 (1986), pp. 201-217.
Mentzel, M. et al.; "*N*-Methoxy-*N*-methylamides (Weinreb Amides) in Modern Organic Synthesis"; Journal fuer praktische Chemie Chemiker-Zeitung, 339, (1997), pp. 517-524.
Singh, J. et al.; "The Growing Synthetic Utility of Weinreb's Amide"; Journal fuer Praktische Chemie (Weinheim, Germany), 342, (2000), pp. 340-347.
Khlestkin, V. et al.; "Recent Advances in the Application of N,O-Dialkylhydroxylamines in Organic Chemistry"; *Current Organic Chemistry*, 7, (2003), pp. 967-993.
Cocker, W. et al.; "A Convenient Preparation of (−)-β-3,4-Epoxycarane"; Tetrahedron Letters, No. 51 (1969), pp. 4451-4452.
Lochynski, S. et al.; "Modification of Synthesis of Dihydrochrysanthemolactone from (+)-Car-3-ene"; Journal fuer praktische Chemie (Leipzig), 330 (1988), pp. 284-288.
Walkowicz, M. et al.; "Ueber Stereoisomere 6,6-Dimethyl-Bicyclo-[3.1.0]-Hexanole-3"; Roczniki Chemii Ann. Soc. Chim. Polonorum, 41 (1967), pp. 927-937.
Kuczynski, H. et al.; "O Krystalicznym (−)-Dwubromo-3,4-Karanie" Roczniki Chemii Ann. Soc. Chim. Polonorum, 38 (1964), pp. 1625-1633.
Pol, A.V. et al.; "Oxidation of $\Delta^3$-Carene & α-Pinene with Thallium(III) Nitrate"; Indian J. Chem, vol. 19B, Jul. 1980, pp. 603-604.
Popov, S.A. et al.; "Synthesis of New Chiral Heterocycles of the Pyrazole and 2-Isoxazoliine Types from (+)-3-Carene"; *Tetrahedron: Asymmetry*, vol. 5, No. 3, (1994), pp. 479-489.
Popov, S.A. et al.; "Synthesis of 2-Alkyl and 2-Aryl Pyrimidines From β-Chlorovinyl Ketones of Cyclopentanone Type"; Synthetic Communications, 31 (2001), pp. 233-243.
Gannett, P.M. et al.; "The Capsaicinoids: Their Separation, Synthesis, and Mutagenictiy"; *J. Org. Chem.*, 53 (1988), pp. 1064-1071.
Motion, K.R. et al.;"Reactions of Diene-conjugated 1,3-Dipolar Intermediates: the Formation of Cyclopropa[c]isoquinolines from Benzonitrile o-Alkenylbenzyl Ylides and their Rearrangements to Benzazepines"; J. Chem. Soc. Perkin Trans., 1 (1992), pp. 1709-1719.
Xu, B. et al.; "Acyclic Analogues of Adenosine Bisphosphates as P2Y Receptor Antagonists: Phosphate Substitution Leads to Multiple Pathways of Inhibiition of Platelet Aggregation"; *J. Med. Chem.* 45 (2002), pp. 5694-5709.
Fujii, N. et al., "Transition Metal-Catalyzed Intramolecular Cyclization of 1,5- and 1,6-Dienes via Direct Cleavage and Addition of the Carbon-Hydrogen Bond," Bull. Chem.. Soc. Jpn., vol. 71, 1998, pp. 285-298.
Thiemann. T. et al.; "One pot Suzuki coupling—Wittig olefination reactions", Journal of Chemical Research 2004, November, pp. 723-727.
Yamagata, K. et al., "Studies on Heterocyclic Enaminonitriles. II.[1)] Synthesis and Aromatization of 2-Amino-3-cyano-4,5-dihydrothiophenes," Chemical & Pharmaceutical Bulletin 30 (1982). pp. 4396-4401.

* cited by examiner

THIOPHENE DERIVATIVES

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing one or more compounds of the Formula (I) and their use as compounds improving vascular function and as immunomodulating agents, either alone or in combination with other active compounds or therapies. A further aspect of the invention relates to novel compounds of Formula (IV) that serve as intermediates to prepare compounds of Formula (I).

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol. Chem.* 265 (1990), 9308-9313; WO91/15583 published 17 Oct. 1991; WO99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see Examples).

The following paragraphs provide definitions of the various chemical moieties that make up the compounds according to the invention and are intended to apply uniformly throughout the specification and claims unless an otherwise expressly set out definition provides a broader definition.

The term alkyl, alone or in combination with other groups, means saturated, straight or branched chain groups with one to seven carbon atoms, preferably one to four carbon atoms. Examples of alkyl groups are methyl, ethyl, n-propyl, iso-propyl, n-butyl, iso-butyl, sec-butyl, tert-butyl, n-pentyl, n-hexyl or n-heptyl.

The term alkoxy means an R—O group, wherein R is an alkyl group. Preferred examples of alkoxy groups are methoxy, ethoxy, propoxy, iso-propoxy, iso-butoxy, sec-butoxy or tert-butoxy.

The term hydroxy-alkoxy means a straight or branched alkoxy chain bearing a hydroxy group whereby there are at least two carbon atoms between the hydroxy group and the oxygen of the alkoxy group. Examples of hydroxy-alkoxy groups are 2-hydroxy-ethoxy, 3-hydroxy-propoxy, 2-hydroxy-propoxy, 4-hydroxy-butoxy, 3-hydroxy-1-methyl-propoxy, 3-hydroxy-butoxy, etc.

The term mono- or di-alkylamino means an R'—NH— or an R'—NR"— group, wherein R' and R" are each independently an alkyl group. Preferred examples of mono- or di-alkylamino groups are methylamino, ethylamino, N,N-dimethylamino, or N-methyl-N-ethyl-amino.

The term halogen means fluoro, chloro, bromo or iodo, preferably fluoro or chloro.

If in Formula (I) A represents an asymmetric bivalent radical, the orientation of the radical is as such that the left part of the radical is always attached to the carbonyl group of Formula (I). In other words, if A represents —$CH_2NH$—, the $CH_2$ part of this radical is attached to the carbonyl group of Formula (I).

Salts are preferably the pharmaceutically acceptable salts of the compounds of Formula (I).

Salt-forming groups are groups or radicals having basic or acidic properties. Compounds having at least one basic group or at least one basic radical, for ex-ample amino, a secondary amino group not forming a peptide bond or a pyridyl radical, may form acid addition salts, for example with inorganic acids. When several basic groups are present mono- or poly-acid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric or hydrobromic acid, sulfuric acid, phosphoric acid, citric acid, formic acid, acetic acid, maleic acid, tartaric acid, benzoic acid, methanesulfonic acid, p-toluenesulfonic acid, and the like that are non-toxic to living organisms. In case a compound of Formula (I) is acidic in nature the expression encompasses salts with an inorganic base like an alkali or earth alkali base, e.g. sodium hydroxide, potassium hydroxide, calcium hydroxide, or with an organic base such as benzathine, choline, meglumine, and the like which are also non-toxic to living organisms (S. M. Berge, L. D. Bighley and D. C. Monkhouse, Pharmaceutical salts, *J. Pharm. Sci.,* 66 (1977), 1-19; P. L. Gould, Salt selection of basic drugs, *Int. J. Pharmaceutics* 33 (1986), 201-217).

i) The invention relates to novel thiophene compounds of the Formula (I)

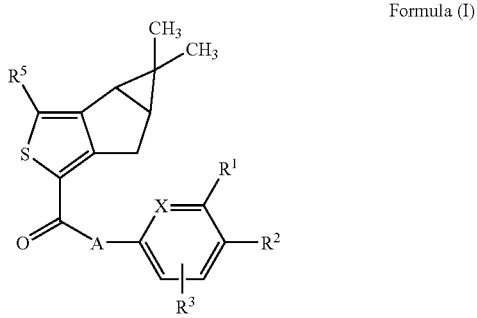

Formula (I)

wherein

A represents —$CH_2CH_2$—, —$CH=CH$—, —$NH—CH_2$—, —$CH_2—O$—, or —$CH_2NH$—, preferably —$CH_2CH_2$— or —$CH_2NH$—;

$R^1$ represents hydrogen or alkyl; in the case X represents C—$R^4$, $R^1$ in addition represents halogen; and in the case A represents —$CH_2—CH_2$— or —$CH_2NH$—, $R^1$ in addition represents alkoxy;

$R^2$ represents hydrogen, alkoxy, fluoro-alkoxy, hydroxy-alkoxy, hydroxy-alkyl, di-(hydroxy-alkyl)-alkyl, di-(hydroxy-alkyl)-alkoxy, 1-glyceryl, 2-glyceryl, pyridin-3-yl-methoxy, or pyridin-4-yl-methoxy;

$R^3$ represents hydrogen, alkyl, mono- or di-alkylamino, trifluoromethyl, or trifluoromethoxy; in the case X represents C—$R^4$, $R^3$ in addition represents halogen; and in the case A represents —$CH_2—CH_2$— or —$CH_2NH$—, $R^3$ in addition represents alkoxy;

X represents N or C—$R^4$;

$R^4$ represents hydrogen, alkyl, alkoxy, or halogen; and

—$R^5$ represents methyl or ethyl;

and configurational isomers such as optically pure enantiomers, mixtures of enantiomers such as racemates, diastereomers, mixtures of diastereomers, diastereomeric racemates, and mixtures of diastereomeric racemates, as well as salts and solvent complexes of such compounds, and morphological forms.

ii) A particular embodiment of the invention relates to thiophene compounds according to the above embodiment i), wherein A represents —$CH_2CH_2$—, —$CH=CH$—, or —$NH—CH_2$—;

$R^1$ represents hydrogen or alkyl, and in the case X represents C—$R^4$, $R^1$ in addition represents halogen;

$R^3$ represents hydrogen, alkyl, mono- or di-alkylamino, trifluoromethyl, or trifluoromethoxy; and in the case X represents C—$R^4$, $R^3$ in addition represents halogen; and $R^5$ represents methyl.

iii) A preferred embodiment of the invention relates to thiophene compounds according to the above embodiment i) or ii), wherein A represents —$CH=CH$—.

iv) Another preferred embodiment of the invention relates to thiophene compounds according to the above embodiment i) or ii), wherein A represents —$NH—CH_2$—.

v) Another preferred embodiment of the invention relates to thiophene compounds according to the above embodiment i) or ii), wherein A represents —$CH_2CH_2$—.

vi) A very preferred embodiment of the invention relates to thiophene compounds according to the above embodiment i) or ii), wherein A represents —$CH_2NH$—.

vii) Another preferred embodiment of the invention relates to thiophene compounds according to any one of the above embodiments i) to vi), wherein X represents N.

viii) Another preferred embodiment of the invention relates to thiophene compounds according to any one of the above embodiments i) to vi), wherein X represents C—$R^4$.

ix) A further preferred embodiment of the invention relates to thiophene compounds according to any one of the above embodiments i) to vi), wherein X represents C—$R^4$, whereby $R^4$ represents a methoxy group, and $R^1$ represents hydrogen.

x) Another further preferred embodiment of the invention relates to thiophene compounds according to any one of the above embodiments i) to vi), wherein X represents C—$R^4$, whereby $R^4$ represents a methoxy group, and $R^1$ and $R^3$ both represent hydrogen.

xi) Another preferred embodiment of the invention relates to thiophene compounds according to any one of the above embodiments i) to x), wherein $R^2$ represents hydroxy-alkoxy, hydroxy-alkyl, di-(hydroxy-alkyl)-alkoxy, di-(hydroxy-alkyl)-alkyl, 1-glyceryl, or 2-glyceryl.

xii) Another preferred embodiment of the invention relates to thiophene compounds according to the above embodiment xi), wherein $R^2$ represents an (S)-1-glyceryl group.

xiii) Another preferred embodiment of the invention relates to thiophene compounds according to any one of the above embodiments i) to vi), wherein X represents C—$R^4$, whereby $R^4$ represents hydrogen, $R^1$ and $R^3$ both represent a methyl group, preferably ortho to $R^2$, and $R^2$ represents hydroxy-alkoxy, hydroxy-alkyl, di-(hydroxy-alkyl)-alkoxy, di-(hydroxy-alkyl)-alkyl, 1-glyceryl, or 2-glyceryl.

xiv) A particularly preferred embodiment of the invention relates to thiophene compounds of the Formula (II)

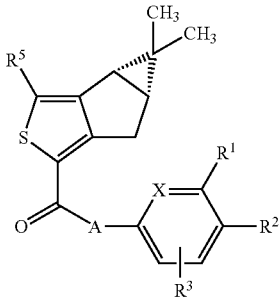

Formula (II)

according to any one of the above embodiments i) to xiii).

xv) Another preferred embodiment of the invention relates to thiophene compounds of the Formula (III)

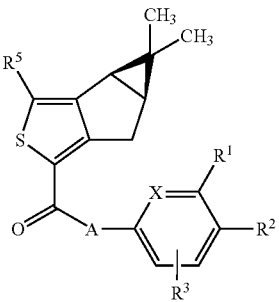

Formula (III)

according to any one of embodiments i) to xiii).

xvi) A further preferred embodiment of the invention relates to thiophene compounds according to the above embodiment i), wherein A represents —$CH_2CH_2$—, —NH—$CH_2$—, —$CH_2$—O—, or —$CH_2NH$—, preferably —$CH_2CH_2$— or —$CH_2NH$—;

$R^2$ represents hydrogen, alkoxy, fluoro-alkoxy, hydroxy-alkoxy, hydroxy-alkyl, di-(hydroxy-alkyl)-alkoxy, 1-glyceryl, pyridin-3-yl-methoxy, or pyridin-4-yl-methoxy; and $R^3$ represents hydrogen, alkyl, or trifluoromethyl; in the case X represents C—$R^4$, $R^3$ in addition represents halogen; and in the case A represents —$CH_2$—$CH_2$— or —$CH_2NH$—, $R^3$ in addition represents alkoxy.

xvii) Specific thiophene compounds according to Formula (I) are:
(1aS,5aR)-1,1,2-Trimethyl-1,1a,5,5a-tetrahydro-3-thia-cyclopropa[a]pentalene-4-carboxylic acid 2-methoxy-benzylamide,
(1aS,5aR)-1,1,2-trimethyl-1,1a,5,5a-tetrahydro-3-thia-cyclopropa[a]pentalene-4-carboxylic acid 2,4-dimethoxy-benzylamide,
(1aS,5aR)-1,1,2-trimethyl-1,1a,5,5a-tetrahydro-3-thia-cyclopropa[a]pentalene-4-carboxylic acid 4-ethoxy-2-methoxy-benzylamide,
(1aS,5aR)-1,1,2-trimethyl-1,1a,5,5a-tetrahydro-3-thia-cyclopropa[a]pentalene-4-carboxylic acid 2-methyl-benzylamide,
(1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-2-methoxy-benzylamide,
(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-2-methoxy-benzylamide,
(1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3-methyl-benzylamide,
(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3-methyl-benzylamide,
(1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3-chloro-benzylamide,
(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3-chloro-benzylamide,
(1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-2-chloro-benzylamide,
(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-2-chloro-benzylamide,
(1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-benzylamide,
(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-benzylamide,
(1aS,5aR)-1,1,2-trimethyl-1,1a,5,5a-tetrahydro-3-thia-cyclopropa[a]pentalene-4-carboxylic acid 4-(2-hydroxy-ethoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 4-(2-hydroxy-ethoxy)-2-methoxy-benzylamide, (1aS,5aR)-1,1,2-trimethyl-1,1a,5,5a-tetrahydro-3-thia-cyclopropa[a]pentalene-4-carboxylic acid 4-(2-hydroxy-ethoxy)-3-methyl-benzylamide,
(1aS,5aR)-1,1,2-trimethyl-1,1a,5,5a-tetrahydro-3-thia-cyclopropa[a]pentalene-4-carboxylic acid 4-(2-hydroxy-ethoxy)-3-chloro-benzylamide,
(1aS,5aR)-1,1,2-trimethyl-1,1a,5,5a-tetrahydro-3-thia-cyclopropa[a]pentalene-4-carboxylic acid 4-(2-hydroxy-ethoxy)-2-chloro-benzylamide,
(1aS,5aR)-1,1,2-trimethyl-1,1a,5,5a-tetrahydro-3-thia-cyclopropa[a]pentalene-4-carboxylic acid 4-(2-hydroxy-ethoxy)-benzylamide,
(1aS,5aR)-1,1,2-trimethyl-1,1a,5,5a-tetrahydro-3-thia-cyclopropa[a]pentalene-4-carboxylic acid 4-((R/S)-2-hydroxy-propoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 4-((R/S)-2-hydroxy-propoxy)-2-methoxy-benzylamide,
(1aS,5aR)-1,1,2-trimethyl-1,1a,5,5a-tetrahydro-3-thia-cyclopropa[a]pentalene-4-carboxylic acid 4-((R/S)-2-hydroxy-propoxy)-3-methyl-benzylamide,
(1aS,5aR)-1,1,2-trimethyl-1,1a,5,5a-tetrahydro-3-thia-cyclopropa[a]pentalene-4-carboxylic acid 4-((R/S)-2-hydroxy-propoxy)-3-chloro-benzylamide,
(1aS,5aR)-1,1,2-trimethyl-1,1a,5,5a-tetrahydro-3-thia-cyclopropa[a]pentalene-4-carboxylic acid 4-((R/S)-2-hydroxy-propoxy)-2-chloro-benzylamide,
(1aS,5aR)-1,1,2-trimethyl-1,1a,5,5a-tetrahydro-3-thia-cyclopropa[a]pentalene-4-carboxylic acid 4-((R/S)-2-hydroxy-propoxy)-benzylamide,
(1aS,5aR)-1,1,2-trimethyl-1,1a,5,5a-tetrahydro-3-thia-cyclopropa[a]pentalene-4-carboxylic acid 4-(3-hydroxy-propoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 4-(3-hydroxy-propoxy)-2-methoxy-benzylamide,
(1aS,5aR)-1,1,2-trimethyl-1,1a,5,5a-tetrahydro-3-thia-cyclopropa[a]pentalene-4-carboxylic acid 4-(3-hydroxy-propoxy)-3-methyl-benzylamide,
(1aS,5aR)-1,1,2-trimethyl-1,1a,5,5a-tetrahydro-3-thia-cyclopropa[a]pentalene-4-carboxylic acid 4-(3-hydroxy-propoxy)-3-chloro-benzylamide,
(1aS,5aR)-1,1,2-trimethyl-1,1a,5,5a-tetrahydro-3-thia-cyclopropa[a]pentalene-4-carboxylic acid 4-(3-hydroxy-propoxy)-2-chloro-benzylamide,
(1aS,5aR)-1,1,2-trimethyl-1,1a,5,5a-tetrahydro-3-thia-cyclopropa[a]pentalene-4-carboxylic acid 4-(3-hydroxy-propoxy)-benzylamide,
(1aS,5aR)-1,1,2-trimethyl-1,1a,5,5a-tetrahydro-3-thia-cyclopropa[a]pentalene-4-carboxylic acid 4-(2-fluoro-ethoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 4-(2-fluoro-ethoxy)-2-methoxy-benzylamide,
(1aS,5aR)-1,1,2-trimethyl-1,1a,5,5a-tetrahydro-3-thia-cyclopropa[a]pentalene-4-carboxylic acid 2-chloro-4-(2-fluoro-ethoxy)-benzylamide,
(1aS,5aR)-1,1,2-trimethyl-1,1a,5,5a-tetrahydro-3-thia-cyclopropa[a]pentalene-4-carboxylic acid 4-(2-fluoro-ethoxy)-benzylamide,
(1aS,5aR)-1,1,2-trimethyl-1,1a,5,5a-tetrahydro-3-thia-cyclopropa[a]pentalene-4-carboxylic acid 4-(3-fluoro-propoxy)-2-methoxy-benzylamide,
(1aS,5aR)-1,1,2-trimethyl-1,1a,5,5a-tetrahydro-3-thia-cyclopropa[a]pentalene-4-carboxylic acid 2-methoxy-4-propoxy-benzylamide,
(1aS,5aR)-1,1,2-trimethyl-1,1a,5,5a-tetrahydro-3-thia-cyclopropa[a]pentalene-4-carboxylic acid 2-methoxy-4-isopropoxy-benzylamide,
(1aS,5aR)-1,1,2-trimethyl-1,1a,5,5a-tetrahydro-3-thia-cyclopropa[a]pentalene-4-carboxylic acid 4-isobutoxy-2-methoxy-benzylamide,
(1aS,5aR)-1,1,2-trimethyl-1,1a,5,5a-tetrahydro-3-thia-cyclopropa[a]pentalene-4-carboxylic acid 4-(6-hydroxy-hexyloxy)-2-methoxy-benzylamide,
(1aS,5aR)-1,1,2-trimethyl-1,1a,5,5a-tetrahydro-3-thia-cyclopropa[a]pentalene-4-carboxylic acid 4-(3-hydroxy-2-hydroxymethyl-propoxy)-3,5-dimethyl-benzylamide,
(1aS,5aR)-1,1,2-trimethyl-1,1a,5,5a-tetrahydro-3-thia-cyclopropa[a]pentalene-4-carboxylic acid 2-methoxy-4-(pyridin-3-ylmethoxy)-benzylamide,
(1aS,5aR)-1,1,2-trimethyl-1,1a,5,5a-tetrahydro-3-thia-cyclopropa[a]pentalene-4-carboxylic acid 2-methoxy-4-(pyridin-4-ylmethoxy)-benzylamide,
(1aS,5aR)-1,1,2-trimethyl-1,1a,5,5a-tetrahydro-3-thia-cyclopropa[a]pentalene-4-carboxylic acid (pyridin-2-ylmethyl)-amide,
3-(2-methoxy-phenyl)-1-((1aS,5aR)-1,1,2-trimethyl-1,1a,5,5a-tetrahydro-3-thia-cyclopropa[a]penta-len-4-yl)-propan-1-one,
3-[4-((S)-2,3-dihydroxy-propoxy)-2-methoxy-phenyl]-1-((1aS,5aR)-1,1,2-trimethyl-1,1a,5,5a-tetrahydro-3-thia-cyclopropa[a]pentalen-4-yl)-propan-1-one,
3-[4-(2-hydroxy-ethoxy)-2-methoxy-phenyl]-1-((1aS,5aR)-1,1,2-trimethyl-1,1a,5,5a-tetrahydro-3-thia-cyclopropa[a]pentalen-4-yl)-propan-1-one,
3-[4-((S)-2,3-dihydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one,
3-[4-((R)-2,3-dihydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one,
3-[4-(2-hydroxy-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one,
3-[4-(2-(R/S)-hydroxy-propoxy)-3,5-dimethyl-phenyl]-1-(1,1,2-trimethyl-1,1a,5,5a-tetrahydro-3-thia-cyclopropa[a]pentalen-4-yl)-propan-1-one,
3-[4-(2-(2-fluoroethoxy)-3,5-dimethyl-phenyl]-1-(1,1,2-trimethyl-1,1a,5,5a-tetrahydro-3-thia-cyclopropa[a]pentalen-4-yl)-propan-1-one, and
3-[4-(3-hydroxy-propoxy)-3,5-dimethyl-phenyl]-1-(1,1,2-trimethyl-1,1a,5,5a-tetrahydro-3-thia-cyclopropa[a]pentalen-4-yl)-propan-1-one.

xviii) Further specific thiophene compounds according to Formula (I) are:
3-[4-(3-Hydroxy-2-hydroxymethyl-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one,
3-[4-((S)-2,3-dihydroxy-propoxy)-3-ethyl-5-methyl-phenyl]-1-((1aS,5aR)-1,1,2-trimethyl-1,1a,5,5a-tetrahydro-3-thia-cyclopropa[a]pentalen-4-yl)-propan-1-one,
3-[4-((R)-2,3-dihydroxy-propoxy)-3-ethyl-5-methyl-phenyl]-1-((1aS,5aR)-1,1,2-trimethyl-1,1a,5,5a-tetrahydro-3-thia-cyclopropa[a]pentalen-4-yl)-propan-1-one,
3-[3-ethyl-4-(2-hydroxy-ethoxy)-5-methyl-phenyl]-1-((1aS,5aR)-1,1,2-trimethyl-1,1a,5,5a-tetrahydro-3-thia-cyclopropa[a]pentalen-4-yl)-propan-1-one,
3-[4-((S)-2,3-dihydroxy-propoxy)-3,5-diethyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((S)-2,3-dihydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((R)-2,3-dihydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-(2-hydroxy-ethoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-(2-hydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-(2-hydroxy-ethoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-(3-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3-methyl-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one, 3-[3,5-dichloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[3,5-dichloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[3,5-dichloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((S)-2,3-dihydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((R)-2,3-dihydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-(2-hydroxy-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3-fluoro-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-((R)-2,3-dihydroxy-propoxy)-3-fluoro-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[3-fluoro-4-(2-hydroxy-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-(3-hydroxy-propyl)-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3,5-dimethyl-phenyl]-1-((1aR,5aS)-2-ethyl-1,1-dimethyl-1,1a,5,5a-tetrahydro-3-thia-cyclopropa[a]pentalen-4-yl)-propan-1-one, 3-[4-((R)-2,3-dihydroxy-propoxy)-3,5-dimethyl-phenyl]-1-((1aR,5aS)-2-ethyl-1,1-dimethyl-1,1a,5,5a-tetrahydro-3-thia-cyclopropa[a]pentalen-4-yl)-propan-1-one, 1-((1aR,5aS)-2-ethyl-1,1-dimethyl-1,1a,5,5a-tetrahydro-3-thia-cyclopropa[a]pentalen-4-yl)-3-[4-(3-hydroxy-propoxy)-3,5-dimethyl-phenyl]-propan-1-one, 1-((1aR,5aS)-2-ethyl-1,1-dimethyl-1,1a,5,5a-tetrahydro-3-thia-cyclopropa[a]pentalen-4-yl)-3-[4-(2-hydroxy-propoxy)-3,5-dimethyl-phenyl]-propan-1-one, 2-(2-methoxy-phenylamino)-1-((1aS,5aR)-1,1,2-trimethyl-1,1a,5,5a-tetrahydro-3-thia-cyclopropa[a]pentalen-4-yl)-ethanone, 2-(3,5-dimethyl-phenylamino)-1-((1aS,5aR)-1,1,2-trimethyl-1,1a,5,5a-tetrahydro-3-thia-cyclopropa[a]pentalen-4-yl)-ethanone, and 2-[4-(2-hydroxy-ethyl)-phenylamino]-1-((1aS,5aR)-1,1,2-trimethyl-1,1a,5,5a-tetrahydro-3-thia-cyclopropa[a]pentalen-4-yl)-ethanone.

xix) A further aspect of the invention relates to novel compounds of Formula (IV)

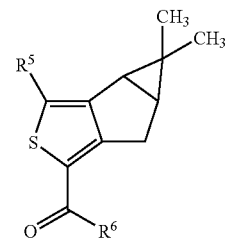

Formula (IV)

wherein $R^5$ is as defined for Formula (I) above; and $R^6$ represents hydroxy, alkoxy, or methyl;

and configurational isomers such as optically pure enantiomers, mixtures of enantiomers such as racemates, diastereomers, mixtures of diastereomers, diastereomeric racemates, and mixtures of diastereomeric racemates, as well as salts and solvent complexes of such compounds, and morphological forms.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, The Science and Practice of Pharmacy, 20th Edition, Philadelphia College of Pharmacy and Science) by bringing the described compounds of Formula (I) and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable inert carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage of the compounds of Formula (I) can vary within wide limits depending on the disease to be controlled, the age and the individual condition of the patient and the mode of administration, and will, of course, be fitted to the individual requirements in each particular case. For adult patients a daily dosage of about 0.5 mg to about 1000 mg, especially about 1 mg to about 500 mg, comes into consideration for the treatment of disorders associated with an activated immune system for adult patients. Depending on the dosage it may be convenient to administer the daily dosage in several dosage units.

The pharmaceutical compositions conveniently contain about 0.5 to 500 mg, preferably 1 to 250 mg, of a compound of Formula (I).

The above-mentioned pharmaceutical composition is useful for the prevention and treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' opthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fasciitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung solid cancer; malignancy of lymphoid origin; acute or chronic lymphocytic leukemias; lymphoma; psoriasis; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure.

Preferred diseases or disorders to be treated or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a patient a pharmaceutically active amount of a compound of Formula (I).

Furthermore, compounds of the Formula (I) are also useful, in combination with one or several immunomodulating agents, for the prevention or treatment of the diseases and disorders mentioned herein. According to a preferred embodiment of the invention, said agent is selected from the group consisting of immunosuppressants, steroids such as especially corticosteroids, NSAID's, cytotoxic drugs, adhesion molecule inhibitors, cytokines, cytokine inhibitors, cytokine receptor antagonists and recombinant cytokine receptors.

In particular, compounds of the Formula (I) are useful in combination with one or several agents selected from the group comprising or consisting of cyclosporin, monoclonal antibodies such as daclizumab and basiliximab, everolimus, tacrolimus (FK506), sirolimus, azathioprine, leflunomide, 15-deoxyspergualin, mycophenolate mofetil, methothrexate, and 5-aminosalicylic acid.

Still a further object of the present invention is a process to prepare a pharmaceutical composition comprising a compound of the Formula (I) by mixing one or more active ingredients with inert excipients in a manner known per se.

The present invention also relates to the use of a compound of Formula (I) for the preparation of a pharmaceutical composition, optionally for use in combination with one or several immunomodulating agents, for the prevention or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I) as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

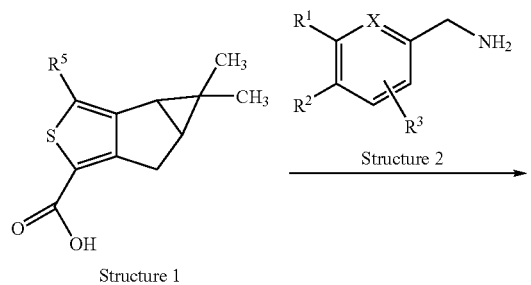

Structure 1    Structure 2

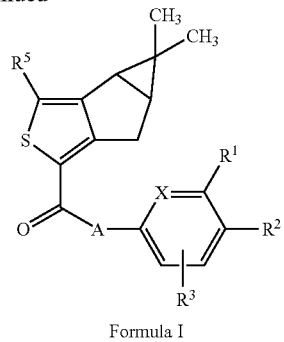

Formula I

In case A represents —NH—CH$_2$—, the compounds of the Formula (I) may be prepared by reacting a compound of Structure 1 with a compound of Structure 2 in the presence of an activating agent such as EDC, DCC, HOBt, BOP, PyBOP, BOP-Cl, etc. in a solvent such as THF, dioxane, DMF, DCM, acetonitrile, etc. Depending on the nature of the functionalities present in the residues $R^1$ to $R^3$, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^1$ to $R^3$ may also be introduced in later steps that follow the reaction of a compound of Structure 1 with a suitable precursor of a compound of Structure 2. The compounds of Structure 2 are either commercially available or are prepared according to procedures known to a person skilled in the art.

In case A represents —CH$_2$—CH$_2$—, the compounds of Formula (I) may be prepared by reacting a compound of Structure 3 with a compound of Structure 4 under Grignard conditions, preferably at temperatures below rt. The Grignard reagent of Structure 4 is prepared according to standard methodology. As above, the functional groups present in the residues $R^1$ to $R^3$ may require temporary protection or may even be introduced in additional steps that follow the Grignard reaction. The Weinreb amide compounds of Structure 3 are prepared by treating a compound of Structure 1 with N,O-dimethylhydroxylamine hydrochloride in the presence of coupling reagents such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, Current Organic Chemistry 7 (2003), 967-993).

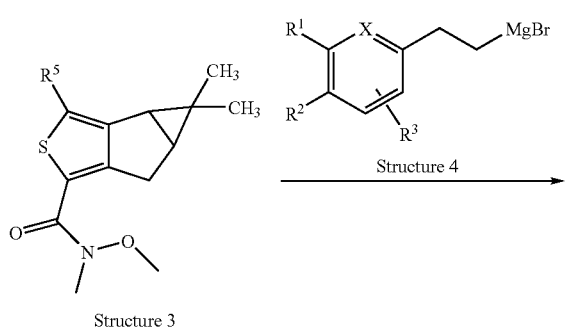

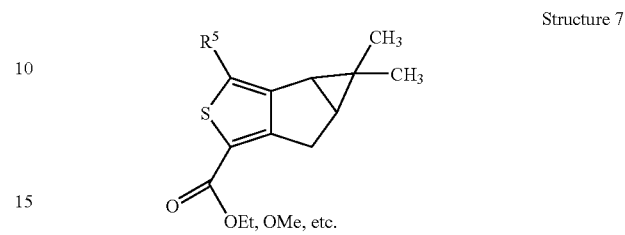

The compounds of Structure 1 may be prepared by reacting a compound of Structure 7 with an aqueous base such as aq. NaOH, aq. LiOH, aq. KOH, etc. or an acid such as aq. HCl, TFA, etc. in a solvent such as water, ethanol, methanol, THF, etc. or mixtures thereof.

In case A represents —CH=CH—, the compounds of Formula (I) may be prepared by reacting a compound of Structure 5 with a compound of Structure 6. Compounds of Formula (I) wherein A represents —CH$_2$—CH$_2$— may also be prepared by reacting a compound of Formula (I) wherein A represents —CH=CH— with hydrogen in the presence of a catalyst such as Pd/C, Pt/C, PtO$_2$, etc. in a solvent such as ethanol, methanol, THF, etc.

The compounds of Structure 7 may be prepared by treating a compound of Structure 8 with a non aqueous base such as NaOMe, NaOEt, KO-tert.-Bu, DBU, etc. in a solvent such as methanol, ethanol, THF, DMF, etc. or mixtures thereof preferably at elevated temperatures.

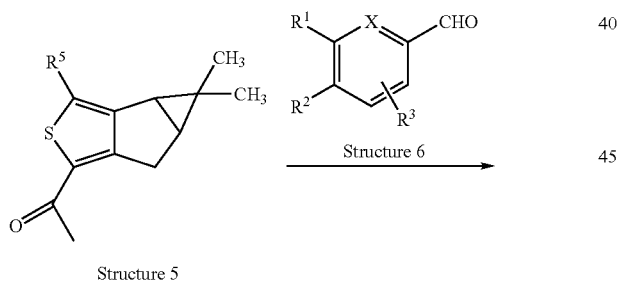

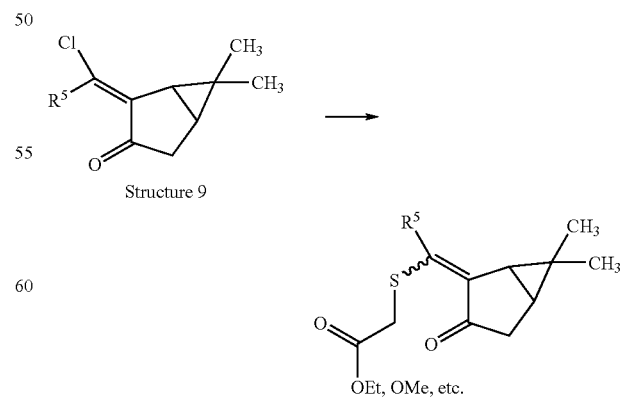

The compounds of Structure 5 may be prepared by treating a compound of Structure 1 with MeLi in a solvent such as THF, dioxane, and diethyl ether at temperatures below rt.

The compounds of Structure 8 may be prepared by treating a compound of Structure 9 with a 2-mercaptoacetic acid ester in the presence of a base such a NaH in THF, dioxane, DMF, or mixtures thereof.

The racemic form of Structure 9 may be prepared starting from (+)-3-carene following the procedures given in the literature (W. Cocker, D. H. Grayson, *Tetrahedron Lett.* 51 (1969), 4451-4452; S. Lochynski; B. Jarosz, M. Walkowicz, K. Piatkowski, *J. Prakt. Chem. (Leipzig)* 330 (1988), 284-288; M. Walkowicz, H. Kuczynsky, C. Walkowicz, *Roczniki Chemii Ann. Soc. Chim. Polonorum* 41 (1967), 927-937; H. Kuczynski, M. Walkowicz, C. Walkowicz, K. Nowak, I. Z. Siemion, *Roczniki Chemii Ann. Soc. Chim. Polonorum,* 38 (1964), 1625-1633; A. V. Pol, V. G. Naik, H. R. Sonawane, *Ind. J. Chem. Sect. B,* 19 (1980) 603-604; S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) and is exemplified below.

The compounds of Formula (II) may be prepared by starting from the pure (1S,5R)-stereoisomer of Structure 9 ((1S, 5R)-isomer of 2-[1-chloro-ethylidene]-6,6-dimethyl-bicyclo [3.1.0]hexan-3-one, Structure 10) which may be prepared starting from commercially available (+)-3-carene according to the procedures given in the literature (e.g. S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243).

Structure 10

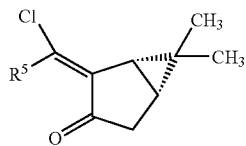

The compounds of the Formula (III) may be obtained by resolving the racemic mixture of a compound of Formula (I) or one of its precursors (e.g. Structure 9) into its pure enantiomers by a method known per se to a person skilled in the art, preferably by chromatography or crystallisation.

Compounds of the Formula (I) wherein A represents —$CH_2$—O— or —$CH_2$—NH— may be prepared by reacting a compound of Structure 11 with a compound of Structure 12 in the presence or absence of a base such as $K_2CO_3$, $Na_2CO_3$, K-tert.butoxide, NaOH, NaH, triethylamine, DIPEA, etc. in a solvent such as acetone, DMF, THF, dioxane, etc. or mixtures thereof. The compounds of Structure 11 can be prepared by reacting a compound of Structure 5 with a brominating agent such as phenyltrimethylammoniumbromid dibromide, benzyltrimethylammonium-tribromid, triphenylphosphine dibromide, etc. in a solvent such as DCM, chloroform, THF, diethyl ether, methanol, ethanol, etc., and mixtures thereof.

Structure 11

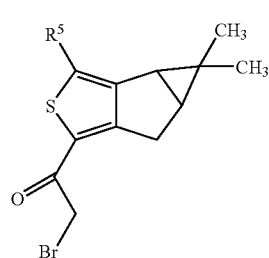

Structure 12

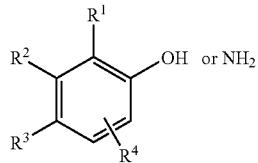

The compounds of Structure 1 wherein $R^5$ represents an ethyl group may also be prepared from a compound of Structure 1 wherein $R^5$ represents hydrogen by reacting the latter compound with an excess of a strong base such as n-BuLi, tert.-BuLi, LDA etc. in a solvent such as THF, diethyl ether, etc. followed by the appropriate alkylating agent (e.g. ethyl iodide). A compound of Structure 1 wherein $R^5$ represents hydrogen may be prepared from a compound of Structure 9 wherein $R^5$ represents hydrogen in analogy to the literature cited above.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 m, 120A, gradient: 5-95% acetonitrile in water, 1 min, with 0.04% trifluoroacetic acid, flow: 4.5 ml/min), $t_R$ is given in min; by TLC (Thin Layer Chromatography-plates from Merck, Silica gel 60 $F_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

| Abbreviations (as used herein) | |
|---|---|
| abs. | absolute |
| aq. | aqueous |
| atm | atmosphere |
| BOC-anhydride | di-tert. butyl dicarbonate |
| BOP | (benzotriazol-1-yloxy)-tris-(dimethylamino)-phosphonium hexafluorophosphate |
| BOP-Cl | bis-(2-oxo-3-oxazolidinyl)-phosphinic acid chloride |
| BSA | bovine serum albumin |
| Bu | butyl |
| CC | column chromatography |
| DBU | 1,8-diazabicyclo[5.4.0]undec-7-ene |
| DCC | dicyclohexyl carbodiimide |
| DCM | dichloromethane |
| DIPEA | diisopropylethylamine |
| DMF | dimethylformamide |
| DMSO | dimethylsulfoxide |
| EA | ethyl acetate |
| EDC | N-(3-dimethylaminopropyl)-N'-ethyl-carbodiimide |
| Et | ethyl |
| h | hour(s) |
| HOBt | 1-hydroxybenzotriazole |
| HPLC | high performance liquid chromatography |
| LC-MS | liquid chromatography - mass spectrometry |

| Abbreviations (as used herein) | |
|---|---|
| LDA | lithium diisopropylamide |
| Me | methyl |
| min | minute(s) |
| MPLC | medium pressure liquid chromatography |
| prep. | preparative |
| PyBOP | benzotriazol-1-yl-oxy-tris-pyrolidino-phosphonium-hexafluorophosphat |
| TBTU | 2-(1H-benzotriazole-1-yl)-1,2,3,3-tetramethyluronium tetrafluoroborate |
| TBME | tert.-butylmethyl ether |
| TFA | trifluoroacetic acid |
| THF | tetrahydrofuran |
| rt | room temperature |
| sat. | saturated |
| S1P | sphingosine 1-phosphate |
| $t_R$ | retention time |

(1aS,5aR)-1,1,2-Trimethyl-1,1a,5,5a-tetrahydro-3-thia-cyclopropa[a]pentalene-4-carboxylic acid ethyl ester (Example of a compound of Structure 7)

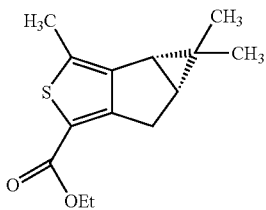

a) NaH (7.0 g, 60% dispersion in mineral oil, 175 mmol) is washed with pentane (100 mL) before it is suspended in THF (400 mL). The suspension is cooled to 0° C. and a solution of ethyl 2-mercaptoacetate (12.62 g, 105 mmol) in THF (50 mL) is added over a period of 20 min. The temperature of the reaction is maintained at 5-10° C. Upon completion of the addition, the cooling is removed and stirring is continued for 30 min. A solution of (1S,5R)-2-(1-chloro-(E)-ethylidene)-6,6-dimethyl-bicyclo[3.1.0]hexan-3-one (S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) (12.93 g, 70 mmol) in THF (50 mL) is added to the suspension and the resulting mixture is stirred for 1.5 h at rt. The mixture is filtered, the filtrate is concentrated to about 100 mL, diluted with 1 M aq. NaOH (100 mL) and extracted twice with DCM (150 mL). The extracts are dried over $Na_2SO_4$ and evaporated to furnish a crude E/Z mixture of {1-[(1S,5R)-6,6-dimethyl-3-oxo-bicyclo[3.1.0]hexylidene]-ethylsulfanyl}-acetic acid ethyl ester (18.2 g) as a brown oil. LC-MS: $t_R$=1.00 min, [M+1]$^+$=269.13. $^1$H NMR (CDCl$_3$): δ 4.22 (q, J=7.0 Hz, 2H both isomers), 3.67 (d, J=15.8 Hz, 1H major isomer), 3.63 (d, J=15.8 Hz, 1H minor isomer), 3.58 (d, J=15.8 Hz, 1H major isomer), 3.54 (d, J=15.8 Hz, 1H, minor isomer), 2.67 (dd, J=6.4, 19.4 Hz, 1H minor isomer), 2.60 (dd, J=7.0, 19.4 Hz, 1H major isomer), 2.58 (s, 3H minor isomer), 2.52 (s, 3H major isomer), 2.36-2.32 (m, 1H major isomer), 2.30-2.26 (m, 1H major isomer, 1H minor isomer), 2.18 (d, J=7.0 Hz, 1H minor isomer), 2.00 (d, J=7.0 Hz, 1H major isomer), 1.95 (d, J=7.6 Hz, 1H minor isomer), 1.30 (t, J=7.0 Hz, 3H major isomer), 1.28 (t, J=7.0 Hz, 3H minor isomer), 1.18 (s, 3H major isomer), 1.15 (s, 3H minor isomer), 0.89 (s, 3H minor isomer), 0.85 (s, 3H major isomer).

b) A solution of Na (1.70 g, 74.8 mmol) in abs. ethanol (75 mL) is heated to 60° C. before it is treated with a solution of crude {1-[(1S,5R)-6,6-dimethyl-3-oxo-bicyclo[3.1.0]hex-(2Z)-ylidene]-ethylsulfanyl}-acetic acid ethyl ester (18.2 g, 68.0 mmol) in abs. ethanol (200 mL). The mixture is stirred at 75° C. for 20 min, then cooled to rt, diluted with 0.5 M aq. NaOH (500 mL) and extracted with DCM (450+200 mL). The combined extracts are dried over $Na_2SO_4$, filtered and the solvent is removed in vacuo. This yields crude (1aS,5aR)-1,1,2-trimethyl-1,1a,5,5a-tetrahydro-3-thia-cyclopropa[a]pentalene-4-carboxylic acid ethyl ester (10.5 g) as a yellow oil of 87% purity (LC-MS, UV 280 nm). LC-MS: $t_R$=1.11 min, [M+1]$^+$=251.14; $^1$H NMR (CDCl$_3$): δ 4.26 (q, J=7.0 Hz, 2H), 2.95 (dp, $J_d$=18.8 Hz, $J_p$=3.5 Hz, 1H), 2.79 (d, J=19.3, 1H), 2.37 (s, 3H), 1.89-1.84 (m, 2H), 1.34 (t, J=7.0 Hz, 3H), 1.12 (s, 3H), 0.72 (s, 3H).

(1aS,5aR)-1,1,2-Trimethyl-1,1a,5,5a-tetrahydro-3-thia-cyclopropa[a]pentalene-4-carboxylic acid (Example of a compound of Structure 1)

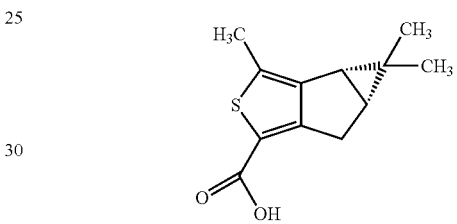

To a solution of crude (1aS,5aR)-1,1,2-trimethyl-1,1a,5,5a-tetrahydro-3-thia-cyclopropa[a]pentalene-4-carboxylic acid ethyl ester (10.3 g, 41.2 mmol) in ethanol (200 mL) a solution of 2N aq. LiOH (300 mL) is added. The resulting mixture is stirred at 70° C. for 1 h, cooled to rt and diluted with water (250 mL). The aq. solution is extracted three times with DCM (125 mL) before it is acidified to pH 3 by adding citric acid. The acidified solution is extracted twice with DCM (2×250 mL), These second extracts are combined, dried over $Na_2SO_4$, filtered and evaporated to leave (1aS,5aR)-1,1,2-trimethyl-1,1a,5,5a-tetrahydro-3-thia-cyclopropa[a]pentalene-4-carboxylic acid (7.0 g) as a yellow solid. LC-MS: $t_R$=0.95 min, [M+1]$^+$=223.00. $^1$H NMR (CDCl$_3$): δ 3.04-2.92 (m, 1H), 2.83 (d, J=19.3 Hz, 1H), 2.39 (s, 3H), 1.91-1.87 (m, 2H), 1.13 (s, 3H), 0.73 (s, 3H).

(1aS,5aR)-1,1,2-Trimethyl-1,1a,5,5a-tetrahydro-3-thia-cyclopropa[a]pentalene-4-carboxylic acid methoxy-methyl-amide (Example of a compound of Structure 3)

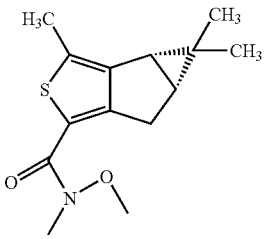

A mixture of N,O-dimethylhydroxylamine hydrochloride (158 mg, 1.62 mmol) and (1aS,5aR)-1,1,2-trimethyl-1,1a,5,5a-tetrahydro-3-thia-cyclopropa[a]pentalene-4-carboxylic acid (300 mg, 1.35 mmol) in DCM (30 mL) and acetonitrile (10 mL) is treated with diisopropylethylamine (209 mg, 1.62 mmol). To the resulting clear solution EDC.HCl (311 mg, 1.62 mmol) is added and the mixture is stirred at rt for 18 h before it is diluted with DCM (50 mL) and washed with 1 N aq. HCl (2×50 ml) and 1 N aq. NaOH (50 mL). The organic layer is dried over $Na_2SO_4$ and evaporated. The crude product is purified by prep. HPLC (Phenomenex AQUA 30×75 mm, gradient of 20-95% acetonitrile in water containing 0.5% formic acid) to furnish (1aS,5aR)-1,1,2-trimethyl-1,1a,5,5a-tetrahydro-3-thia-cyclopropa[a]pentalene-4-carboxylic acid methoxy-methyl-amide (200 mg) as a pale yellow solid. LC-MS: $t_R$=1.02 min, $[M+1]^+$=266.04. $^1$H NMR ($CDCl_3$): δ 3.75 (s, 3H), 3.29 (s, 3H), 3.12-3.01 (m, 1H), 2.93 (d, J=19.0 Hz, 1H), 2.38 (s, 3H), 1.90-1.82 (m, 2H), 1.12 (s, 3H), 0.71 (s, 3H).

(1aS,5aR)-1-(1,1,2-Trimethyl-1,1a,5,5a-tetrahydro-3-thia-cyclopropa[a]pentalen-4-yl)-ethanone (Example of a compound of Structure 5)

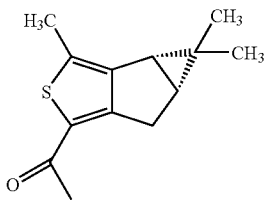

To a solution of (1aS,5aR)-1,1,2-trimethyl-1,1a,5,5a-tetrahydro-3-thia-cyclopropa[a]pentalene-4-carboxylic acid (220 mg, 1.00 mmol) in diethyl ether (10 mL) is added a solution of MeLi (1.6 M, 1.4 mL, 2.10 mmol) in diethyl ether at such a pace that the reaction mixture is refluxing gently. Upon completion of the addition stirring is continued at rt for 30 min. The reaction is quenched by adding sat. aq. $NH_4Cl$ (3 mL). The organic layer is separated, dried over $Na_2SO_4$ and the solvent is evaporated to give the title compound (165 mg) as a pale yellow oil. LC-MS: $t_R$=1.03 min, $[M+1]^+$=221.20; $^1$H NMR ($CDCl_3$): δ 3.00 (ddd, J=1.8, 4.7, 18.8 Hz, 1H), 2.80 (d, J=18.8 Hz, 1H), 2.38 (s, 6H), 1.93-1.90 (m, 2H), 1.14 (s, 3H), 0.74 (s, 3H).

2-Bromo-1-((1aS,5aR)-1,1,2-trimethyl-1,1a,5,5a-tetrahydro-3-thia-cyclopropa[a]pentalen-4-yl)-ethanone

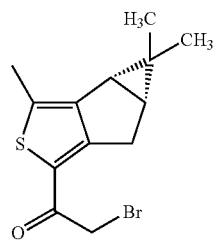

To a solution of (1aS,5aR)-1-(1,1,2-trimethyl-1,1a,5,5a-tetrahydro-3-thia-cyclopropa[a]pen-talen-4-yl)-ethanone (1.0 g, 4.5 mmol) in THF (50 mL) phenyltrimethylammonium bromide dibromide (2.05 g, 5.4 mmol) is added at 0° C. The mixture is stirred at rt for 3 h, filtered, and the solvent of the filtrate is evaporated. The crude product is purified by prep. HPLC (Grom-Sil 1200DS-4-HE, 30×75 mm, 10 µm, 20% to 95% acetonitrile in water containing 0.5% HCOOH) to give the title compound (800 mg) as a colourless oil; MS: $t_R$=1.07 min, $[M+1]^+$=299.11, $^1$H NMR ($CDCl_3$): δ 4.20-4.10 (m, 2H), 3.04 (dd, J=5.3, 18.8 Hz, 1H), 2.86 (d, J=18.8 Hz, 1H), 2.40 (s, 3H), 1.98-1.90 (m, 2H), 1.13 (s, 3H), 0.73 (s, 3H).

rac-(1S,5R)-2-[1-Chloro-eth-(E)-ylidene]-6,6-dimethyl-bicyclo[3.1.0]hexan-3-one (Example of a compound of Structure 9)

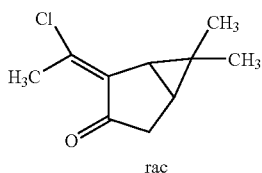

a) To a suspension of (+)-3-carene (82 g, 0.6 mol) and $CaCO_3$ (80 g, 0.8 mol) in water (300 mL) and dioxane (600 mL) is added N-bromosuccinimide (142 g, 0.8 mol). The mixture is stirred at rt for 1 h, diluted with water (1500 mL) and extracted with diethyl ether (500 mL). The organic extract is washed with water (3×1000 mL) and 5% aq. $Na_2S_2O_3$ (2×500 mL), and dried over $Na_2SO_4$. The solvent is removed under reduced pressure and the crude product is purified by column chromatography on silica gel eluting with hexane/EA 4:1 to yield (1S,3R,4R,6R)-4-bromo-3,7,7-trimethyl-bicyclo[4.1.0]heptan-3-ol (48.3 g) as a beige solid. $^1$H NMR ($CDCl_3$): δ 4.05 (dd, J=7.6, 10.6 Hz, 1H), 2.48-2.36 (m, 2H), 2.20 (dd, J=10.0, 14.7 Hz, 1H), 1.42-1.38 (m, 1H), 1.36 (s, 3H), 1.02 (s, 3H), 0.98 (s, 3H), 0.90-0.80 (m, 1H), 0.72-0.66 (m, 1H).

b) To a solution of (1S,3R,4R,6R)-4-bromo-3,7,7-trimethyl-bicyclo[4.1.0]heptan-3-ol (58.0 g, 0.25 mol) in water (120 mL) and dioxane (1600 mL) is added $Ag_2O$ (156.4 g, 0.675 mol). The resulting suspension is stirred at rt for 18 h before it is filtered over celite. The filtrate is evaporated under reduced pressure. The remaining solid is dissolved in diethyl ether (650 mL) and washed with water (2×1000 mL). The organic extract is dried over $Na_2SO_4$ and the solvent is removed in vacuo to furnish 1-((1S,3S,5R)-6,6-dimethyl-bicyclo[3.1.0]hex-3-yl)-ethanone (36.6 g) as a pale yellow oil. $^1$H NMR ($CDCl_3$): δ 2.83-2.70 (m, 1H), 2.14-2.03 (m, 5H), 1.82 (dd, J=10.0, 14.1 Hz, 2H), 1.16-1.13 (m, 2H), 0.95 (s, 6H).

c) To a solution of 1-((1S,3S,5R)-6,6-dimethyl-bicyclo[3.1.0]hex-3-yl)-ethanone (36.5 g, 0.24 mol) in DCM (700 mL) is added 70% m-chloroperbenzoic acid (77 g, 0.312 mol) in portions. The reaction mixture is stirred at rt for 36 h before it is washed with 0.2 N aq. NaOH (1000 mL). The wash solution is extracted back with DCM (2×300 mL). The combined organic extracts are dried over $MgSO_4$ and the solvent is removed in vacuo to furnish acetic acid (1S,3S,5R)-6,6-dimethyl-bicyclo[3.1.0]hex-3-yl ester (37.8 g) as a pale yellow oil. $^1$H NMR ($CDCl_3$): δ 4.94 (hept. J=3.5 Hz, 1H), 2.02-1.93 (m, 5H), 1.87-1.78 (m, 2H), 1.22-1.15 (m, 2H), 0.95 (s, 3H), 0.83 (s, 3H).

d) A solution of acetic acid (1S,3S,5R)-6,6-dimethyl-bicyclo[3.1.0]hex-3-yl ester (37.85 g, 225 mmol) in ethanol (700 mL) is treated with 2 N aq. LiOH (700 mL). The mixture is stirred at rt for 1 h, diluted with water (600 mL) and extracted with EA (2×150 mL). The combined organic extracts are dried over MgSO$_4$ and evaporated to give (1S,3S,5R)-6,6-dimethyl-bicyclo[3.1.0]hexan-3-ol (23.9 g) as a pale yellow oil. $^1$H NMR (CDCl$_3$): δ 4.23 (hept, J=2.9 Hz, 1H), 1.87-1.70 (m, 4H), 1.23-1.20 (m, 2H), 0.96 (s, 3H), 0.81 (s, 3H).

e) To a mixture of pyridine (80 mL) and DCM (720 mL) is added CrO$_3$ (50 g, 0.5 mol). The mixture is stirred for 5 min before (1S,3S,5R)-6,6-dimethyl-bicyclo[3.1.0]hexan-3-ol (11.5 g, 0.08 mol) is added. Stirring is continued at rt for 2.5 h. The mixture is decanted from an oily residue, diluted with DCM (100 mL) and washed with 2 N aq. HCl (3×80 mL) followed by sat. aq. NaHCO$_3$ solution (80 mL). The separated organic phase is dried over NaSO$_4$ and the solvent is removed in vacuo to give (1S,5R)-6,6-dimethyl-bicyclo[3.1.0]hexan-3-one as a pale yellow oil. $^1$H NMR (CDCl$_3$): δ 2.58-2.46 (m, 2H), 2.19-2.11 (m, 2H), 1.34-1.26 (m, 2H), 1.09 (s, 3H), 0.87 (s, 3H).

f) To a suspension of NaH (873 mg 55% dispersion in mineral oil, 20 mmol, washed with dioxane prior to use) in dioxane (15 mL) is added methyl acetate (2.22 g, 30 mmol). The suspension is stirred for 5 min at rt and a solution of (1S,5R)-6,6-dimethyl-bicyclo[3.1.0]hexan-3-one (1.24 g, 10 mmol) in dioxane (5 mL) is added. The reaction mixture is stirred at 65° C. overnight. The mixture is poured onto cold 10% aq. citric acid solution (75 mL) and extracted with DCM (3×75 mL). The organic extracts are washed with water, dried over MgSO$_4$ and evaporated to give crude racemic (1R,2R,5R)-2-acetyl-6,6-dimethyl-bicyclo[3.1.0]hexan-3-one (2.45 g, contains dioxane) as a dark yellow liquid. $^1$H NMR (CDCl$_3$): δ 2.61 (dd, J=7.3, 19.6 Hz, 1H), 2.34-2.20 (m, 1H), 2.01 (s, 3H), 1.72 (d, J=8.2 HZ, 1H), 1.40-1.20 (m, 2H), 1.09 (s, 3H), 0.81 (s, 3H).

g) A mixture of the above yellow liquid (1.66 g, 10 mmol), triphenylphosphine (4.53 g, 17 mmol), CCl$_4$ (5 mL) in chloroform (15 mL) is heated to 65° C. for 1 h. The mixture is concentrated and the remaining residue is stirred with pentane. The pentane is decanted, the remaining residue is once more treated with pentane. The pentane fractions are combined and concentrated to leave rac-(1S,5R)-2-[1-chloro-eth-(E)-ylidene]-6,6-dimethyl-bicyclo[3.1.0]hexan-3-one (1.9 g) as a brownish oil. This material is used in the next step without further purification. LC-MS: $t_R$=1.02 min.

rac-1-((1aS,5aR)-2-Ethyl-1,1-dimethyl-1,1a,5,5a-tetrahydro-3-thia-cyclopropa[a]pentalen-4-yl)-ethanone

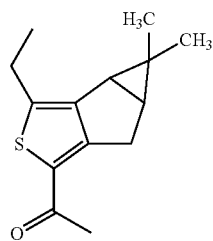

a) A solution of (1S,5R)-6,6-dimethyl-bicyclo[3.1.0] hexan-3-one (2.0 g, 16.1 mmol, step f above) in THF (20 mL) is treated with K. tert.-butylate (1.99 g, 17.7 mmol). The dark brown solution is stirred at rt for 30 min before ethyl propionate (18.5 mL, 161 mmol) is added. Stirring is continued at rt for 1 h. The mixture is diluted with 10% aq. citric acid and extracted with diethyl ether. The organic extract is washed with brine, dried over NaSO$_4$ and the solvent is evaporated to leave rac-(1S,5R)-6,6-dimethyl-2-propionyl-bicyclo[3.1.0] hexan-3-one (2.35 g) as a brown oil. LC-MS: $t_R$=0.99 min, [M+1]$^+$=181.29, $^1$H NMR (CDCl$_3$): δ 2.64 (dd, J=7.6, 20.0 Hz, 1H), 2.36-2.22 (m, 3H), 1.75 (d, J=7.6 Hz, 1H), 1.30-1.22 (m, 1H), 1.18 (t, J=7.6 Hz, 3H), 1.10 (s, 3H), 0.82 (s, 3H).

b) To a solution of rac-(1S,5R)-6,6-dimethyl-2-propionyl-bicyclo[3.1.0]hexan-3-one (14.37 g, 80 mmol) in chloroform (145 mL) and CCl$_4$ (53 mL), triphenylphosphine (41.8 g, 160 mmol) is added. The resulting solution is stirred at 60° C. for 75 min before a second portion of triphenylphosphine (4.2 g, 16 mmol) is added. Stirring is continued at 60° C. for 30 min. The solvent is evaporated and the residue is suspended in pentane. The pentane solution is decanted from the brown oily residue. The residue is once more treated with pentane. The combined pentane fractions are carefully evaporated to leave crude (1R,5S)-2-[1-chloro-propylidene]-6,6-dimethyl-bicyclo[3.1.0]hexan-3-one (11.0 g) as a yellow oil.

c) To a solution of (1R,5S)-2-[1-chloro-propylidene]-6,6-dimethyl-bicyclo[3.1.0]hexan-3-one (11.0 g, 55.4 mmol) in THF (40 mL) a solution of ethyl-2-mercaptoacetate (9.6 mL, 87.2 mmol) in a freshly prepared solution of Na (3.9 g, 170 mmol) in ethanol (95 mL) is added at 30° C. The reaction mixture is stirred at 30° C. for 2 h before it is diluted with EA and washed with 1 N aq. NaOH and brine. The organic extracts are dried over Na$_2$SO$_4$ and the solvent is removed in vacuo. The resulting brown oil (9.66 g) is dissolved in ethanol (365 mL) and diluted with 1 N aq. LiOH (365 mL). The mixture is refluxed for 1 h before the organic solvent is removed in vacuo. Solid material is filtered off and the filtrate is extracted twice with diethyl ether. The organic layer is extracted back with 1 N aq. LiOH and brine. The aq. extracts are acidified with aq. HCl (37%). The precipitate that formes is collected, washed with water followed by hexane, and dried under high vacuum to give rac-(1aS,5aR)-2-ethyl-1,1-dimethyl-1,1a,5,5a-tetrahydro-3-thia-cyclopropa[a]pentalene-4-carboxylic acid (3.6 g) as beige crystals. From the hexane washings a second crop (2.37 g) is obtained after evaporation of the solvent; LC-MS: $t_R$=0.99 min, [M+1]$^+$=237.24, $^1$H NMR (CDCl$_3$): δ 3.00 (dd, J=5.9, 19.3 Hz, 1H), 2.84-2.70 (m, 3H), 1.92-1.86 (m, 2H), 1.28 (t, J=7.0 Hz, 3H), 1.12 (s, 3H), 0.70 (s, 3H).

d) To a solution of rac-(1aS,5aR)-2-ethyl-1,1-dimethyl-1,1a,5,5a-tetrahydro-3-thia-cyclopropa[a]pentalene-4-carboxylic acid (5.9 g, 25.0 mmol) in diethyl ether (420 mL) MeLi (30 mL, 1.6 M solution in diethyl ether) is added at rt. The mixture is stirred at rt for 30 min before another portion of MeLi (6 mL) is added. Stirring is continued at rt for 1 h. The mixture is poured onto ice/water, the organic layer is separated, washed with 1 N aq. NaOH and brine, dried over Na$_2$SO$_4$, and filtered. The solvent is removed in vacuo and the crude product is purified by CC on silica gel eluting with hexane:EA 9:1 to give rac-1-((1aS,5aR)-2-ethyl-1,1-dimethyl-1,1a,5,5a-tetrahydro-3-thia-cyclopropa[a]pentalen-4-yl)-ethanone (3.7 g) as a pale yellow oil; LC-MS: $t_R$=1.07 min, [M+1]$^+$=235.31, $^1$H NMR (CDCl$_3$): δ 2.98 (dd, J=5.9, 18.8 HZ, 1H), 2.83-2.70 (m, 3H), 2.40 (s, 3H), 1.94-1.87 (m, 2H), 1.27 (t, J=7.6 Hz, 3H), 1.12 (s, 3H), 0.71 (s, 3H).

Example 1

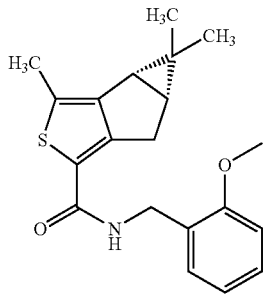

To a solution of (1aS,5aR)-1,1,2-trimethyl-1,1a,5,5a-tetrahydro-3-thia-cyclopropa[a]pentalene-4-carboxylic acid (Compound of Structure 1) (4.0 mg, 0.018 mmol), TBTU (7.1 mg, 0.022 mmol) and ethyl-diisopropylamine (8.4 mg, 0.065 mmol) in DMF (0.5 mL) is added a solution of 2-methoxy-benzylamine (3.3 mg, 0.022 mmol) in DMF (0.2 mL). The mixture is allowed to stand at rt for 1 h before it is subjected to purification by prep. HPLC (Water Xterra Prep. RpC18, 19×5 mm, 5 μm particle size, gradient: 20 to 95% acetonitrile in water containing 0.5% sat. ammonium hydroxide). This gives (1aS,5aR)-1,1,2-trimethyl-1,1a,5,5a-tetrahydro-3-thia-cyclopropa[a]pentalene-4-carboxylic acid 2-methoxy-benzylamide (4.8 mg) as a colourless lyophilisate. LC-MS: $t_R$=1.08 min, $[M+1]^+$=342.12.

Example 2

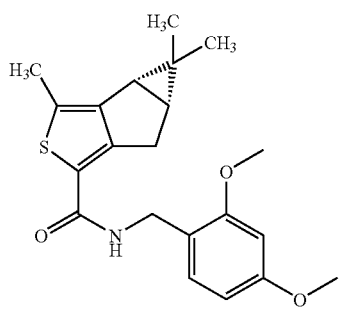

(1aS,5aR)-1,1,2-Trimethyl-1,1a,5,5a-tetrahydro-3-thia-cyclopropa[a]pentalene-4-carboxylic acid 2,4-dimethoxy-benzylamide (4.9 mg) is obtained as a colourless lyophilisate starting from (1aS,5aR)-1,1,2-trimethyl-1,1a,5,5a-tetrahydro-3-thia-cyclopropa[a]pentalene-4-carboxylic acid (Compound of Structure 1) (4.4 mg, 0.020 mmol) and 2,4-dimethoxy benzylamine (4.0 mg, 0.024 mmol) following the procedure given in Example 1. LC-MS: $t_R$=1.08 min, $[M+1]^+$=372.18.

Example 3

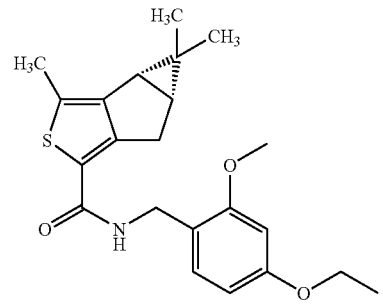

(1aS,5aR)-1,1,2-Trimethyl-1,1a,5,5a-tetrahydro-3-thia-cyclopropa[a]pentalene-4-carboxylic acid 4-ethoxy-2-methoxy-benzylamide (13.3 mg) is obtained as a colourless lyophilisate starting from (1aS,5aR)-1,1,2-trimethyl-1,1a,5,5a-tetrahydro-3-thia-cyclopropa[a]pentalene-4-carboxylic acid (Compound of Structure 1) (12.2 mg, 0.055 mmol) and 4-ethoxy-2-methoxy-benzylamine hydrochloride (12.0 mg, 0.055 mmol) following the procedure given in Example 1. LC-MS: $t_R$=1.10 min, $[M+1]^+$=386.15.

Example 4

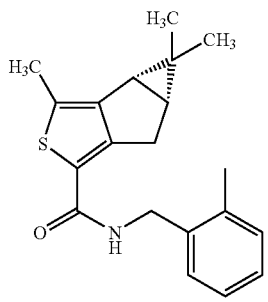

(1aS,5aR)-1,1,2-Trimethyl-1,1a,5,5a-tetrahydro-3-thia-cyclopropa[a]pentalene-4-carboxylic acid 2-methyl-benzylamide (4.5 mg) is obtained as a colourless lyophilisate starting from (1aS,5aR)-1,1,2-trimethyl-1,1a,5,5a-tetrahydro-3-thia-cyclopropa[a]pentalene-4-carboxylic acid (Compound of Structure 1) (4.0 mg, 0.018 mmol) and 2-methylbenzylamine (2.7 mg, 0.022 mmol) following the procedure given in Example 1. LC-MS: $t_R$=1.09 min, $[M+1]^+$=326.07.

Example 5

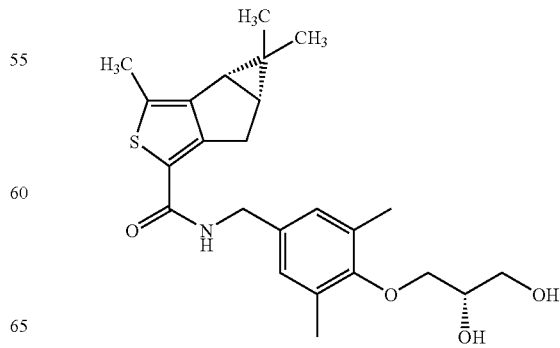

a) To a suspension of LiAlH$_4$ (1.51 g, 39.8 mmol) in diethyl ether (40 mL) a solution of 4-hydroxy-3,5-dimethylbenzonitrile (4.89 g, 33.2 mmol) in diethyl ether (20 mL) and THF (10 mL) is added dropwise at rt. The mixture is stirred at rt for 22 h before it is cooled with an ice-bath and carefully treated with water (10 mL), acidified with 25% aq. HCl and diluted with water (30 mL). The mixture is extracted with diethyl ether. The etheral extract is discarded. The aqueous phase is basified to pH~8 by adding solid NaHCO$_3$, saturated with NaCl, and extracted with diethyl ether followed by EA. The combined organic extracts are dried over MgSO$_4$ and evaporated to leave 4-aminomethyl-2,6-dimethyl-phenol (1.20 g) as a solid. LC-MS: t$_R$=0.51 min, [M+1]$^+$=152.19.

b) A solution of (1aS,5aR)-1,1,2-trimethyl-1,1a,5,5a-tetrahydro-3-thia-cyclopropa[a]pentalene-4-carboxylic acid (67 mg, 0.30 mmol), TBTU (106 mg, 0.33 mmol) and ethyl-diisopropylamine (169 μL, 0.99 mmol) in DMF (2 mL) is allowed to stand at rt for 10 min. A solution of 4-aminomethyl-2,6-dimethyl-phenol (45 mg, 0.30 mmol) in DMF (0.5 mL) is added and the mixture is allowed to stand at rt for 3 h. After the addition of formic acid (0.2 mL) the mixture is separated by HPLC to afford (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (100 mg) as a colourless oil. LC-MS: t$_R$=1.03 min, [M+1]$^+$=356.23.

c) To a solution of (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (8.9 mg, 0.025 mmol) in isopropanol (1 mL) is added 2 N aq. NaOH (100 μL), NaI (1 mg, 0.007 mmol) and (S)-3-chloro-propane-1,2-diol (11.1 mg, 0.1 mmol). The reaction mixture is heated to 90° C. and shaken for 8 h before it is cooled to rt. Formic acid (0.2 mL) is added and the reaction mixture is separated by prep. HPLC to give (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3,5-dimethyl-benzylamide (3.7 mg) as a colourless lyophilisate. LC-MS: t$_R$=0.94 min, [M+1]$^+$=430.27.

Example 6

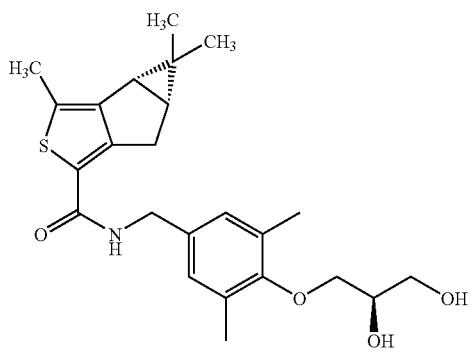

(1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3,5-dimethyl-benzylamide (3.1 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (8.9 mg, 0.025 mmol, Example 5, step b) and (R)-3-chloro-propane-1,2-diol (11.1 mg, 0.1 mmol) following the procedure given in Example 5, step c. LC-MS: t$_R$=0.94 min, [M+1]$^+$=430.27.

Example 7

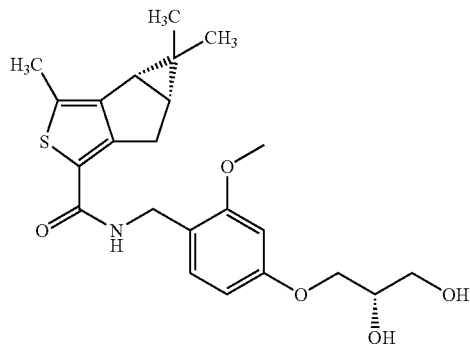

a) A solution of (1aS,5aR)-1,1,2-trimethyl-1,1a,5,5a-tetrahydro-3-thia-cyclopropa[a]pentalene-4-carboxylic acid (78 mg, 0.35 mmol), TBTU (124 mg, 0.39 mmol) and ethyl-diisopropylamine (264 μL, 1.54 mmol) in DMF (1.5 mL) is allowed to stand at rt for 10 min before a solution of 4-aminomethyl-3-methoxy-phenol (73 mg, 0.39 mmol, prepared starting from 4-hydroxy-2-methoxy-benzaldehyde in analogy to literature procedures: *J. Org. Chem.* 53 (1988), 1064-1071; J. Chem. Soc. Perkin Trans. 1, 1992, 1709-1719) and ethyl-diisopropylamine (64 μL, 0.39 mmol) in DMF (0.75 mL) is added. The reaction mixture is allowed to stand for 3 h before it is separated by prep. HPLC. This yields (1aS,5aR)-1,1,2-trimethyl-1,1a,5,5a-tetrahydro-3-thia-cyclopropa[a]pentalene-4-carboxylic acid 4-hydroxy-2-methoxy-benzylamide (105 mg) as a colourless lyophilisate. LC-MS: t$_R$=0.99 min, [M+1]$^+$=358.13.

b) (1aS,5aR)-1,1,2-Trimethyl-1,1a,5,5a-tetrahydro-3-thia-cyclopropa[a]pentalene-4-carboxylic acid 4-((S)-2,3-dihydroxy-propoxy)-2-methoxy-benzylamide (5.8 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-methoxy-benzylamide (10.0 mg, 0.028 mmol) and (S)-3-chloro-propane-1,2-diol (12.4 mg, 0.11 mmol) following the procedure given in Examples 5, step c. LC-MS: t$_R$=0.92 min, [M+1]$^+$=432.14; $^1$H NMR (CDCl$_3$): δ 7.20 (d, J=8.2 Hz, 1H), 6.49 (d, J=2.3 Hz, 1H), 6.43 (dd, J=2.3, 8.2 Hz, 1H), 6.16 (t br, J=5.6 Hz, 1H), 4.47 (d, J=5.9 Hz, 2H), 4.15-4.06 (m, 1H), 4.05-4.00 (m, 2H), 3.87 (s, 3H), 3.75 (dd, J=5.3, 11.1 Hz, 1H), 2.90 (dd, J=5.3, 17.6 Hz, 1H), 2.69 (d, J=17.6 Hz, 1H), 2.35 (s, 3H), 2.09 (s br, 2H), 1.91-1.85 (m, 2H), 1.11 (s, 3H), 0.72 (s, 3H).

Example 8

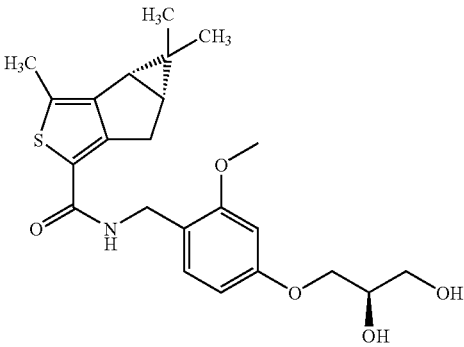

(1aS,5aR)-1,1,2-Trimethyl-1,1a,5,5a-tetrahydro-3-thia-cyclopropa[a]pentalene-4-carboxylic acid 4-((R)-2,3-dihydroxy-propoxy)-2-methoxy-benzylamide (4.6 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-methoxy-benzylamide (10.0 mg, 0.028 mmol, Example 7, step a) and (R)-3-chloro-propane-1,2-diol (12.4 mg, 0.11 mmol) following the procedure given in Example 5, step c. LC-MS: $t_R$=0.92 min, $[M+1]^+$=432.18.

Example 9

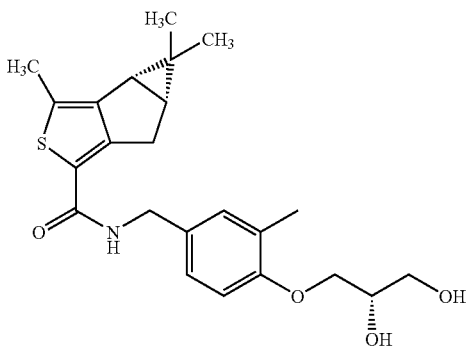

a) A solution of (1aS,5aR)-1,1,2-trimethyl-1,1a,5,5a-tetrahydro-3-thia-cyclopropa[a]pentalene-4-carboxylic acid (111 mg, 0.50 mmol), TBTU (177 mg, 0.55 mmol) and ethyl-diisopropylamine (282 μL, 1.65 mmol) in DMF (15 mL) is allowed to stand at rt for 20 min. A solution of 4-aminomethyl-2-methyl-phenol hydrochloride (96 mg, 0.55 mmol) and ethyl-diisopropylamine (94 μL, 0.55 mmol) in DMF (1.5 mL) is added and the mixture is allowed to stand at rt for 3 h. After the addition of formic acid (0.2 mL), the mixture is separated by HPLC to afford (1aS,5aR)-1,1,2-trimethyl-1,1a,5,5a-tetrahydro-3-thia-cyclopropa[a]pentalene-4-carboxylic acid 4-hydroxy-3-methyl-benzylamide (86 mg) as a colourless oil. LC-MS: $t_R$=0.99 min, $[M+1]^+$=342.17.

b) (1aS,5aR)-1,1,2-Trimethyl-1,1a,5,5a-tetrahydro-3-thia-cyclopropa[a]pentalene-4-carboxylic acid 4-((S)-2,3-dihydroxy-propoxy)-3-methyl-benzylamide (1.9 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3-methyl-benzylamide (7.8 mg, 0.023 mmol) and (S)-3-chloro-propane-1,2-diol (10.2 mg, 0.092 mmol) following the procedure given in Example 5, step c. LC-MS: $t_R$=0.93 min, $[M+1]^+$=416.25.

Example 10

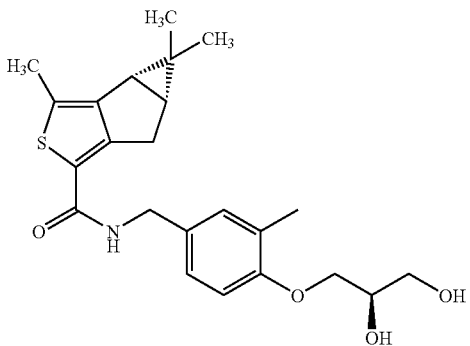

(1aS,5aR)-1,1,2-Trimethyl-1,1a,5,5a-tetrahydro-3-thia-cyclopropa[a]pentalene-4-carboxylic acid 4-((R)-2,3-dihydroxy-propoxy)-3-methyl-benzylamide (2.4 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-methoxy-benzylamide (7.8 mg, 0.023 mmol, Example 9, step a) and (R)-3-chloro-propane-1,2-diol (10.2 mg, 0.092 mmol) following the procedure given in Example 5, step c. LC-MS: $t_R$=0.93 min, $[M+1]^+$=416.30.

Example 11

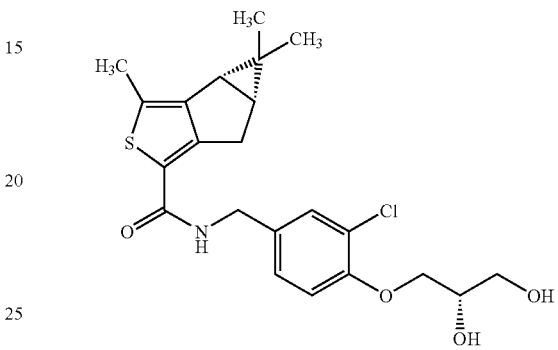

a) A solution of (1aS,5aR)-1,1,2-trimethyl-1,1a,5,5a-tetrahydro-3-thia-cyclopropa[a]pentalene-4-carboxylic acid (111 mg, 0.50 mmol), TBTU (177 mg, 0.55 mmol) and ethyl-diisopropylamine (282 μL, 1.65 mmol) in DMF (15 mL) is allowed to stand at rt for 20 min. A solution of 4-aminomethyl-2-chloro-phenol hydrochloride (104 mg, 0.55 mmol) and ethyl-diisopropylamine (94 μL, 0.55 mmol) in DMF (1.5 mL) is added and the mixture is allowed to stand at rt for 3 h. After the addition of formic acid (0.2 mL), the mixture is separated by HPLC to afford (1aS,5aR)-1,1,2-trimethyl-1,1a,5,5a-tetrahydro-3-thia-cyclopropa[a]pentalene-4-carboxylic acid 4-hydroxy-3-chloro-benzylamide (114 mg) as a colourless oil. LC-MS: $t_R$=1.00 min, $[M+1]^+$=362.14.

b) (1aS,5aR)-1,1,2-Trimethyl-1,1a,5,5a-tetrahydro-3-thia-cyclopropa[a]pentalene-4-carboxylic acid 4-((S)-2,3-dihydroxy-propoxy)-3-chloro-benzylamide (1.5 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3-chloro-benzylamide (8.3 mg, 0.023 mmol) and (S)-3-chloro-propane-1,2-diol (10.2 mg, 0.092 mmol) following the procedure given in Example 5, step c. LC-MS: $t_R$=0.94 min, $[M+1]^+$=436.20.

Example 12

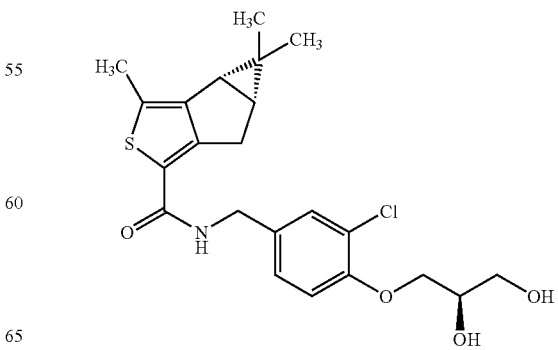

(1aS,5aR)-1,1,2-Trimethyl-1,1a,5,5a-tetrahydro-3-thia-cyclopropa[a]pentalene-4-carboxylic acid 4-((R)-2,3-dihydroxy-propoxy)-3-chloro-benzylamide (1.6 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3-chloro-benzylamide (8.3 mg, 0.023 mmol, Example 11, step a) and (R)-3-chloro-propane-1,2-diol (10.2 mg, 0.092 mmol) following the procedure given in Example 5, step c. LC-MS: $t_R$=0.94 min, $[M+1]^+$=436.19.

Example 13

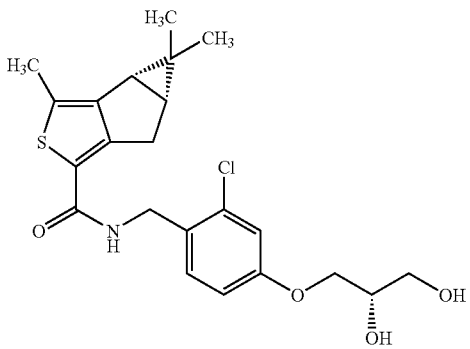

a) A solution of (1aS,5aR)-1,1,2-trimethyl-1,1a,5,5a-tetrahydro-3-thia-cyclopropa[a]pentalene-4-carboxylic acid (111 mg, 0.50 mmol), TBTU (177 mg, 0.55 mmol) and ethyl-diisopropylamine (282 µL, 1.65 mmol) in DMF (15 mL) is allowed to stand at rt for 20 min. A solution of 4-aminomethyl-3-chloro-phenol hydrochloride (104 mg, 0.55 mmol) and ethyl-diisopropylamine (94 mL, 0.55 mmol) in DMF (1.5 mL) is added and the mixture is allowed to stand at rt for 3 h. After the addition of formic acid (0.2 mL), the mixture is separated by HPLC to afford (1aS,5aR)-1,1,2-trimethyl-1,1a,5,5a-tetrahydro-3-thia-cyclopropa[a]pentalene-4-carboxylic acid 4-hydroxy-2-chloro-benzylamide (51 mg) as a colourless oil. LC-MS: $t_R$=1.01 min, $[M+1]^+$=362.13.

b) (1aS,5aR)-1,1,2-Trimethyl-1,1a,5,5a-tetrahydro-3-thia-cyclopropa[a]pentalene-4-carboxylic acid 4-((S)-2,3-dihydroxy-propoxy)-2-chloro-benzylamide (1.6 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (8.3 mg, 0.023 mmol) and (S)-3-chloro-propane-1,2-diol (10.2 mg, 0.092 mmol) following the procedure given in Example 5, step c. LC-MS: $t_R$=0.95 min, $[M+1]^+$=436.19.

Example 14

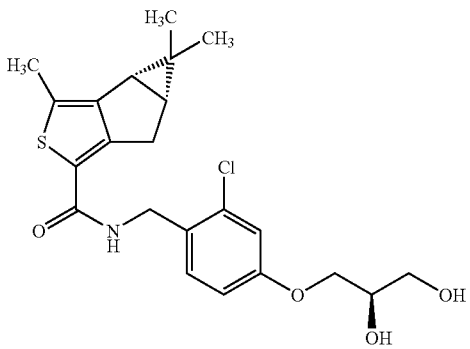

(1aS,5aR)-1,1,2-Trimethyl-1,1a,5,5a-tetrahydro-3-thia-cyclopropa[a]pentalene-4-carboxylic acid 4-((R)-2,3-dihydroxy-propoxy)-2-chloro-benzylamide (1.5 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (8.3 mg, 0.023 mmol, Example 13, step a) and (R)-3-chloro-propane-1,2-diol (10.2 mg, 0.092 mmol) following the procedure given in Example 5, step c. LC-MS: $t_R$=0.95 min, $[M+1]^+$=436.17.

Example 15

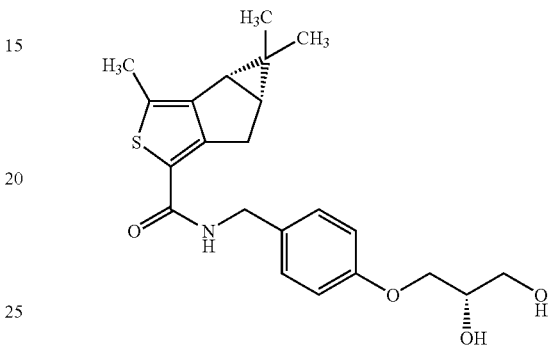

a) A solution of (1aS,5aR)-1,1,2-trimethyl-1,1a,5,5a-tetrahydro-3-thia-cyclopropa[a]pentalene-4-carboxylic acid (111 mg, 0.50 mmol), TBTU (177 mg, 0.55 mmol) and ethyl-diisopropylamine (282 µL, 1.65 mmol) in DMF (15 mL) is allowed to stand at rt for 20 min. A solution of 4-aminomethyl-phenol hydrochloride (88 mg, 0.55 mmol) and ethyl-diisopropylamine (94 µL, 0.55 mmol) in DMF (1.5 mL) is added and the mixture is allowed to stand at rt for 3 h. After the addition of formic acid (0.2 mL), the mixture is separated by HPLC to afford (1aS,5aR)-1,1,2-trimethyl-1,1a,5,5a-tetrahydro-3-thia-cyclopropa[a]pentalene-4-carboxylic acid 4-hydroxy-benzylamide (45 mg) as a colourless oil. LC-MS: $t_R$=0.96 min, $[M+1]^+$=328.17.

b) (1aS,5aR)-1,1,2-Trimethyl-1,1a,5,5a-tetrahydro-3-thia-cyclopropa[a]pentalene-4-carboxylic acid 4-((S)-2,3-dihydroxy-propoxy)-benzylamide (2.1 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-benzylamide (7.5 mg, 0.023 mmol) and (S)-3-chloro-propane-1,2-diol (10.2 mg, 0.092 mmol) following the procedure given in Example 5, step c. LC-MS: $t_R$=0.91 min, $[M+1]^+$=402.25.

Example 16

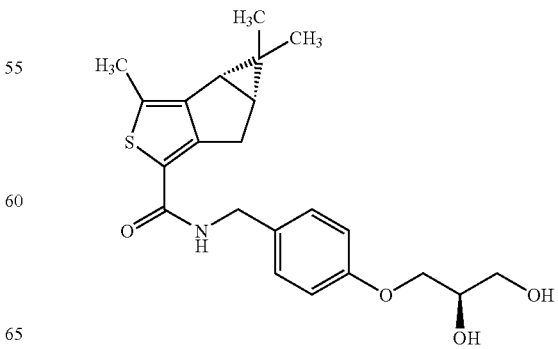

(1aS,5aR)-1,1,2-Trimethyl-1,1a,5,5a-tetrahydro-3-thia-cyclopropa[a]pentalene-4-carboxylic acid 4-((R)-2,3-dihydroxy-propoxy)-benzylamide (2.4 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (7.5 mg, 0.023 mmol, Example 15, step a) and (R)-3-chloro-propane-1,2-diol (10.2 mg, 0.092 mmol) following the procedure given in Example 5, step c. LC-MS: $t_R$=0.90 min, [M+1]$^+$=402.20.

Example 17

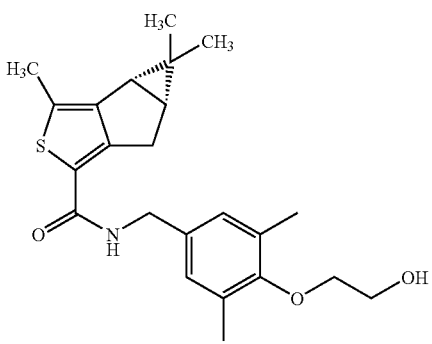

To a solution of (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (100 mg) (8.9 mg, 0.025 mmol) in isopropanol (1 mL) is added 2 N aq. NaOH (100 µL), NaI (1 mg, 0.007 mmol) and 2-bromo-ethanol (12.5 mg, 0.1 mmol). The reaction mixture is heated to 90° C. and shaken for 8 h before it is cooled to rt. Formic acid (0.2 mL) is added and the reaction mixture is separated by prep. HPLC to give (1aS,5aR)-1,1,2-trimethyl-1,1a,5,5a-tetrahydro-3-thia-cyclopropa[a]pentalene-4-carboxylic acid 4-(2-hydroxy-ethoxy)-3,5-dimethyl-benzylamide (5.4 mg) as a colourless lyophilisate. LC-MS: $t_R$=1.00 min, [M+1]$^+$=400.26.

Example 18

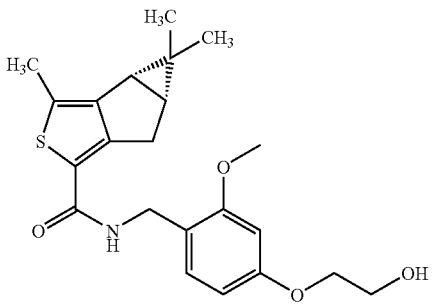

a) To a solution of 4-aminomethyl-3-methoxy-phenol (5.0 g, 26.5 mmol, prepared starting from 4-hydroxy-2-methoxy-benzaldehyde in analogy to literature procedures: *J. Org. Chem.* 53 (1988), 1064-1071; J. Chem. Soc. Perkin Trans. 1, 1992, 1709-1719) in methanol (140 mL) and 2 N aq. NaOH (70 mL) is added BOC-anhydride (8.7 g, 39.8 mmol). The mixture is stirred at rt for 2 h before further BOC-anhydride (5.8 g, 26.5 mmol) is added. Stirring is continued for 30 min and another portion of BOC-anhydride (5.8 g, 26.5 mmol) is added. The mixture is stirred for 30 min. The organic solvent is removed in vacuo, the remaining solution is diluted with 2 N aq. NaOH and extracted with DCM. The aq. phase is neutralised to pH 7 by adding 1 N aq. HCl and extracted with DCM (3×200 mL). These second organic extracts are combined, dried over Na$_2$SO$_4$, filtered and evaporated to give (4-hydroxy-2-methoxy-benzyl)-carbamic acid tert-butyl ester (2.9 g) as a beige solid. LC-MS: $t_R$=1.20 min, [M+1]$^+$=254.08; $^1$H NMR (D$_6$-DMSO): δ 9.24 (s, 1H), 6.95-6.85 (m, 2H), 6.33 (d, J=2.3 Hz, 1H), 6.26 (dd, J=2.3, 7.6, 1H), 3.95 (d, J=5.9 Hz, 2H), 3.69 (s, 3H), 1.37 (s, 9H).

b) To a stirred solution of (4-hydroxy-2-methoxy-benzyl)-carbamic acid tert-butyl ester (22.8 mg, 0.09 mmol) in 2-propanol (1 mL) and 2 N aq. NaOH (0.15 mL) is added 2-bromoethanol (22.5 mg, 0.18 mmol). The reaction mixture is heated to 85° C. and stirred for 8 h. The mixture is cooled to rt and subjected to prep. HPLC purification to give [4-(2-hydroxy-ethoxy)-2-methoxy-benzyl]-carbamic acid tert-butyl ester (10.3 mg) as a colourless oil. LC-MS: $t_R$=0.85 min, [M+1]$^+$=298.07.

c) The above [4-(2-hydroxy-ethoxy)-2-methoxy-benzyl]-carbamic acid tert-butyl ester (10.3 mg, 0.35 mmol) is treated with 37% aq. HCl (0.1 mL) and acetic acid (1 mL) for 1.5 h at rt. The solvents are removed by lyophilisation. The residue is dissolved in 2 N aq. NaOH (1 mL) and ethanol (0.25 mL) and heated to 80° C. for 1 h. The mixture is cooled to rt and extracted twice with EA. The organic extracts are combined, dried over Na$_2$SO$_4$, filtered and evaporated to give 2-(4-aminomethyl-3-methoxy-phenoxy)-ethanol (6.4 mg) as a beige oil. LC-MS: $t_R$=0.58 min, [M+1]$^+$=198.11.

d) A solution of (1aS,5aR)-1,1,2-trimethyl-1,1a,5,5a-tetrahydro-3-thia-cyclopropa[a]pentalene-4-carboxylic acid (7.8 mg, 0.035 mmol), TBTU (11.2 mg, 0.035 mmol) and ethyl-diisopropylamine (18.0 µL, 0.105 mmol) in DMF (1 mL) is allowed to stand at rt for 30 min. The solution is added to 2-(4-aminomethyl-3-methoxy-phenoxy)-ethanol (6.4 mg, 0.035 mmol) and the mixture is allowed to stand at rt for 1 h. The mixture is separated by prep. HPLC to afford (1aS,5aR)-1,1,2-trimethyl-1,1a,5,5a-tetrahydro-3-thia-cyclopropa[a]pentalene-4-carboxylic acid 4-(2-hydroxy-ethoxy)-2-methoxy-benzylamide (7.6 mg) as a colourless lyophilisate. LC-MS: $t_R$=0.98 min, [M+1]$^+$=402.16.

Example 19

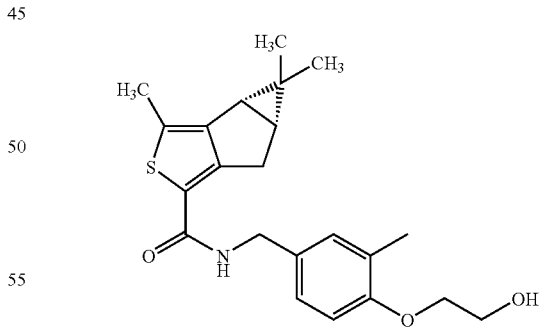

(1aS,5aR)-1,1,2-Trimethyl-1,1a,5,5a-tetrahydro-3-thia-cyclopropa[a]pentalene-4-carboxylic acid 4-(2-hydroxy-ethoxy)-3-methyl-benzylamide (1.9 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3-methyl-benzylamide (7.9 mg, 0.023 mmol, Example 9, step a) and 2-bromoethanol (11.5 mg, 0.092 mmol) following the procedure given in Example 5, step c. LC-MS: $t_R$=0.99 min, [M+1]$^+$=386.27.

Example 20

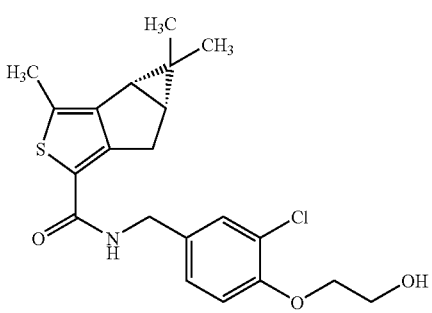

(1aS,5aR)-1,1,2-Trimethyl-1,1a,5,5a-tetrahydro-3-thia-cyclopropa[a]pentalene-4-carboxylic acid 4-(2-hydroxy-ethoxy)-3-chloro-benzylamide (1.2 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3-chloro-benzylamide (8.3 mg, 0.023 mmol, Example 11, step a) and 2-bromoethanol (11.5 mg, 0.092 mmol) following the procedure given in Example 5, step c. LC-MS: $t_R$=1.00 min, $[M+1]^+$=406.24.

Example 21

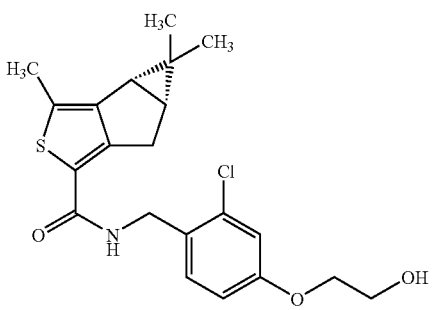

(1aS,5aR)-1,1,2-Trimethyl-1,1a,5,5a-tetrahydro-3-thia-cyclopropa[a]pentalene-4-carboxylic acid 4-(2-hydroxy-ethoxy)-2-chloro-benzylamide (1.3 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (8.3 mg, 0.023 mmol, Example 13, step a) and 2-bromoethanol (11.5 mg, 0.092 mmol) following the procedure given in Example 5, step c. LC-MS: $t_R$=1.01 min, $[M+1]^+$=406.18.

Example 22

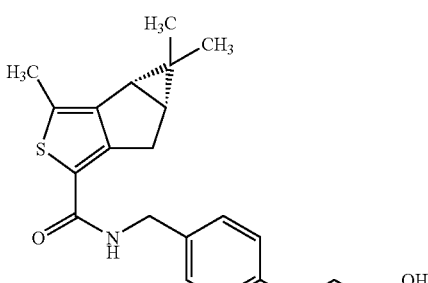

(1aS,5aR)-1,1,2-Trimethyl-1,1a,5,5a-tetrahydro-3-thia-cyclopropa[a]pentalene-4-carboxylic acid 4-(2-hydroxy-ethoxy)-benzylamide (2.2 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-benzylamide (7.5 mg, 0.023 mmol, Example 15, step a) and 2-bromoethanol (11.5 mg, 0.092 mmol) following the procedure given in Example 5, step c. LC-MS: $t_R$=0.96 min, $[M+1]^+$=372.20.

Example 23

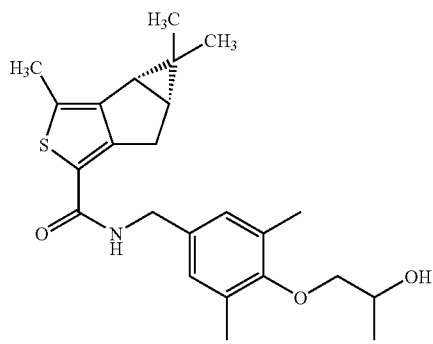

(1aS,5aR)-1,1,2-Trimethyl-1,1a,5,5a-tetrahydro-3-thia-cyclopropa[a]pentalene-4-carboxylic acid 4-((R/S)-2-hydroxy-propoxy)-3,5-dimethyl-benzylamide (5.7 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (8.9 mg, 0.025 mmol, Example 5, step b) and (rac)-1-bromo-propan-2-ol (13.9 mg, 0.1 mmol) following the procedure given in Example 5, step c. LC-MS: $t_R$=1.03 min, $[M+1]^+$=414.26.

Example 24

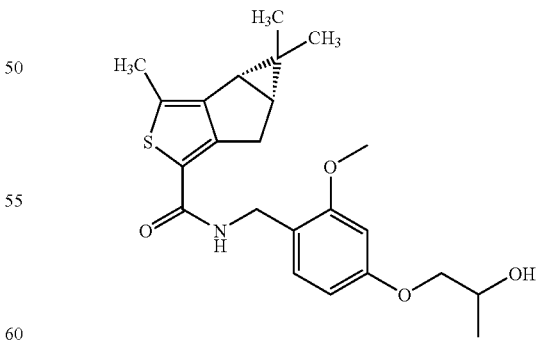

a) (rac)-1-(4-Aminomethyl-3-methoxy-phenoxy)-propan-2-ol is prepared starting from 4-aminomethyl-3-methoxy-phenol and (rac)-1-bromo-propan-2-ol in analogy to the procedures given in Example 18, steps a to c. LC-MS: $t_R$=0.66 min, $[M+1]^+$=212.13.

b) A solution of (1aS,5aR)-1,1,2-trimethyl-1,1a,5,5a-tetrahydro-3-thia-cyclopropa[a]pentalene-4-carboxylic acid (9.6 mg, 0.043 mmol), TBTU (13.8 mg, 0.043 mmol) and ethyl-diisopropylamine (22 μL, 0.129 mmol) in DMF (1 mL) is allowed to stand at rt for 30 min. The solution is added to (rac)-1-(4-aminomethyl-3-methoxy-phenoxy)-propan-2-ol (9.1 mg, 0.043 mmol) and the mixture is allowed to stand at rt for 1 h. The mixture is separated by prep. HPLC to afford (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-2-methoxy-benzylamide (7.6 mg) as a colourless oil. LC-MS: $t_R$=0.98 min, [M+1]$^+$=402.16; $^1$H NMR (CDCl$_3$): δ 7.20 (d, J=8.2 Hz, 1H), 6.50 (d, J=2.3 Hz, 1H), 6.44 (d, J=8.2 Hz, 1H), 6.16 (t br, J=5.3 Hz, 1H), 4.47 (d, J=5.9 Hz, 2H), 3.93 (dd, J=2.9, 11.1 Hz, 1H), 3.87 (s, 3H), 3.82-3.72 (m, 1H), 2.90 (dd, J=5.3, 17.6 Hz, 1H), 2.69 (d, J=18.1 Hz, 1H), 2.35 (s, 3H), 1.92-1.85 (m, 2H), 1.30 (d, J=6.4 Hz, 3H), 1.11 (s, 3H), 0.72 (s, 3H).

Example 25

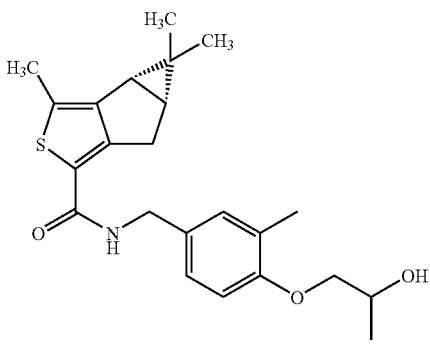

(1aS,5aR)-1,1,2-Trimethyl-1,1a,5,5a-tetrahydro-3-thia-cyclopropa[a]pentalene-4-carboxylic acid 4-((R/S)-2-hydroxy-propoxy)-3-methyl-benzylamide (1.7 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-3-methyl-benzylamide (7.9 mg, 0.023 mmol, Example 9, step a) and (rac)-1-bromo-propan-2-ol (12.8 mg, 0.092 mmol) following the procedure given in Example 5, step c. LC-MS: $t_R$=1.02 min, [M+1]$^+$=400.28.

Example 26

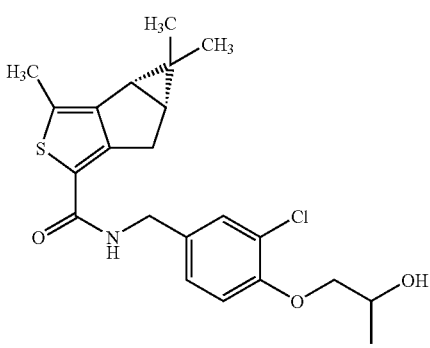

(1aS,5aR)-1,1,2-Trimethyl-1,1a,5,5a-tetrahydro-3-thia-cyclopropa[a]pentalene-4-carboxylic acid 4-((R/S)-2-hydroxy-propoxy)-3-chloro-benzylamide (1.0 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-3-chloro-benzylamide (8.3 mg, 0.023 mmol, Example 11, step b) and (rac)-1-bromo-propan-2-ol (12.8 mg, 0.092 mmol) following the procedure given in Example 5, step c. LC-MS: $t_R$=1.02 min, [M+1]$^+$=420.22.

Example 27

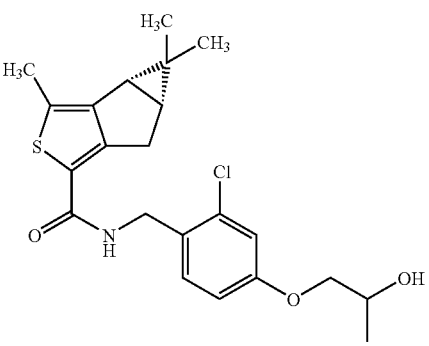

(1aS,5aR)-1,1,2-Trimethyl-1,1a,5,5a-tetrahydro-3-thia-cyclopropa[a]pentalene-4-carboxylic acid 4-((R/S)-2-hydroxy-propoxy)-2-chloro-benzylamide (1.1 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (8.3 mg, 0.023 mmol, Example 13, step b) and (rac)-1-bromo-propan-2-ol (12.8 mg, 0.092 mmol) following the procedure given in Example 5, step c. LC-MS: $t_R$=1.03 min, [M+1]$^+$=420.13.

Example 28

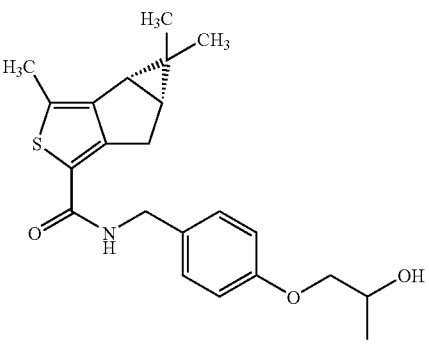

(1aS,5aR)-1,1,2-Trimethyl-1,1a,5,5a-tetrahydro-3-thia-cyclopropa[a]pentalene-4-carboxylic acid 4-((R/S)-2-hydroxy-propoxy)-benzylamide (1.86 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-benzylamide (7.5 mg, 0.023 mmol, Example 15, step b) and (rac)-1-bromo-propan-2-ol (12.8 mg, 0.092 mmol) following the procedure given in Example 5, step c. LC-MS: $t_R$=0.99 min, [M+1]$^+$=386.25.

Example 29

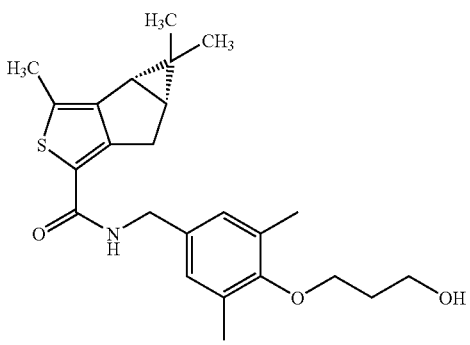

(1aS,5aR)-1,1,2-Trimethyl-1,1a,5,5a-tetrahydro-3-thia-cyclopropa[a]pentalene-4-carboxylic acid 4-(3-hydroxy-propoxy)-3,5-dimethyl-benzylamide (5.0 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (8.9 mg, 0.025 mmol, Example 5, step b) and 3-bromo-propanol (13.9 mg, 0.1 mmol) following the procedure given in Example 5, step c. LC-MS: $t_R$=1.02 min, $[M+1]^+$=414.23.

Example 30

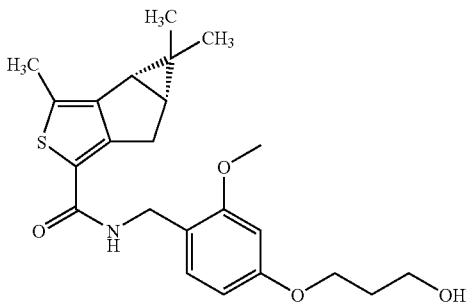

a) 3-(4-Aminomethyl-3-methoxy-phenoxy)-propan-1-ol is prepared starting from 4-aminomethyl-3-methoxy-phenol and 1-bromo-propanol in analogy to the procedures given in Example 18, steps a to c. LC-MS: $t_R$=0.67 min, $[M+1]^+$=212.16.

b) A solution of (1aS,5aR)-1,1,2-trimethyl-1,1a,5,5a-tetrahydro-3-thia-cyclopropa[a]pentalene-4-carboxylic acid (8.2 mg, 0.037 mmol), TBTU (11.9 mg, 0.037 mmol) and ethyl-diisopropylamine (19 µL, 0.111 mmol) in DMF (1 mL) is allowed to stand at rt for 30 min. The solution is added to 1-(4-aminomethyl-3-methoxy-phenoxy)-propanol (7.8 mg, 0.037 mmol) and the mixture is allowed to stand at rt for 1 h. The mixture is separated by prep. HPLC to afford (1aS,5aR)-1,1,2-trimethyl-1,1a,5,5a-tetrahydro-3-thia-cyclopropa[a]pentalene-4-carboxylic acid 4-(3-hydroxy-propoxy)-2-methoxy-benzylamide (6.5 mg) as a colourless lyophilisate. LC-MS: $t_R$=1.01 min, $[M+1]^+$=416.12.

Example 31

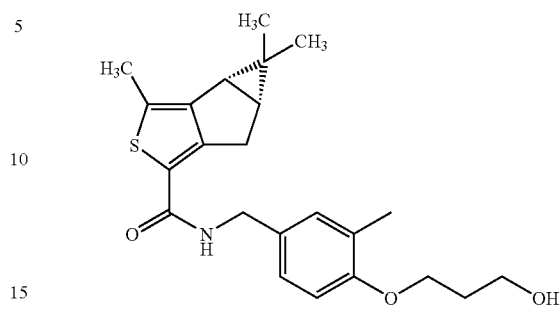

(1aS,5aR)-1,1,2-Trimethyl-1,1a,5,5a-tetrahydro-3-thia-cyclopropa[a]pentalene-4-carboxylic acid 4-(3-hydroxy-propoxy)-3-methyl-benzylamide (1.2 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-3-methyl-benzylamide (7.9 mg, 0.023 mmol, Example 9, step b) and 3-bromo-propanol (12.8 mg, 0.092 mmol) following the procedure given in Example 5, step c. LC-MS: $t_R$=1.02 min, $[M+1]^+$=400.25.

Example 32

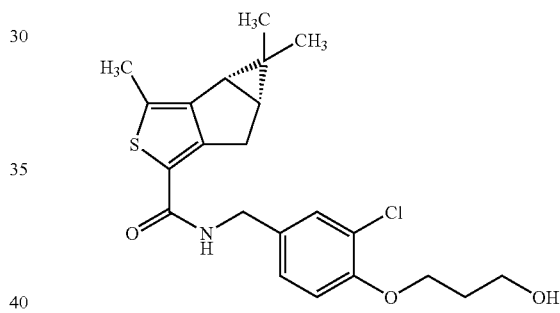

(1aS,5aR)-1,1,2-Trimethyl-1,1a,5,5a-tetrahydro-3-thia-cyclopropa[a]pentalene-4-carboxylic acid 4-(3-hydroxy-propoxy)-3-chloro-benzylamide (0.7 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-3-chloro-benzylamide (8.3 mg, 0.023 mmol, Example 11, step b) and 1-bromo-propanol (12.8 mg, 0.092 mmol) following the procedure given in Example 5, step c. LC-MS: $t_R$=1.02 min, $[M+1]^+$=420.22.

Example 33

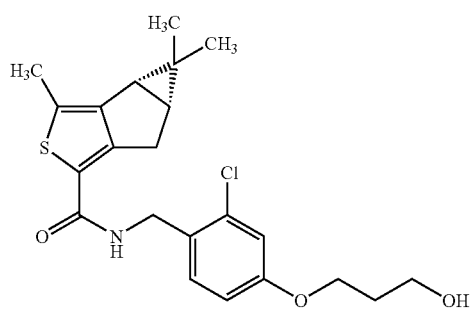

(1aS,5aR)-1,1,2-Trimethyl-1,1a,5,5a-tetrahydro-3-thia-cyclopropa[a]pentalene-4-carboxylic acid 4-(3-hydroxy-propoxy)-2-chloro-benzylamide (0.4 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (8.3 mg, 0.023 mmol, Example 13, step b) and 1-bromo-propanol (12.8 mg, 0.092 mmol) following the procedure given in Example 5, step c. LC-MS: $t_R$=1.03 min, [M+1]$^+$=420.20.

Example 34

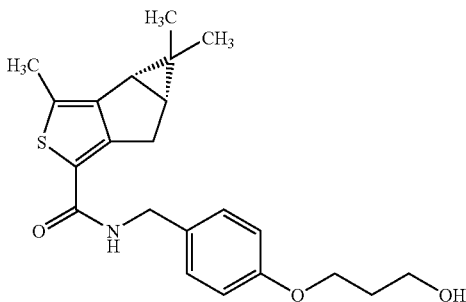

(1aS,5aR)-1,1,2-Trimethyl-1,1a,5,5a-tetrahydro-3-thia-cyclopropa[a]pentalene-4-carboxylic acid 4-(3-hydroxy-propoxy)-benzylamide (0.9 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-benzylamide (7.5 mg, 0.023 mmol, Example 15, step b) and 1-bromo-propanol (12.8 mg, 0.092 mmol) following the procedure given in Example 5, step c. LC-MS: $t_R$=0.99 min, [M+1]$^+$=386.30.

Example 35

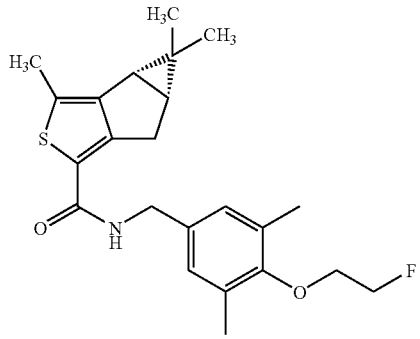

(1aS,5aR)-1,1,2-Trimethyl-1,1a,5,5a-tetrahydro-3-thia-cyclopropa[a]pentalene-4-carboxylic acid 4-(2-fluoro-ethoxy)-3,5-dimethyl-benzylamide (4.6 mg) is obtained as a colourless lyophilisate starting from (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (8.9 mg, 0.025 mmol, Example 5, step b) and 1-bromo-2-fluoro-ethane (12.7 mg, 0.1 mmol) following the procedure given in Example 5, step c. LC-MS: $t_R$=1.10 min, [M+1]$^+$=402.24.

Example 36

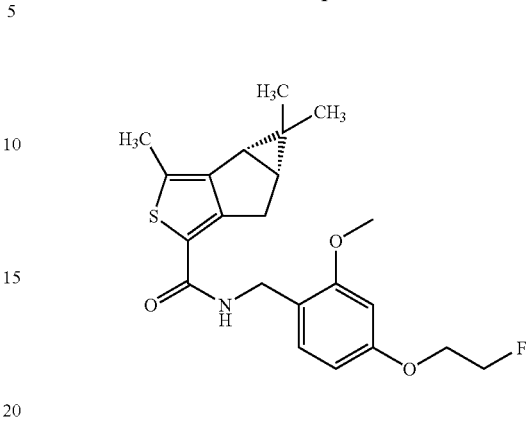

a) [4-(2-Fluoro-ethoxy)-2-methoxy-benzyl]-carbamic acid tert-butyl ester is prepared starting from 4-aminomethyl-3-methoxy-phenol and 1-bromo-2-fluoro-ethane in analogy to the procedure given in Example 18 step a and b. LC-MS: $t_R$=0.97 min, [M+1]$^+$=300.12.

b) The above [4-(2-fluoro-ethoxy)-2-methoxy-benzyl]-carbamic acid tert-butyl ester (9.9 mg, 0.33 mmol) is treated with 37% aq. HCl (0.1 mL) and acetic acid (1 mL) for 1.5 h at rt. The solvents are removed by lyophilisation to give 4-(2-fluoro-ethoxy)-2-methoxy-benzylamine hydrochloride (7.8 mg) as a beige resin. LC-MS: $t_R$=0.73 min, [M+1]$^+$=200.04.

c) (1aS,5aR)-1,1,2-Trimethyl-1,1a,5,5a-tetrahydro-3-thia-cyclopropa[a]pentalene-4-carboxylic acid 4-(2-fluoro-ethoxy)-2-methoxy-benzylamide (7.3 mg) is obtained as a colourless lyophilisate starting from (1aS,5aR)-1,1,2-trimethyl-1,1a,5,5a-tetrahydro-3-thia-cyclopropa[a]pentalene-4-carboxylic acid (7.3 mg, 0.033 mmol) and 4-(2-fluoro-ethoxy)-2-methoxy-benzylamine hydrochloride (7.8 mg, 0.033 mmol) following the procedure given in Example 18 step d. LC-MS: $t_R$=1.08 min, [M+1]$^+$=404.18.

Example 37

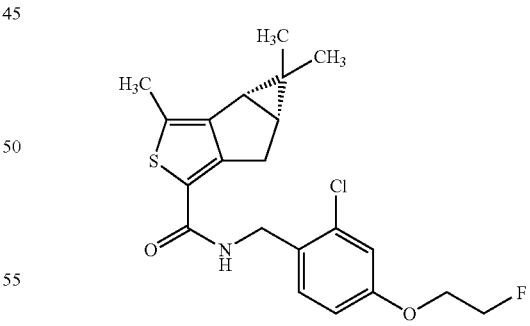

(1aS,5aR)-1,1,2-Trimethyl-1,1a,5,5a-tetrahydro-3-thia-cyclopropa[a]pentalene-4-carboxylic acid 2-chloro-4-(2-fluoro-ethoxy)-benzylamide (0.3 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-2-chloro-benzylamide (8.3 mg, 0.023 mmol, Example 13, step b) and 1-bromo-2-fluoro-ethane (11.7 mg, 0.92 mmol) following the procedure given in Example 5, step c. LC-MS: $t_R$=1.09 min, [M+1]$^+$=408.17.

Example 38

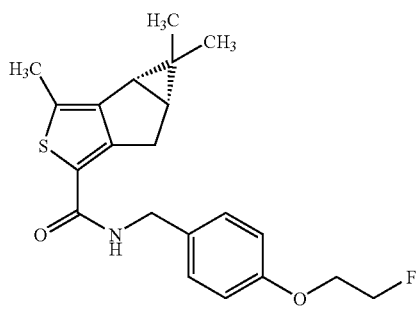

(1aS,5aR)-1,1,2-Trimethyl-1,1a,5,5a-tetrahydro-3-thia-cyclopropa[a]pentalene-4-carboxylic acid 4-(2-fluoro-ethoxy)-benzylamide (1.3 mg) is obtained as a colourless resin starting from (1aS,5aR)-1,1,2-trimethyl-1,1a,5,5a-tetrahydro-3-thia-cyclopropa[a]pentalene-4-carboxylic acid 4-hydroxy-benzylamide (7.5 mg, 0.023 mmol, Example 15, step b) and 1-bromo-2-fluoro-ethane (11.7 mg, 0.92 mmol) following the procedure given in Example 5, step c. LC-MS: $t_R$=1.05 min, $[M+1]^+$=374.10.

Example 39

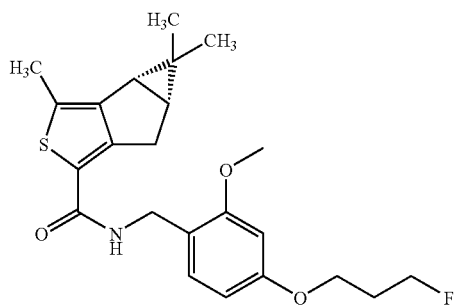

(1aS,5aR)-1,1,2-Trimethyl-1,1a,5,5a-tetrahydro-3-thia-cyclopropa[a]pentalene-4-carboxylic acid 4-(3-fluoro-propoxy)-2-methoxy-benzylamide is prepared starting from 4-aminomethyl-3-methoxy-phenol, 1-bromo-3-fluoro-propane and (1aS,5aR)-1,1,2-trimethyl-1,1a,5,5a-tetrahydro-3-thia-cyclopropa[a]pentalene-4-carboxylic acid in analogy to the procedures given in Example 36. LC-MS: $t_R$=1.10 min, $[M+1]^+$=418.14.

Example 40

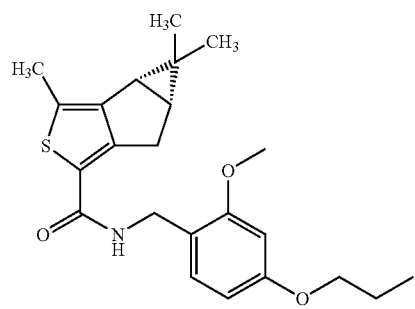

(1aS,5aR)-1,1,2-Trimethyl-1,1a,5,5a-tetrahydro-3-thia-cyclopropa[a]pentalene-4-carboxylic acid 2-methoxy-4-propoxy-benzylamide is prepared starting from 4-aminomethyl-3-methoxy-phenol, bromopropane and (1aS,5aR)-1,1,2-trimethyl-1,1a,5,5a-tetrahydro-3-thia-cyclopropa[a]pentalene-4-carboxylic acid in analogy to the procedures given in Example 36. LC-MS: $t_R$=1.13 min, $[M+1]^+$=400.19.

Example 41

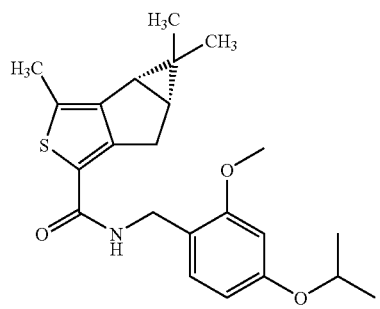

(1aS,5aR)-1,1,2-Trimethyl-1,1a,5,5a-tetrahydro-3-thia-cyclopropa[a]pentalene-4-carboxylic acid 2-methoxy-4-isopropoxy-benzylamide is prepared starting from 4-aminomethyl-3-methoxy-phenol, 2-iodopropane and (1aS,5aR)-1,1,2-trimethyl-1,1a,5,5a-tetrahydro-3-thia-cyclopropa[a]pentalene-4-carboxylic acid in analogy to the procedures given in Example 36. LC-MS: $t_R$=1.12 min, $[M+1]^+$=400.17.

Example 42

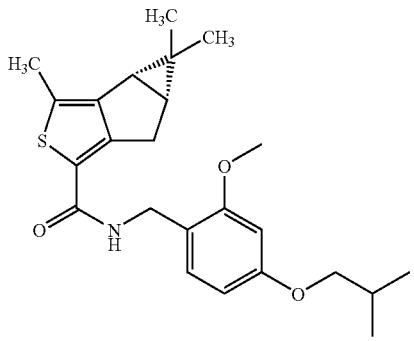

(1aS,5aR)-1,1,2-Trimethyl-1,1a,5,5a-tetrahydro-3-thia-cyclopropa[a]pentalene-4-carboxylic acid 4-isobutoxy-2-methoxy-benzylamide is prepared starting from 4-aminomethyl-3-methoxy-phenol, 1-bromo-2-methyl-propane and (1aS,5aR)-1,1,2-trimethyl- 1,1a,5,5a-tetrahydro-3-thia-cyclopropa[a]pentalene-4-carboxylic acid in analogy to the procedures given in Example 36. LC-MS: $t_R$=1.16 min, $[M+1]^+$=414.17.

Example 43

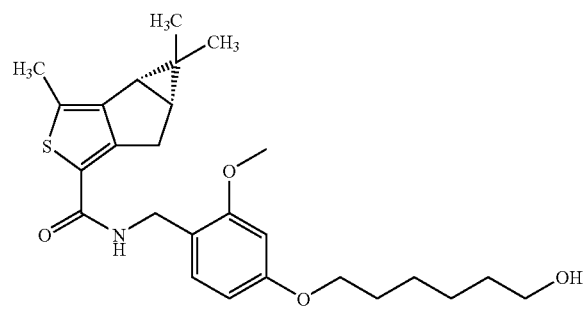

(1aS,5aR)-1,1,2-Trimethyl-1,1a,5,5a-tetrahydro-3-thia-cyclopropa[a]pentalene-4-carboxylic acid 4-(6-hydroxy-hexyloxy)-2-methoxy-benzylamide is prepared starting from 4-aminomethyl-3-methoxy-phenol, 6-bromohexanol and (1aS,5aR)-1,1,2-trimethyl-1,1a,5,5a-tetrahydro-3-thia-cyclopropa[a]pentalene-4-carboxylic acid in analogy to the procedures given in Example 18. LC-MS: $t_R$=1.08 min, $[M+1]^+$=458.25.

Example 44

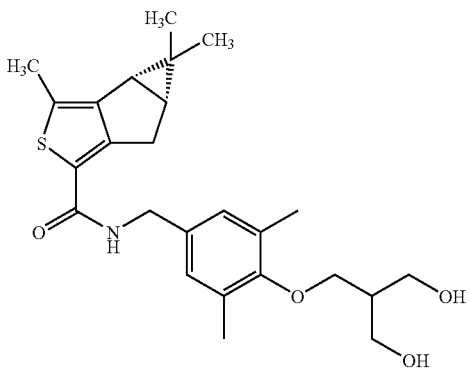

a) To a solution of (1aS,5aR)-1,1,2-trimethyl-1,1a,5,5a-tetrahydro-3-thia-cyclopropa[a]pentalene-4-carboxylic acid 4-hydroxy-3,5-dimethyl-benzylamide (28.8 mg, 0.08 mmol, Example 5 step b) in isopropanol (3.5 mL) and 2 N aq. NaOH (0.6 mL) is added a catalytic amount of NaI followed by methanesulfonic acid 2,2-dimethyl-[1,3]dioxan-5-ylmethyl ester (90 mg, 0.40 mmol, B. Xu, G. Kirschenheuter, A. F. Greslin, X. Cheng, J. Sennelo, M. Cattaneo, M. L. Zighetti, A. Chen, S.-A, Kim, H. S. Kim, N. Bischofberger, G. Cook, K. A. Jacobson, *J. Med. Chem.* 45 (2002) 5694-5709). The reaction mixture is shaken at rt for 8 h, diluted with 1 N aq. NaOH, and extracted twice with DCM. The organic extracts are dried over MgSO$_4$, filtered and evaporated. The residue is purified by prep. HPLC to give (1aS,5aR)-1,1,2-trimethyl-1,1a,5,5a-tetrahydro-3-thia-cyclopropa[a]pentalene-4-carboxylic acid 4-(2,2-dimethyl-[1,3]dioxan-5-ylmethoxy)-3,5-dimethyl-benzylamide (28 mg) as a colourless solid. LC-MS: $t_R$=1.13 min, $[M+1]^+$=484.34.

b) A solution of (1aS,5aR)-1,1,2-trimethyl-1,1a,5,5a-tetrahydro-3-thia-cyclopropa[a]pentalene-4-carboxylic acid 4-(2,2-dimethyl-[1,3]dioxan-5-ylmethoxy)-3,5-dimethyl-benzylamide (28 mg, 0.058 mmol) in acetic acid (1.6 mL) and water (0.4 mL) is stirred at rt for 1 h before it is separated by prep. HPLC to give (1aS,5aR)-1,1,2-trimethyl-1,1a,5,5a-tetrahydro-3-thia-cyclopropa[a]pentalene-4-carboxylic acid 4-(3-hydroxy-2-hydroxymethyl-propoxy)-3,5-dimethyl-benzylamide (22 mg) as a colourless solid. LC-MS: $t_R$=0.96 min, $[M+1]^+$=444.30; $^1$H NMR (CDCl$_3$): δ 6.95 (s, 2H), 5.77 (t br, J=5.8 Hz, 1H), 4.51-4.37 (m, 2H), 4.00 (d, J=5.3 Hz, 4H), 3.90 (d, J=5.3 Hz, 2H), 2.93 (dd, J=5.9, 17.6 Hz, 1H) 2.73 (d, J=17.6 Hz, 1H), 2.36 (s, 3H), 2.33-2.20 (m, 9H), 1.93-1.86 (m, 2H), 1.12 (s, 3H), 0.74 (s, 3H).

Example 45

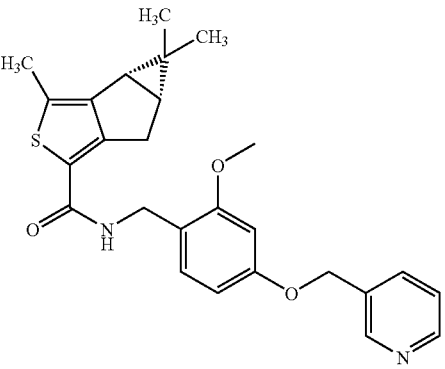

(1aS,5aR)-1,1,2-Trimethyl-1,1a,5,5a-tetrahydro-3-thia-cyclopropa[a]pentalene-4-carboxylic acid 2-methoxy-4-(pyridin-3-ylmethoxy)-benzylamide is prepared starting from 4-aminomethyl-3-methoxy-phenol, 3-bromomethyl-pyridinel hydrobromide and (1aS,5aR)-1,1,2-trimethyl-1,1a,5,5a-tetrahydro-3-thia-cyclopropa[a]pentalene-4-carboxylic acid in analogy to the procedures given in Example 36. LC-MS: $t_R$=0.90 min, $[M+1]^+$=449.20.

Example 46

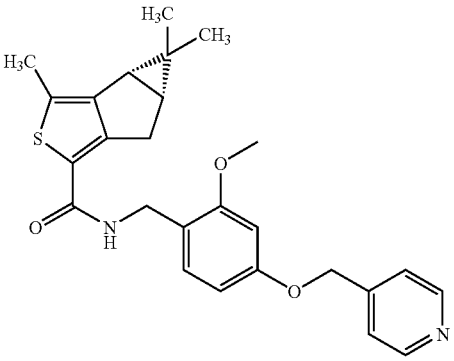

(1aS,5aR)-1,1,2-Trimethyl-1,1a,5,5a-tetrahydro-3-thia-cyclopropa[a]pentalene-4-carboxylic acid 2-methoxy-4-(pyridin-4-ylmethoxy)-benzylamide is prepared starting from 4-aminomethyl-3-methoxy-phenol, 4-bromomethyl-pyridinel hydrobromide and (1aS,5aR)-1,1,2-trimethyl-1,1a,5, 5a-tetrahydro-3-thia-cyclopropa[a]pentalene-4-carboxylic acid in analogy to the procedures given in Example 36. LC-MS: $t_R$=0.88 min, [M+1]$^+$=449.21.

Example 47

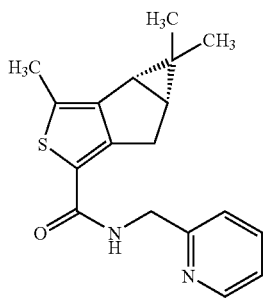

(1aS,5aR)-1,1,2-Trimethyl-1,1a,5,5a-tetrahydro-3-thia-cyclopropa[a]pentalene-4-carboxylic acid (pyridin-2-ylmethyl)-amide (4.2 mg) is obtained as a colourless lyophilisate starting from (1aS,5aR)-1,1,2-trimethyl-1,1a,5,5a-tetrahydro-3-thia-cyclopropa[a]pentalene-4-carboxylic acid (Compound of Structure 1) (4.0 mg, 0.018 mmol) and C-pyridin-2-yl-methylamine (2.4 mg, 0.022 mmol) following the procedure given in Example 1. LC-MS: $t_R$=0.79 min, [M+1]$^+$=313.03.

Example 48

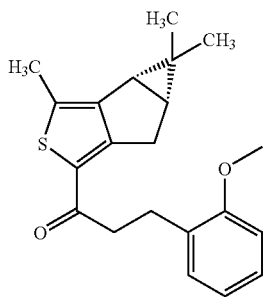

a) A mixture of triethylsilane (34.9 g, 0.3 mol), TFA (96 mL) and 2-bromo-1-(2-methoxy-phenyl)-ethanone (6.9 g, 30 mmol) is stirred at rt for 30 min before it is poured onto an ice/water mixture (600 mL). The mixture is neutralised by adding 2 N aq. NaOH and sat. aq. NaHCO$_3$ (200 mL), and is extracted with DCM (2×200 mL). The combined organic extracts are dried over Na$_2$SO$_4$, filtered and evaporated. The obtained residue is purified by chromatography on silica gel (TBME:EA 40:1) to give 1-(2-bromo-ethyl)-2-methoxy-benzene (4.50 g) as a colourless liquid. LC: $t_R$=1.00 min.

b) At rt, a solution of 1-(2-bromo-ethyl)-2-methoxy-benzene (1.0 g, 4.15 mmol) in abs. THF (5 mL) is added to Mg turnings (0.13 g, 5.35 mmol) suspended in abs. THF (5 mL) over a period of 20 min. The thus obtained Grignard reagent is then added at to an ice-cold solution of (1aS,5aR)-1,1,2-trimethyl-1,1a,5,5a-tetrahydro-3-thia-cyclopropa[a]pentalene-4-carboxylic acid methoxy-methyl-amide (400 mg, 1.5 mmol) in THF (5 mL). The reaction mixture is stirred at rt for 1 h, quenched by adding sat. aq. NH$_4$Cl (10 mL), diluted with water (100 mL) and extracted twice with DCM (100 mL). The combined organic extracts are dried over Na$_2$SO$_4$, filtered and evaporated. The resulting residue is purified by prep. HPLC to afford 3-(2-methoxy-phenyl)-1-((1aS,5aR)-1,1,2-trimethyl-1,1a,5,5a-tetrahydro-3-thia-cyclopropa[a]penta-len-4-yl)-propan-1-one (390 mg) as a colourless oil. LC-MS: $t_R$=1.15 min, [M+1]$^+$=341.21; $^1$H NMR (CDCl$_3$): δ 7.22-7.14 (m, 2H), 6.90-6.81 (m, 2H), 3.82 (s, 3H), 3.20-2.90 (m, 5H), 2.79 (d, J=18.8 Hz, 1H), 2.38 (s, 3H), 1.88 (d, J=2.9 Hz, 2H), 1.12 (s, 3H), 0.72 (s, 3H).

Example 49

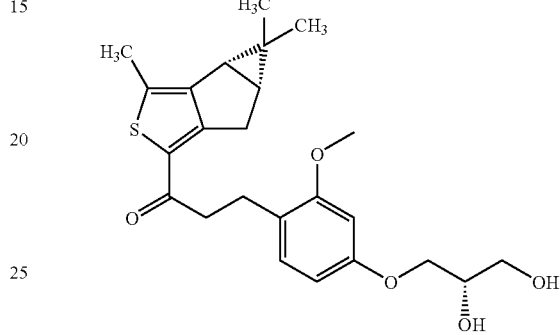

a) A stirred solution of (1aS,5aR)-1-(1,1,2-trimethyl-1,1a,5,5a-tetrahydro-3-thia-cyclopropa[a]pen-talen-4-yl)-ethanone (110 mg, 0.5 mmol), 4-hydroxy-2-methoxybenzaldehyde (150 mg, 0.99 mmol) and KOH (0.5 g, 8.9 mmol) in ethanol (5 mL) is heated to 60° C. for 6 h followed by 80° C. for 2 h. Formic acid (1 mL) is added and the mixture is separated by prep. HPLC to afford 3-(4-hydroxy-2-methoxy-phenyl)-1-((1aS,5aR)-1,1,2-trimethyl-1,1a,5,5a-tetrahydro-3-thia-cyclopropa[a]pentalen-4-yl)-propenone (75 mg) as a yellow solid. LC-MS: $t_R$=1.08 min, [M+1]$^+$=355.15; $^1$H NMR (D$_6$-DMSO): δ 10.15 (s, 1H), 7.73 (d, J=15.2 Hz, 1H), 7.55 (d, J=8.8 Hz, 1H), 7.23 (d, J=15.8 Hz, 1H), 6.47-6.40 (m, 2H), 3.84 (s, 3H), 3.12 (dd, J=6.4, 18.8 Hz, 1H), 2.88 (d, J=18.8 Hz, 1H), 2.07 (s, 3H), 2.02-1.93 (m, 2H), 1.11 (s, 3H), 0.70 (s, 3H).

b) To a solution of 3-(4-hydroxy-2-methoxy-phenyl)-1-((1aS,5aR)-1,1,2-trimethyl-1,1a,5,5a-tetrahydro-3-thia-cyclo-propa[a]pentalen-4-yl)-propenone (71 mg, 0.2 mmol) in ethanol (3.5 mL) is added Pd/C (30 mg, 10% Pd). The resulting suspension is stirred at rt for 30 min under 1 atm H$_2$. The mixture is filtered over celite and the filtrate is evaporated. The residue is purified by prep. HPLC to give 3-(4-hydroxy-2-methoxy-phenyl)-1-((1aS,5aR)-1,1,2-trimethyl-1,1a,5,5a-tetrahydro-3-thia-cyclopropa[a]pentalen-4-yl)-propan-1-one (22 mg) as a slightly yellow resin. LC-MS: $t_R$=1.06 min, [M+1]$^+$=357.22; $^1$H NMR (CD$_3$OD): δ 6.88 (d, J=8.2 Hz, 1H), 6.37 (d, J=2.3 Hz, 1H), 6.26 (dd, J=2.3, 8.2 Hz, 1H), 3.76 (s, 3H), 3.00-2.74 (m, 6H), 2.04 (s, 3H), 1.98-1.89 (m, 2H), 1.12 (s, 3H), 0.70 (s, 3H).

c) 3-[4-((S)-2,3-Dihydroxy-propoxy)-2-methoxy-phenyl]-1-((1aS,5aR)-1,1,2-trimethyl-1,1a,5,5a-tetrahydro-3-thia-cyclopropa[a]pentalen-4-yl)-propan-1-one (3.3 mg) is obtained as a colourless resin starting from the above 3-(4-hydroxy-2-methoxy-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and (S)-3-chloro-propane-1,2-diol (11.1 mg, 0.1 mmol) following the procedure given in Example 5, step c. LC-MS: $t_R$=1.00 min,

[M+1]$^+$=431.26; $^1$H NMR (CDCl$_3$): δ 7.06 (d, J=8.02 Hz, 1H), 6.45 (d, J=2.3 Hz, 1H), 6.40 (dd, J=2.3, 8.2 Hz, 1H), 4.14-4.06 (m, 1H), 4.05-4.01 (m, 2H), 3.85 (dd, J=4.1, 11.1 Hz, 1H), 3.80 (s, 3H), 3.75 (dd, J=5.3, 11.1 Hz, 1H), 3.02-2.90 (m, 5H), 2.79 (d, J=18.8 Hz, 1H), 2.38 (s, 3H), 1.97 (s br, 2H), 1.91-1.85 (m, 2H), 1.12 (s, 3H), 0.71 (s, 3H).

Example 50

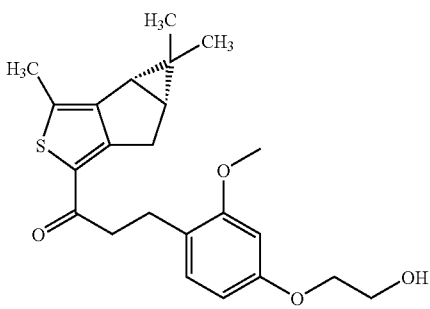

3-[4-(2-Hydroxy-ethoxy)-2-methoxy-phenyl]-1-((1aS, 5aR)-1,1,2-trimethyl-1,1a,5,5a-tetrahydro-3-thia-cyclopropa[a]pentalen-4-yl)-propan-1-one (1.9 mg) is obtained as a colourless resin starting from 3-(4-hydroxy-2-methoxy-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol, Example 49, step b and 2-bromoethanol (12.5 mg, 0.1 mmol) following the procedure given in Example 5, step c. LC-MS: t$_R$=1.06 min, [M+1]$^+$=400.72; $^1$H NMR (CDCl$_3$): δ 7.06 (d, J=8.2 Hz, 1H), 6.47 (d, J=2.3 Hz, 1H), 6.41 (dd, J=2.3, 8.2 Hz, 1H), 4.09-4.05 (m, 2H), 3.98-3.92 (m, 2H), 3.81 (s, 3H), 3.01-2.90 (m, 5H), 2.79 (d, J=18.8 Hz, 1H), 2.38 (s, 3H), 1.90-1.86 (m, 2H), 1.12 (s, 3H), 0.72 (s, 3H).

Example 51

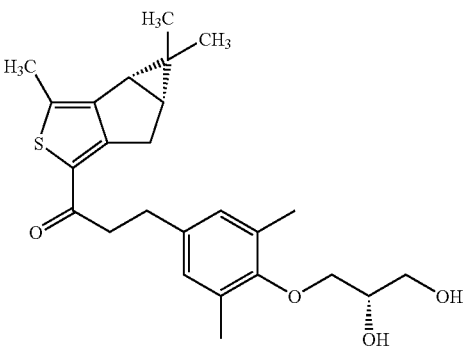

a) A stirred solution of (1aS,5aR)-1-(1,1,2-trimethyl-1,1a,5,5a-tetrahydro-3-thia-cyclopropa[a]pen-talen-4-yl)-ethanone (441 mg, 1.8 mmol), 4-hydroxy-3,5-dimethylbenzaldehyde (751 mg, 0.99 mmol) in ethanol (10 mL) and HCl (5 mL, 1 N in isopropanol) is stirred at rt for 80 min. The blue reaction mixture is separated by prep. HPLC to afford 3-(4-hydroxy-3,5-dimethyl-phenyl)-1-((1aS,5aR)-1,1,2-trimethyl-1,1a,5,5a-tetrahydro-3-thia-cyclo-propa[a]pentalen-4-yl)-propenone (360 mg) as a yellow solid. LC-MS: t$_R$=1.13 min, [M+1]$^+$=353.17; $^1$H NMR (CDCl$_3$): δ 7.62 (d, J=15.2 Hz, 1H), 7.24 (s, 2H), 7.06 (d, J=15.2 Hz, 1H), 4.93 (s br, 1H), 3.13 (dd, J=6.4, 18.8 Hz, 1H), 2.96 (d, J=18.8 Hz, 1H), 2.43 (s, 3H), 2.29 (s, 6H), 1.99-1.90 (m, 2H), 1.15 (s, 3H), 0.76 (s, 3H).

b) To a solution of 3-(4-hydroxy-3,5-dimethyl-phenyl)-1-((1aS,5aR)-1,1,2-trimethyl-1,1a,5,5a-tetrahydro-3-thia-cyclo-propa[a]pentalen-4-yl)-propenone (360 mg, 1.03 mmol) in ethanol (20 mL) is added Pd/C (450 mg, 10% Pd). The resulting suspension is stirred at rt for 4.5 h under 1 atm H$_2$. The mixture is filtered over celite and the filtrate is evaporated. The residue is purified by prep. HPLC to give 3-(4-hydroxy-3,5-dimethyl-phenyl)-1-((1aS,5aR)-1,1,2-trimethyl-1,1a,5,5a-tetrahydro-3-thia-cyclopropa[a]pentalen-4-yl)-propan-1-one (280 mg) as a slightly yellow resin. LC-MS: t$_R$=1.11 min, [M+1]$^+$=355.20.

c) 3-[4-((S)-2,3-Dihydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (4.4 mg) is obtained as a colourless resin starting from the above 3-(4-hydroxy-3,5-dimethyl-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and (S)-3-bromo-propane-1,2-diol (15.5 mg, 0.1 mmol) following the procedure given in Example 5, step c. LC-MS: t$_R$=1.02 min, [M+1]$^+$=429.25.

Example 52

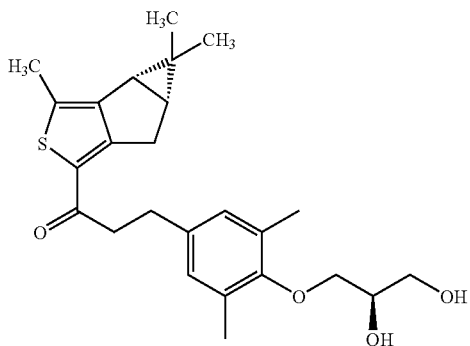

3-[4-((R)-2,3-Dihydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (5.4 mg) is obtained as a colourless lyophilisate starting from 3-(4-hydroxy-3,5-dimethyl-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and (R)-3-bromo-propane-1,2-diol (15.5 mg, 0.1 mmol) in analogy to the procedures given in Example 51. LC-MS: t$_R$=1.02 min, [M+1]$^+$=429.29.

Example 53

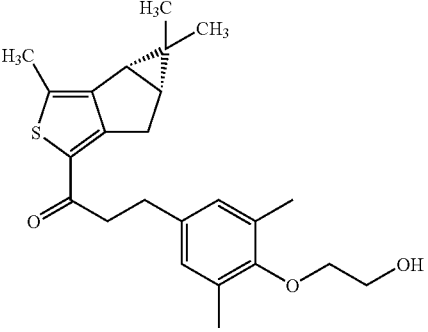

3-[4-(2-Hydroxy-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (3.1 mg) is obtained as a colourless resin starting from 3-(4-hydroxy-3,5-dimethyl-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and 2-bromoethanol (12.5 mg, 0.1 mmol) in analogy to the procedures given in Example 51. LC-MS: $t_R$=1.09 min, $[M+1]^+$=499.2.

Example 54

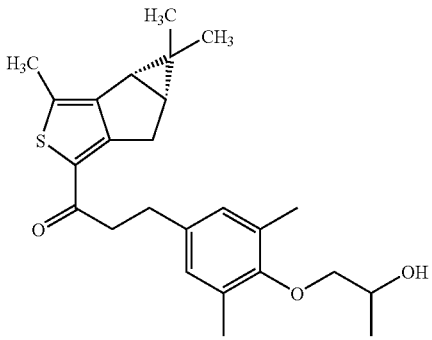

3-[4-(2-(R/S)-Hydroxy-propoxy)-3,5-dimethyl-phenyl]-1-(1,1,2-trimethyl-1,1a,5,5a-tetrahydro-3-thia-cyclopropa[a]pentalen-4-yl)-propan-1-one (1.2 mg) is obtained as a colourless resin starting from 3-(4-hydroxy-3,5-dimethyl-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and rac-1-bromo-propan-2-ol (13.9 mg, 0.1 mmol) in analogy to the procedures given in Example 51. LC-MS: $t_R$=1.12 min, $[M+1]^+$=413.24.

Example 55

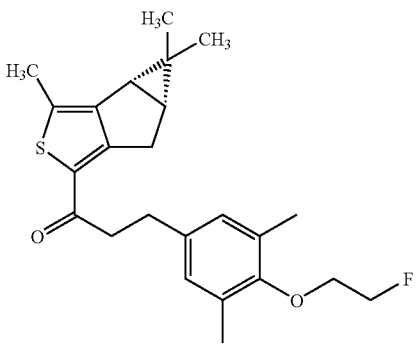

3-[4-(2-(2-Fluoroethoxy)-3,5-dimethyl-phenyl]-1-(1,1,2-trimethyl-1,1a,5,5a-tetrahydro-3-thia-cyclopropa[a]pentalen-4-yl)-propan-1-one (3.1 mg) is obtained as a colourless resin starting from 3-(4-hydroxy-3,5-dimethyl-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and 1-bromo-2-fluoroethane (12.7 mg, 0.1 mmol) in analogy to the procedures given in Example 51. LC-MS: $t_R$=1.18 min, $[M+1]^+$=401.25.

Example 56

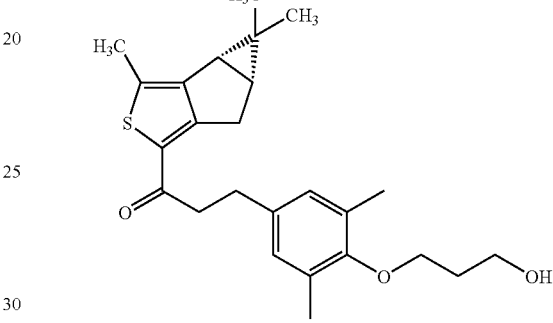

3-[4-(3-Hydroxy-propoxy)-3,5-dimethyl-phenyl]-1-(1,1,2-trimethyl-1,1a,5,5a-tetrahydro-3-thia-cyclopropa[a]pentalen-4-yl)-propan-1-one (3.4 mg) is obtained as a colourless resin starting from 3-(4-hydroxy-3,5-dimethyl-phenyl)-1-((1aS,5aR)-1,1,2-trimethyl-1,1a,5,5a-tetrahydro-3-thia-cyclopropa[a]-pentalen-4-yl)-propan-1-one (8.9 mg, 0.025 mmol) and 3-bromopropanol (13.9 mg, 0.1 mmol) in analogy to the procedures given in Example 51. LC-MS: $t_R$=1.11 min, $[M+1]^+$=413.23.

Examples 57 to 63

The following examples are prepared starting from 3-(4-hydroxy-3,5-dimethyl-phenyl)-1-((1aS,5aR)-1,1,2-trimethyl-1,1a,5,5a-tetrahydro-3-thia-cyclo-propa[a]-pentalen-4-yl)-propenone in analogy to the procedure given in Example 5c.

| | | LC-MS | |
|---|---|---|---|
| Example | Name | $t_R$ [min] | $[M + 1]^+$ |
| 57 | 3-(4-Methoxy-3,5-dimethyl-phenyl)-1-((1aS,5aR)-1,1,2-trimethyl-1,1a,5,5a-tetrahydro-3-thia-cyclopropa[a]pentalen-4-yl)-propan-1-one | 1.18 | 369.23 |
| 58 | 3-(4-Ethoxy-3,5-dimethyl-phenyl)-1-((1aS,5aR)-1,1,2-trimethyl-1,1a,5,5a-tetrahydro-3-thia-cyclopropa[a]pentalen-4-yl)-propan-1-one | 1.20 | 383.24 |

| Example | Name | LC-MS t$_R$ [min] | [M + 1]$^+$ |
|---|---|---|---|
| 59 | 3-(3,5-Dimethyl-4-propoxy-phenyl)-1-((1aS,5aR)-1,1,2-trimethyl-1,1a,5,5a-tetrahydro-3-thia-cyclopropa[a]pentalen-4-yl)-propan-1-one | 1.23 | 397.24 |
| 60 | 3-(4-Butoxy-3,5-dimethyl-phenyl)-1-((1aS,5aR)-1,1,2-trimethyl-1,1a,5,5a-tetrahydro-3-thia-cyclopropa[a]pentalen-4-yl)-propan-1-one | 1.25 | 411.26 |
| 61 | 3-(4-sec-Butoxy-3,5-dimethyl-phenyl)-1-((1aS,5aR)-1,1,2-trimethyl-1,1a,5,5a-tetrahydro-3-thia-cyclopropa[a]pentalen-4-yl)-propan-1-one | 1.25 | 411.26 |
| 62 | 3-[4-(6-Hydroxy-hexyloxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one | 1.18 | 455.31 |
| 63 | 3-[4-(3-Hydroxy-2-hydroxymethyl-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one | 1.04 | 443.28 |

Example 63

$^1$H NMR (CDCl$_3$): δ 6.85 (s, 2H), 4.03-3.96 (m, 4H), 3.90 (d, J=5.3 Hz, 2H), 3.02-2.85H), 2.78 (d, J=18.8 Hz, 1H), 2.37 (s, 3H), 2.25 (s, 6H), 2.25-2.15 (m, 1H), 1.92-1.86 (m, 2H), 1.11 (s, 3H), 0.70 (s, 3H).

Examples 64 to 68

The following examples are prepared in analogy to Example 51.

| Example | Name | LC-MS t$_R$ [min] | [M + 1]$^+$ |
|---|---|---|---|
| 64 | 3-[4-((S)-2,3-Dihydroxy-propoxy)-3-ethyl-5-methyl-phenyl]-1-((1aS,5aR)-1,1,2-trimethyl-1,1a,5,5a-tetrahydro-3-thia-cyclopropa[a]pentalen-4-yl)-propan-1-one | 1.05 | 443.28 |
| 65 | 3-[4-((R)-2,3-Dihydroxy-propoxy)-3-ethyl-5-methyl-phenyl]-1-((1aS,5aR)-1,1,2-trimethyl-1,1a,5,5a-tetrahydro-3-thia-cyclopropa[a]pentalen-4-yl)-propan-1-one | 1.05 | 443.29 |
| 66 | 3-[3-Ethyl-4-(2-hydroxy-ethoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.11 | 413.37 |
| 67 | 3-[3-Ethyl-4-(2-hydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.14 | 427.32 |
| 68 | 3-[3-Ethyl-4-(3-hydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.13 | 427.33 |

Example 69 a) To a solution of 2,6-diethylphenol (3.80 g, 25.3 mmol) in acetic acid (30 mL) hexamethylenetetraamine (5.3 g, 37.9 mmol) is added and the mixture is heated to 120° C. A first fraction of the solvent is distilled off (Dean-Stark), then the mixture is refluxed for 3 h. The mixture is cooled to rt, diluted with water (100 mL) and extracted twice with EA (2×200 mL). The organic extracts are washed with sat. aq. NaHCO$_3$, dried and the solvent is removed in vacuo. The crude product is purified by column chromatography eluting with DCM containing 2% of methanol to give 3,5-diethyl-4-hydroxy-benzaldehyde (1.8 g) as colourless solid; $^1$H NMR (CDCl$_3$): δ 9.85 (s, 1H), 7.57 (s, 2H), 5.32 (s, 1H), 2.69 (q, J=7.6 Hz, 2H), 1.30 (t, J=7.6 Hz, 3H).

b) The following example is prepared using the above 3,5-diethyl-4-hydroxybenzaldehyde in analogy to the procedures given in Example 51.

|  |  | LC-MS | |
|---|---|---|---|
| Example | Name | $t_R$ [min] | $[M + 1]^+$ |
| 69 | 3-[4-((S)-2,3-Dihydroxy-propoxy)-3,5-diethyl-phenyl]-1-((1aS,5aR)-1,1,2-trimethyl-1,1a,5,5a-tetrahydro-3-thia-cyclopropa[a]pentalen-4-yl)-propan-1-one | 1.07 | 457.23 |

Examples 70 to 74

The following examples are prepared in analogy to Example 51 starting from 3-chloro-4-hydroxy-5-methylbenzahldehyde.

|  |  | LC-MS | |
|---|---|---|---|
| Example | Name | $t_R$ [min] | $[M + 1]^+$ |
| 70 | 3-[3-Chloro-4-((S)-2,3-dihydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.04 | 449.28 |
| 71 | 3-[3-Chloro-4-((R)-2,3-dihydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.04 | 449.39 |
| 72 | 3-[3-Chloro-4-(2-hydroxy-ethoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.10 | 419.32 |
| 73 | 3-[3-Chloro-4-(3-hydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.12 | 433.42 |
| 74 | 3-[3-Chloro-4-(2-hydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one | 1.13 | 433.31 |

Examples 75 to 80

The following examples are prepared in analogy to Example 51 starting from 3-chloro-4-hydroxybenzahldehyde.

|  |  | LC-MS | |
|---|---|---|---|
| Example | Name | $t_R$ [min] | $[M + 1]^+$ |
| 75 | 3-[3-Chloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.03 | 435.16 |
| 76 | 3-[3-Chloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.03 | 435.09 |
| 77 | 3-[3-Chloro-4-(3-hydroxy-2-hydroxymethyl-propoxy)-phenyl]-1-((1aS,5aR)-1,1,2-trimethyl-1,1a,5,5a-tetrahydro-3-thia-cyclopropa[a]pentalen-4-yl)-propan-1-one | 1.04 | 449.20 |
| 78 | 3-[3-Chloro-4-(2-hydroxy-ethoxy)-phenyl]-1-((1aS,5aR)-1,1,2-trimethyl-1,1a,5,5a-tetrahydro-3-thia-cyclopropa[a]pentalen-4-yl)-propan-1-one | 1.09 | 405.16 |
| 79 | 3-[3-Chloro-4-(3-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.11 | 419.07 |
| 80 | 3-[3-Chloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.11 | 419.09 |

Example 75

$^1$H NMR (CDCl$_3$): δ 7.23 (d, J=2.3 Hz, 1H), 7.07 (dd, J=2.3, 8.2 Hz, 1H), 6.85 (d, J=8.2 Hz, 1H), 4.16-4.04 (m, 3H), 3.91-3.78 (m, 2H), 3.02-2.90 (m, 5H), 2.78 (d, J=18.8 Hz, 1H), 2.76 (d br, J=4 Hz, 1H), 2.39 (s, 3H), 2.15 (t br, J=6 Hz, 1H), 1.92-1.85 (m, 2H), 1.11 (s, 3H), 0.70 (s, 3H).

Examples 81 to 85

The following examples are prepared in analogy to Example 51 starting from 2-chloro-4-hydroxybenzahldehyde.

| Example | Name | LC-MS t$_R$ [min] | [M + 1]$^+$ |
|---|---|---|---|
| 81 | 3-[2-Chloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.03 | 435.31 |
| 82 | 3-[2-Chloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.03 | 435.25 |
| 83 | 3-[2-Chloro-4-(2-hydroxy-ethoxy)-phenyl]-1-((1aS,5aR)-1,1,2-trimethyl-1,1a,5,5a-tetrahydro-3-thia-cyclopropa[a]pentalen-4-yl)-propan-1-one | 1.10 | 405.21 |
| 84 | 3-[2-Chloro-4-(3-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.12 | 419.28 |
| 85 | 3-[2-Chloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.12 | 419.21 |

Examples 86 to 90

The following examples are prepared in analogy to Example 51 starting from 3-methyl-4-hydroxybenzahldehyde.

| Example | Name | LC-MS t$_R$ [min] | [M + 1]$^+$ |
|---|---|---|---|
| 86 | 3-[4-((S)-2,3-Dihydroxy-propoxy)-3-methyl-phenyl]-1-((1aS,5aR)-1,1,2-trimethyl-1,1a,5,5a-tetrahydro-3-thia-cyclopropa[a]pentalen-4-yl)-propan-1-one | 1.02 | 415.26 |
| 87 | 3-[4-(3-Hydroxy-2-hydroxymethyl-propoxy)-3-methyl-phenyl]-1-((1aS,5aR)-1,1,2-trimethyl-1,1a,5,5a-tetrahydro-3-thia-cyclopropa[a]pentalen-4-yl)-propan-1-one | 1.04 | 429.23 |
| 88 | 3-[4-(2-Hydroxy-ethoxy)-3-methyl-phenyl]-1-((1aS,5aR)-1,1,2-trimethyl-1,1a,5,5a-tetrahydro-3-thia-cyclopropa[a]pentalen-4-yl)-propan-1-one | 1.09 | 385.24 |
| 89 | 3-[4-(3-Hydroxy-propoxy)-3-methyl-phenyl]-1-((1aS,5aR)-1,1,2-trimethyl-1,1a,5,5a-tetrahydro-3-thia-cyclopropa[a]pentalen-4-yl)-propan-1-one | 1.11 | 399.30 |
| 90 | 3-[4-(2-Hydroxy-propoxy)-3-methyl-phenyl]-1-((1aS,5aR)-1,1,2-trimethyl-1,1a,5,5a-tetrahydro-3-thia-cyclopropa[a]pentalen-4-yl)-propan-1-one | 1.11 | 399.19 |

Example 86

$^1$H NMR (CDCl$_3$): δ 7.03-6.96 (m, 2H), 6.77-6.72 (m, 1H), 4.16-4.08 (m, 2H), 4.05-4.00 (m, 2H), 3.90-3.73 (m, 2H), 3.02-2.90 (m, 5H), 2.78 (d, J=18.8 Hz, 1H), 2.56 (s br, 1H), 2.37 (s, 3H), 2.20 (s, 3H), 2.02 (s br, 1H), 1.91-1.85 (m, 2H), 1.11 (s, 3H), 0.70 (s, 3H).

Examples 91 to 95

The following examples are prepared in analogy to Example 51 starting from 2,6-dimethyl-4-hydroxybenzahldehyde.

| Example | Name | LC-MS $t_R$ [min] | $[M + 1]^+$ |
|---|---|---|---|
| 91 | 3-[4-((S)-2,3-Dihydroxy-propoxy)-2,6-dimethyl-phenyl]-1-((1aS,5aR)-1,1,2-trimethyl-1,1a,5,5a-tetrahydro-3-thia-cyclopropa[a]pentalen-4-yl)-propan-1-one | 1.03 | 429.46 |
| 92 | 3-[4-((R)-2,3-Dihydroxy-propoxy)-2,6-dimethyl-phenyl]-1-((1aS,5aR)-1,1,2-trimethyl-1,1a,5,5a-tetrahydro-3-thia-cyclopropa[a]pentalen-4-yl)-propan-1-one | 1.03 | 429.40 |
| 93 | 3-[4-(2-Hydroxy-ethoxy)-2,6-dimethyl-phenyl]-1-((1aS,5aR)-1,1,2-trimethyl-1,1a,5,5a-tetrahydro-3-thia-cyclopropa[a]pentalen-4-yl)-propan-1-one | 1.09 | 399.37 |
| 94 | 3-[4-(3-Hydroxy-propoxy)-2,6-dimethyl-phenyl]-1-((1aS,5aR)-1,1,2-trimethyl-1,1a,5,5a-tetrahydro-3-thia-cyclopropa[a]pentalen-4-yl)-propan-1-one | 1.12 | 413.32 |
| 95 | 3-[4-(2-Hydroxy-propoxy)-2,6-dimethyl-phenyl]-1-((1aS,5aR)-1,1,2-trimethyl-1,1a,5,5a-tetrahydro-3-thia-cyclopropa[a]pentalen-4-yl)-propan-1-one | 1.12 | 413.33 |

Examples 96 to 100

The following examples are prepared in analogy to Example 51 starting from 2,3,5-trimethyl-4-hydroxybenzahldehyde.

| Example | Name | LC-MS $t_R$ [min] | $[M + 1]^+$ |
|---|---|---|---|
| 96 | 3-[4-((S)-2,3-Dihydroxy-propoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one | 1.04 | 443.32 |
| 97 | 3-[4-((R)-2,3-Dihydroxy-propoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one | 1.04 | 443.41 |
| 98 | 3-[4-(2-Hydroxy-ethoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one | 1.11 | 413.34 |
| 99 | 3-[4-(3-Hydroxy-propoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one | 1.13 | 427.35 |
| 100 | 3-[4-(2-Hydroxy-propoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one | 1.13 | 427.34 |

Examples 101 to 105

The following examples are prepared in analogy to Example 51 starting from 3,5-dichloro-4-hydroxybenzahldehyde.

| Example | Name | LC-MS $t_R$ [min] | $[M + 1]^+$ |
|---|---|---|---|
| 101 | 3-[3,5-Dichloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.05 | 469.28 |

|         |                                                                                                                                                                 | LC-MS    |           |
| ------- | --------------------------------------------------------------------------------------------------------------------------------------------------------------- | -------- | --------- |
| Example | Name                                                                                                                                                            | $t_R$ [min] | $[M + 1]^+$ |
| 102     | 3-[3,5-Dichloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one          | 1.05     | 469.36    |
| 103     | 3-[3,5-Dichloro-4-(2-hydroxy-ethoxy)-phenyl]-1-((1aS,5aR)-1,1,2-trimethyl-1,1a,5,5a-tetrahydro-3-thia-cyclopropa[a]pentalen-4-yl)-propan-1-one                   | 1.12     | 439.30    |
| 104     | 3-[3,5-Dichloro-4-(3-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one                  | 1.14     | 453.33    |
| 105     | 3-[3,5-Dichloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one                  | 1.15     | 453.30    |

Examples 106 to 109

The following examples are prepared in analogy to Example 51 starting from 3-chloro-4-hydroxy-5-methoxy-benzahldehyde.

|         |                                                                                                                                                                          | LC-MS    |           |
| ------- | ------------------------------------------------------------------------------------------------------------------------------------------------------------------------ | -------- | --------- |
| Example | Name                                                                                                                                                                     | $t_R$ [min] | $[M + 1]^+$ |
| 106     | 3-[3-Chloro-4-((S)-2,3-dihydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one             | 1.02     | 465.20    |
| 107     | 3-[3-Chloro-4-((R)-2,3-dihydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one             | 1.03     | 465.24    |
| 108     | 3-[3-Chloro-4-(2-hydroxy-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one                      | 1.09     | 435.15    |
| 109     | 3-[3-Chloro-4-(3-hydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one                     | 1.10     | 449.24    |

Example 106

$^1$H NMR (CDCl$_3$): δ 6.85 (d, J=1.8 Hz, 1H), 6.70 (d, J=1.8 Hz, 1H), 4.25-4.17 (m, 1H), 4.03-3.95 (m, 2H), 3.85 (s, 3H), 3.83-3.70 (m, 2H), 3.48-3.35 (m, 2H), 3.05-2.88 (m, 5H), 2.78 (d, J=18.8 Hz, 1H), 2.38 (s, 3H), 1.93-1.86 (m, 2H), 1.11 (s, 3H), 0.70 (s, 3H).

Examples 110 to 114

The following examples are prepared in analogy to Example 51 starting from 3-fluoro-4-hydroxy-5-methoxy-benzahldehyde.

|         |                                                                                                                                                                     | LC-MS    |           |
| ------- | ------------------------------------------------------------------------------------------------------------------------------------------------------------------- | -------- | --------- |
| Example | Name                                                                                                                                                                | $t_R$ [min] | $[M + 1]^+$ |
| 110     | 3-[4-((S)-2,3-Dihydroxy-propoxy)-3-fluoro-5-methoxy-phenyl]-1-((1aS,5aR)-1,1,2-trimethyl-1,1a,5,5a-tetrahydro-3-thia-cyclopropa[a]pentalen-4-yl)-propan-1-one        | 1.00     | 449.32    |

-continued

| Example | Name | LC-MS | |
|---|---|---|---|
| | | $t_R$ [min] | $[M + 1]^+$ |
| 111 | 3-[4-((R)-2,3-Dihydroxy-propoxy)-3-fluoro-5-methoxy-phenyl]-1-((1aS,5aR)-1,1,2-trimethyl-1,1a,5,5a-tetrahydro-3-thia-cyclopropa[a]pentalen-4-yl)-propan-1-one | 1.00 | 449.39 |
| 112 | 3-[3-Fluoro-4-(2-hydroxy-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one | 1.06 | 419.26 |
| 113 | 3-[3-Fluoro-4-(3-hydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one | 1.07 | 433.24 |
| 114 | 3-[3-Fluoro-4-(2-hydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one | 1.09 | 433.32 |

Examples 115 to 120

The following examples are prepared in analogy to Example 51 starting from vanilline.

| Example | Name | LC-MS | |
|---|---|---|---|
| | | $t_R$ [min] | $[M + 1]^+$ |
| 115 | 3-[4-((S)-2,3-Dihydroxy-propoxy)-3-methoxy-phenyl]-1-((1aS,5aR)-1,1,2-trimethyl-1,1a,5,5a-tetrahydro-3-thia-cyclopropa[a]pentalen-4-yl)-propan-1-one | 0.97 | 431.22 |
| 116 | 3-[4-((R)-2,3-Dihydroxy-propoxy)-3-methoxy-phenyl]-1-((1aS,5aR)-1,1,2-trimethyl-1,1a,5,5a-tetrahydro-3-thia-cyclopropa[a]pentalen-4-yl)-propan-1-one | 0.97 | 431.25 |
| 117 | 3-[4-(2-Hydroxy-ethoxy)-3-methoxy-phenyl]-1-((1aS,5aR)-1,1,2-trimethyl-1,1a,5,5a-tetrahydro-3-thia-cyclopropa[a]pentalen-4-yl)-propan-1-one | 1.04 | 401.03 |
| 118 | 3-[4-(3-Hydroxy-propoxy)-3-methoxy-phenyl]-1-((1aS,5aR)-1,1,2-trimethyl-1,1a,5,5a-tetrahydro-3-thia-cyclopropa[a]pentalen-4-yl)-propan-1-one | 1.05 | 415.21 |
| 119 | 3-[4-(2-Hydroxy-propoxy)-3-methoxy-phenyl]-1-((1aS,5aR)-1,1,2-trimethyl-1,1a,5,5a-tetrahydro-3-thia-cyclopropa[a]pentalen-4-yl)-propan-1-one | 1.06 | 415.21 |
| 120 | 3-[4-(3-Hydroxy-2-hydroxymethyl-propoxy)-3-methoxy-phenyl]-1-((1aS,5aR)-1,1,2-trimethyl-1,1a,5,5a-tetrahydro-3-thia-cyclopropa[a]pentalen-4-yl)-propan-1-one | 0.99 | 445.24 |

Examples 121 to 126

The following examples are prepared in analogy to Example 51 starting from 3,5-dimethoxy-4-hydroxybenzaldehyde.

| Example | Name | LC-MS | |
|---|---|---|---|
| | | $t_R$ [min] | $[M + 1]^+$ |
| 121 | 3-[4-((S)-2,3-Dihydroxy-propoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one | 0.99 | 461.22 |
| 122 | 3-[4-((R)-2,3-Dihydroxy-propoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one | 0.99 | 461.25 |

|  |  | LC-MS | |
|---|---|---|---|
| Example | Name | $t_R$ [min] | $[M+1]^+$ |
| 123 | 3-[4-(2-Hydroxy-ethoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.05 | 431.24 |
| 124 | 3-[4-(3-Hydroxy-propoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.05 | 445.26 |
| 125 | 3-[4-(2-Hydroxy-propoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.08 | 445.22 |
| 126 | 3-[4-(3-Hydroxy-2-hydroxymethyl-propoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.00 | 475.24 |

Examples 127 to 129

The following examples are prepared in analogy to Example 49 starting from 2,6-dimethoxy-4-hydroxybenzaldehyde.

|  |  | LC-MS | |
|---|---|---|---|
| Example | Name | $t_R$ [min] | $[M+1]^+$ |
| 127 | 3-[4-((S)-2,3-Dihydroxy-propoxy)-2,6-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.00 | 461.35 |
| 128 | 3-[4-((R)-2,3-Dihydroxy-propoxy)-2,6-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.01 | 461.39 |
| 129 | 3-[4-(2-Hydroxy-ethoxy)-2,6-dimethoxy-phenyl]-1-((1aS,5aR)-1,1,2-trimethyl-1,1a,5,5a-tetrahydro-3-thia-cyclopropa[a]pentalen-4-yl)-propan-1-one | 1.07 | 431.35 |

Examples 130 to 134

The following examples are prepared in analogy to Example 51 starting from 4-hydroxybenzaldehyde.

|  |  | LC-MS | |
|---|---|---|---|
| Example | Name | $t_R$ [min] | $[M+1]^+$ |
| 130 | 3-[4-((R)-2,3-Dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 0.99 | 401.20 |
| 131 | 3-[4-(2-Hydroxy-ethoxy)-phenyl]-1-((1aS,5aR)-1,1,2-trimethyl-1,1a,5,5a-tetrahydro-3-thia-cyclopropa[a]pentalen-4-yl)-propan-1-one | 1.05 | 371.19 |
| 132 | 3-[4-(3-Hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.08 | 385.21 |
| 133 | 3-[4-(2-Hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one | 1.08 | 385.14 |
| 134 | 3-[4-(3-Hydroxy-2-hydroxymethyl-propoxy)-phenyl]-1-((1aS,5aR)-1,1,2-trimethyl-1,1a,5,5a-tetrahydro-3-thia-cyclopropa[a]pentalen-4-yl)-propan-1-one | 1.01 | 415.24 |

Example 135

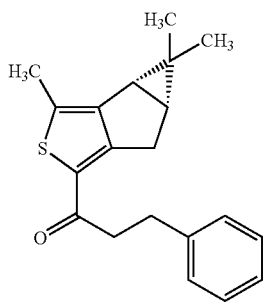

3-Phenyl-1-((1aS,5aR)-1,1,2-trimethyl-1,1a,5,5a-tetrahydro-3-thia-cyclopropa[a]-pentalen-4-yl)-propan-1-one is prepared by reacting (1aS,5aR)-1,1,2-trimethyl-1,1a,5,5a-tetrahydro-3-thia-cyclopropa[a]penta-lene-4-carboxylic acid methoxy-methyl-amide with phenethyl magnesium chloride in analogy to Example 48; LC-MS: $t_R$=1.15, $[m+1]^+$=311.00.

Example 136

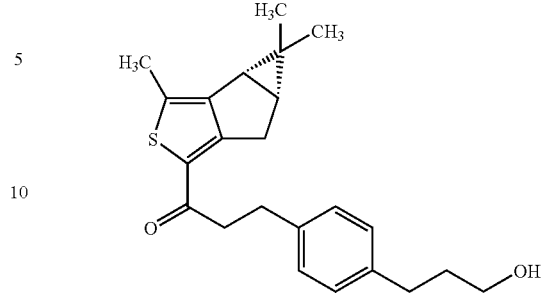

3-[4-(3-Hydroxy-propyl)-phenyl]-1-((1aS,5aR)-1,1,2-trimethyl-1,1a,5,5a-tetrahydro-3-thia-cyclopropa[a]pentalen-4-yl)-propan-1-one is prepared in analogy to Example 49 starting from 4-(3-hydroxy-propyl)-benzaldehyde; LC-MS: $t_R$=1.09, $[m+1]^+$=369.10.

Examples 137 to 140

The following examples are prepared starting in analogy to Example 51 from rac-1-((1aS,5aR)-2-ethyl-1,1-dimethyl-1,1a,5,5a-tetrahydro-3-thia-cyclopropa[a]pentalen-4-yl)-ethanone and 3,5-dimethyl-4-hydroxybenzaldehyde.

| Example | Name | LC-MS | |
|---|---|---|---|
| | | $t_R$ [min] | $[M + 1]^+$ |
| 137 | 3-[4-((S)-2,3-Dihydroxy-propoxy)-3,5-dimethyl-phenyl]-1-((1aR,5aS)-2-ethyl-1,1-dimethyl-1,1a,5,5a-tetrahydro-3-thia-cyclopropa[a]pentalen-4-yl)-propan-1-one | 1.06 | 443.31 |
| 138 | 3-[4-((R)-2,3-Dihydroxy-propoxy)-3,5-dimethyl-phenyl]-1-((1aR,5aS)-2-ethyl-1,1-dimethyl-1,1a,5,5a-tetrahydro-3-thia-cyclopropa[a]pentalen-4-yl)-propan-1-one | 1.06 | 443.38 |
| 139 | 1-((1aR,5aS)-2-Ethyl-1,1-dimethyl-1,1a,5,5a-tetrahydro-3-thia-cyclopropa[a]pentalen-4-yl)-3-[4-(3-hydroxy-propoxy)-3,5-dimethyl-phenyl]-propan-1-one | 1.14 | 427.37 |
| 140 | 1-((1aR,5aS)-2-Ethyl-1,1-dimethyl-1,1a,5,5a-tetrahydro-3-thia-cyclopropa[a]pentalen-4-yl)-3-[4-(2-hydroxy-propoxy)-3,5-dimethyl-phenyl]-propan-1-one | 1.15 | 427.30 |

Examples 141 to 149

To a solution of 2-bromo-1-((1aS,5aR)-1,1,2-trimethyl-1,1a,5,5a-tetrahydro-3-thia-cyclo-propa[a]pentalen-4-yl)-ethanone (8 mg, 27 μmol) in acetone (0.7 mL) $K_2CO_3$ (11 mg, 81 μmol) followed by the appropriate phenol (54 μmol) is added. The mixture is shaken at rt for 27 h before it is diluted with acetic acid:methanol 1:1 and separated by prep. HPLC (Waters Symmetry 19×50 mm 5 μm, 20 to 95% acetonitrile in water containing 0.5% HCOOH) to give the compounds of the Examples listed below:

| Example | Name | LC-MS | |
|---|---|---|---|
| | | $t_R$ [min] | $[M + 1]^+$ |
| 141 | 2-Phenoxy-1-((1aS,5aR)-1,1,2-trimethyl-1,1a,5,5a-tetrahydro-3-thia-cyclopropa[a]pentalen-4-yl)-ethanone | 1.11 | 313.24 |
| 142 | 2-(4-Methoxy-phenoxy)-1-((1aS,5aR)-1,1,2-trimethyl-1,1a,5,5a-tetrahydro-3-thia-cyclopropa[a]pentalen-4-yl)-ethanone | 1.10 | 343.29 |

-continued

| Example | Name | LC-MS t_R [min] | [M + 1]+ |
|---|---|---|---|
| 143 | 2-(2-Methoxy-phenoxy)-1-((1aS,5aR)-1,1,2-trimethyl-1,1a,5,5a-tetrahydro-3-thia-cyclopropa[a]pentalen-4-yl)-ethanone | 1.09 | 343.25 |
| 144 | 2-(2-Ethyl-phenoxy)-1-((1aS,5aR)-1,1,2-trimethyl-1,1a,5,5a-tetrahydro-3-thia-cyclopropa[a]pentalen-4-yl)-ethanone | 1.17 | 341.27 |
| 145 | 2-(2,3-Dimethyl-phenoxy)-1-((1aS,5aR)-1,1,2-trimethyl-1,1a,5,5a-tetrahydro-3-thia-cyclopropa[a]pentalen-4-yl)-ethanone | 1.17 | 341.20 |
| 146 | 2-(3,5-Dimethyl-phenoxy)-1-((1aS,5aR)-1,1,2-trimethyl-1,1a,5,5a-tetrahydro-3-thia-cyclopropa[a]pentalen-4-yl)-ethanone | 1.15 | 341.27 |
| 147 | 2-(3-Trifluoromethyl-phenoxy)-1-((1aS,5aR)-1,1,2-trimethyl-1,1a,5,5a-tetrahydro-3-thia-cyclopropa[a]pentalen-4-yl)-ethanone | 1.16 | 381.28 |
| 148 | 2-(4-Hydroxymethyl-2-methoxy-phenoxy)-1-((1aS,5aR)-1,1,2-trimethyl-1,1a,5,5a-tetrahydro-3-thia-cyclopropa[a]pentalen-4-yl)-ethanone | 0.99 | 373.31 |
| 149 | 2-[4-(2-Hydroxy-ethyl)-phenoxy]-1-((1aS,5aR)-1,1,2-trimethyl-1,1a,5,5a-tetrahydro-3-thia-cyclopropa[a]pentalen-4-yl)-ethanone | 1.02 | 357.27 |

Example 143

$^1$H NMR (CDCl$_3$): δ 7.00-6.84 (m, 4H), 4.98 (s, 2H), 3.88 (s, 3H), 3.03 (dd, J 0 5.3, 18.8 Hz, 1H), 2.84 (d, J=19.3 Hz, 1H), 2.40 (s, 3H), 1.94-1.88 (m, 2H), 1.12 (s, 3H), 0.72 (s, 3H).

Examples 150 to 163

To solution of 2-bromo-1-((1aS,5aR)-1,1,2-trimethyl-1,1a,5,5a-tetrahydro-3-thia-cyclo-propa[a]pentalen-4-yl)-ethanone (8 mg, 27 µmol) in acetone (0.7 mL) K$_2$CO$_3$ (11 mg, 81 µmol) followed by the appropriate aniline (54 µmol) is added. The mixture is shaken at rt for 27 h before it is diluted with acetic acid:methanol 1:1 and separated by prep. HPLC (Waters Symmetry 19×50 mm 5 µm, 20 to 95% acetonitrile in water containing 0.5% HCOOH) to give the compounds of the Examples listed below:

| Example | Name | LC-MS t_R [min] | [M + 1]+ |
|---|---|---|---|
| 150 | 2-Phenylamino-1-((1aS,5aR)-1,1,2-trimethyl-1,1a,5,5a-tetrahydro-3-thia-cyclopropa[a]pentalen-4-yl)-ethanone | 1.11 | 312.26 |
| 151 | 2-(2-Methoxy-phenylamino)-1-((1aS,5aR)-1,1,2-trimethyl-1,1a,5,5a-tetrahydro-3-thia-cyclopropa[a]pentalen-4-yl)-ethanone | 1.13 | 342.29 |
| 152 | 2-o-Tolylamino-1-((1aS,5aR)-1,1,2-trimethyl-1,1a,5,5a-tetrahydro-3-thia-cyclopropa[a]pentalen-4-yl)-ethanone | 1.15 | 326.29 |
| 153 | 2-(2-Ethyl-phenylamino)-1-((1aS,5aR)-1,1,2-trimethyl-1,1a,5,5a-tetrahydro-3-thia-cyclopropa[a]pentalen-4-yl)-ethanone | 1.17 | 240.19 |
| 154 | 2-(4-Methoxy-phenylamino)-1-((1aS,5aR)-1,1,2-trimethyl-1,1a,5,5a-tetrahydro-3-thia-cyclopropa[a]pentalen-4-yl)-ethanone | 1.01 | 342.35 |
| 155 | 2-(2,4-Dimethoxy-phenylamino)-1-((1aS,5aR)-1,1,2-trimethyl-1,1a,5,5a-tetrahydro-3-thia-cyclopropa[a]pentalen-4-yl)-ethanone | 1.05 | 372.22 |
| 156 | 2-(4-Methoxy-2-methyl-phenylamino)-1-((1aS,5aR)-1,1,2-trimethyl-1,1a,5,5a-tetrahydro-3-thia-cyclopropa[a]pentalen-4-yl)-ethanone | 1.10 | 356.34 |

-continued

| Example | Name | LC-MS $t_R$ [min] | $[M + 1]^+$ |
|---|---|---|---|
| 157 | 2-(3,5-Dimethyl-phenylamino)-1-((1aS,5aR)-1,1,2-trimethyl-1,1a,5,5a-tetrahydro-3-thia-cyclopropa[a]pentalen-4-yl)-ethanone | 1.14 | 340.32 |
| 158 | 2-(3-Trifluoromethyl-phenylamino)-1-((1aS,5aR)-1,1,2-trimethyl-1,1a,5,5a-tetrahydro-3-thia-cyclopropa[a]pentalen-4-yl)-ethanone | 1.17 | 421.27 |
| 159 | 2-(2-Methoxy-5-trifluoromethyl-phenylamino)-1-((1aS,5aR)-1,1,2-trimethyl-1,1a,5,5a-tetrahydro-3-thia-cyclopropa[a]pentalen-4-yl)-ethanone | 1.19 | 410.16 |
| 160 | 2-(3-Methoxy-5-trifluoromethyl-phenylamino)-1-((1aS,5aR)-1,1,2-trimethyl-1,1a,5,5a-tetrahydro-3-thia-cyclopropa[a]pentalen-4-yl)-ethanone | 1.17 | 410.22 |
| 161 | 2-(4-Methoxy-3-trifluoromethyl-phenylamino)-1-((1aS,5aR)-1,1,2-trimethyl-1,1a,5,5a-tetrahydro-3-thia-cyclopropa[a]pentalen-4-yl)-ethanone | 1.15 | 410.25 |
| 162 | 2-(2-Methyl-5-trifluoromethyl-phenylamino)-1-((1aS,5aR)-1,1,2-trimethyl-1,1a,5,5a-tetrahydro-3-thia-cyclopropa[a]pentalen-4-yl)-ethanone | 1.19 | 394.24 |
| 163 | 2-[4-(2-Hydroxy-ethyl)-phenylamino]-1-((1aS,5aR)-1,1,2-trimethyl-1,1a,5,5a-tetrahydro-3-thia-cyclopropa[a]pentalen-4-yl)-ethanone | 1.00 | 356.26 |

Example 157

$^1$H NMR (CDCl$_3$): δ 6.40 (s, 1H), 6.29 (s, 1H), 4.25 (s, 2H), 3.06 (dd, J=6.4, 18.8 Hz, 1H), 2.86 (d, J=18.8 Hz, 1H), 2.41 (s, 3H), 2.26 (s, 6H), 2.00-1.91 (m, 2H), 1.14 (s, 3H), 0.74 (s, 3H).

Example 164

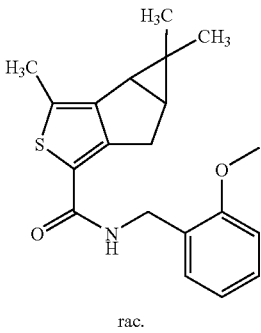

rac.

rac-(1aS,5aR)-1,1,2-Trimethyl-1,1a,5,5a-tetrahydro-3-thia-cyclopropa[a]pentalene-4-carboxylic acid 2-methoxy-benzylamide is prepared in analogy to Example 1 starting from rac-(1S*,5R*)-2-[1-chloro-eth-(E)-ylidene]-6,6-dimethyl-bicyclo[3.1.0]hexan-3-one. LC-MS: $t_R$=1.07 min, [M+1]$^+$=342.32.

Example 165

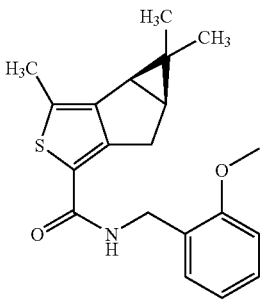

(1aR,5aS)-1,1,2-Trimethyl-1,1a,5,5a-tetrahydro-3-thia-cyclopropa[a]pentalene-4-carboxylic acid 2-methoxy-benzylamide is obtained by chiral resolution on HPLC (Chiralcel OD 4.6×250 mm, 10 μm, eluting with 10% ethanol in hexane (0.8 mL/min)) of the corresponding racemate; HPLC: $t_R$=13.0 min (Chiralcel with above conditions); ((1aS,5aR)-isomer: $t_R$=9.6 min).

Example 166

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH was 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at room temperature. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order# 6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Table 1 shows the $EC_{50}$ value of some Examples determined as described above:

TABLE 1

| Compound of Example | $EC_{50}$ [nM] |
|---|---|
| 5 | 75 |
| 7 | 183 |
| 24 | 164 |
| 36 | 300 |
| 48 | 16 |
| 49 | 2 |
| 51 | 0.3 |
| 53 | 3 |
| 63 | 5 |
| 71 | 1 |
| 74 | 5 |
| 81 | 3 |
| 137 | 0.6 |
| 139 | 4 |
| 157 | 9 |
| 163 | 3 |

Example 167

Assessment of in Vivo Efficacy

The efficacy of the compounds of Formula (I) is assessed by measuring the circulating lymphocytes after oral administration of 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3 and/or 6 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 3 h after oral administration of 30 mg/kg of two compounds of the present invention to normotensive male Wistar rats as compared to a group of animals treated with vehicle only.

TABLE 2

| Compound of Example | Lymphocyte counts |
|---|---|
| 7 | −46 ± 3% |
| 24 | −40 ± 4% |
| 51 | −44 ± 4% |
| 56 | −58 ± 5% |
| 75 | −57 ± 5% |
| 86 | −47 ± 4% |

The invention claimed is:

1. A compound of Formula (I)

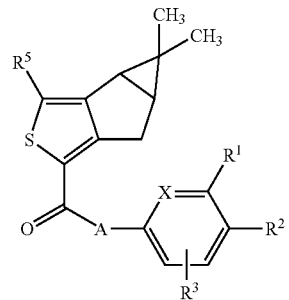

Formula (I)

wherein
A represents —$CH_2CH_2$—, —CH=CH—, —$CH_2$—O—, or —$CH_2NH$—;
$R^1$ represents hydrogen, alkyl or halogen; and in the case A represents —$CH_2$—$CH_2$— or —$CH_2NH$—, $R^1$ in addition represents alkoxy;
$R^2$ represents hydrogen, alkoxy, fluoro-alkoxy, hydroxy-alkoxy, hydroxy-alkyl, di-(hydroxy-alkyl)-alkyl, di-(hydroxy-alkyl)-alkoxy, 1-glyceryl or 2-glyceryl;
$R^3$ represents hydrogen, alkyl, mono- or di-alkylamino, trifluoromethyl, trifluoromethoxy or halogen; and in the case A represents —$CH_2$—$CH_2$— or —$CH_2NH$—, $R^3$ in addition represents alkoxy;
X represents C—$R^4$;
$R^4$ represents hydrogen, alkyl, alkoxy, or halogen; and
$R^5$ represents methyl or ethyl;
in free or an optically pure enantiomer, a mixture of enantiomers, a racemate, a diastereomer, a mixture of diastereomers, a diastereomeric racemate, a mixture of diastereomeric racemates, or a salt form.

2. A compound according to claim 1, wherein
A represents —$CH_2CH_2$—, —CH=CH—, or —NH—$CH_2$—;
$R^1$ represents hydrogen, alkyl or halogen;
$R^3$ represents hydrogen, alkyl, mono- or di-alkylamino, trifluoromethyl, trifluoromethoxy or halogen; and
$R^3$ represents methyl.

3. A compound according to claim 1 or 2, wherein A represents —CH=CH—.

4. A compound according to claim 1 or 2, wherein A represents —NH—$CH_2$—.

5. A compound according to claim 1 or 2, wherein A represents —$CH_2CH_2$—.

6. A compound according to claim 1 or 2, wherein A represents —$CH_2NH$—.

7. A compound according to claim 1 or 2, wherein $R^4$ represents a methoxy group, and $R^1$ represents hydrogen.

8. A compound according to claim 1 or 2, wherein $R^4$ represents a methoxy group, and $R^1$ and $R^3$ both represent hydrogen.

9. A compound according to claim 1 or 2, wherein $R^2$ represents hydroxy-alkoxy, hydroxy-alkyl, di-(hydroxy-alkyl)-alkoxy, di-(hydroxy-alkyl)-alkyl, 1-glyceryl, or 2-glyceryl.

10. A compound according to claim 9, wherein $R^2$ represents an (S)-1-glyceryl group.

11. A compound according to claim 1 or 2, wherein $R^4$ represents hydrogen, $R^1$ and $R^3$ both represent a methyl group, and R² represents hydroxy-alkoxy, hydroxy-alkyl, di-(hydroxy-alkyl)-alkoxy, di-(hydroxy-alkyl)-alkyl, 1-glyceryl, or 2-glyceryl.

12. A compound of Formula (II)

Formula (II)

according to claim 1 or 2.

13. A compound of Formula (III)

Formula (III)

according to claim 1 or 2.

14. A compound according to claim 1 selected from the group consisting of:

- (1aS,5aR)-1,1,2-Trimethyl-1,1a,5,5a-tetrahydro-3-thia-cyclopropa[a]pentalene-4-carboxylic acid 2-methoxy-benzylamide,
- (1aS,5aR)-1,1,2-trimethyl-1,1a,5,5a-tetrahydro-3-thia-cyclopropa[a]pentalene-4-carboxylic acid 2,4-dimethoxy-benzylamide,
- (1aS,5aR)-1,1,2-trimethyl-1,1a,5,5a-tetrahydro-3-thia-cyclopropa[a]pentalene-4-carboxylic acid 4-ethoxy-2-methoxy-benzylamide,
- (1aS,5aR)-1,1,2-trimethyl-1,1a,5,5a-tetrahydro-3-thia-cyclopropa[a]pentalene-4-carboxylic acid 2-methyl-benzylamide,
- (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3,5-dimethyl-benzylamide,
- (1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3,5-dimethyl-benzylamide,
- (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-2-methoxy-benzylamide,
- (1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-2-methoxy-benzylamide,
- (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3-methyl-benzylamide,
- (1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3-methyl-benzylamide,
- (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-3-chloro-benzylamide,
- (1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-3-chloro-benzylamide,
- (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-2-chloro-benzylamide,
- (1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-2-chloro-benzylamide,
- (1aS,5aR)-1,1,2-trimethyl-1,1a,5,5a-tetrahydro-3-thia-cyclopropa[a]pentalene-4-carboxylic acid 4-((S)-2,3-dihydroxy-propoxy)-benzylamide,
- (1aS,5aR)-1,1,2-trimethyl-1,1a,5,5a-tetrahydro-3-thia-cyclopropa[a]pentalene-4-carboxylic acid 4-((R)-2,3-dihydroxy-propoxy)-benzylamide,
- (1aS,5aR)-1,1,2-trimethyl-1,1a,5,5a-tetrahydro-3-thia-cyclopropa[a]pentalene-4-carboxylic acid 4-(2-hydroxy-ethoxy)-3,5-dimethyl-benzylamide,
- (1aS,5aR)-1,1,2-trimethyl-1,1a,5,5a-tetrahydro-3-thia-cyclopropa[a]pentalene-4-carboxylic acid 4-(2-hydroxy-ethoxy)-2-methoxy-benzylamide,
- (1aS,5aR)-1,1,2-trimethyl-1,1a,5,5a-tetrahydro-3-thia-cyclopropa[a]pentalene-4-carboxylic acid 4-(2-hydroxy-ethoxy)-3-methyl-benzylamide,
- (1aS,5aR)-1,1,2-trimethyl-1,1a,5,5a-tetrahydro-3-thia-cyclopropa[a]pentalene-4-carboxylic acid 4-(2-hydroxy-ethoxy)-3-chloro-benzylamide,
- (1aS,5aR)-1,1,2-trimethyl-1,1a,5,5a-tetrahydro-3-thia-cyclopropa[a]pentalene-4-carboxylic acid 4-(2-hydroxy-ethoxy)-2-chloro-benzylamide,
- (1aS,5aR)-1,1,2-trimethyl-1,1a,5,5a-tetrahydro-3-thia-cyclopropa[a]pentalene-4-carboxylic acid 4-(2-hydroxy-ethoxy)-benzylamide,
- (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-3,5-dimethyl-benzylamide,
- (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-2-methoxy-benzylamide,
- (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-3-methyl-benzylamide,
- (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-3-chloro-benzylamide,
- (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-2-chloro-benzylamide,
- (1aS,5aR)-1,1,2-trimethyl-1,1a,5,5a-tetrahydro-3-thia-cyclopropa[a]pentalene-4-carboxylic acid 4-((R/S)-2-hydroxy-propoxy)-benzylamide,
- (1aS,5aR)-1,1,2-trimethyl-1,1a,5,5a-tetrahydro-3-thia-cyclopropa[a]pentalene-4-carboxylic acid 4-(3-hydroxy-propoxy)-3,5-dimethyl-benzylamide,
- (1aS,5aR)-1,1,2-trimethyl-1,1a,5,5a-tetrahydro-3-thia-cyclopropa[a]pentalene-4-carboxylic acid 4-(3-hydroxy-propoxy)-2-methoxy-benzylamide,
- (1aS,5aR)-1,1,2-trimethyl-1,1a,5,5a-tetrahydro-3-thia-cyclopropa[a]pentalene-4-carboxylic acid 4-(3-hydroxy-propoxy)-3-methyl-benzylamide, (1aS,5aR)-1,1,2-trimethyl-1,1a,5,5a-tetrahydro-3-thia-cyclopropa[a]pentalene-4-carboxylic acid 4-(3-hydroxy-propoxy)-3-chloro-benzylamide, (1aS,5aR)-1,1,2-trimethyl-1,1a,5,5a-tetrahydro-3-thia-cyclopropa[a]pentalene-4-carboxylic acid 4-(3-hydroxy-propoxy)-2-chloro-benzylamide, (1aS,5aR)-1,1,2-trimethyl-1,1a,5,5a-tetrahydro-3-thia-cyclopropa[a]pentalene-4-carboxylic acid 4-(3-hydroxy-propoxy)-benzylamide, (1aS,5aR)-1,1,2-trimethyl-1,1a,5,5a-tetrahydro-3-thia-cyclopropa[a]pentalene-4-carboxylic acid 4-(2-fluoro-ethoxy)-3,5-dimethyl-benzylamide, (1aS,5aR)-1,1,2-trimethyl-1,1a,5,5a-tetrahydro-3-thia-cyclopropa[a]pentalene-4-carboxylic acid 4-(2-fluoro-ethoxy)-2-methoxy-benzylamide, (1aS,5aR)-1,1,2-trimethyl-1,1a,5,5a-tetrahydro-3-thia-cyclopropa[a]pentalene-4-carboxylic acid 2-chloro-4-(2-fluoro-ethoxy)-benzylamide, (1aS,5aR)-1,1,2-trimethyl-1,1a,5,5a-tetrahydro-3-thia-cyclopropa[a]pentalene-4-carboxylic acid 4-(2-fluoro-ethoxy)-benzylamide, (1aS,5aR)-1,1,2-trimethyl-1,1a,5,5a-tetrahydro-3-thia-cyclopropa[a]pentalene-4-carboxylic acid 4-(3-fluoro-propoxy)-2-methoxy-benzylamide, (1aS,5aR)-1,1,2-trimethyl-1,1a,5,5a-tetrahydro-3-thia-cyclopropa[a]pentalene-4-carboxylic acid 2-methoxy-4-propoxy-benzylamide, (1aS,5aR)-1,1,2-trimethyl-1,1a,5,5a-tetrahydro-3-thia-cyclopropa[a]pentalene-4-carboxylic acid 2-methoxy-4-isopropoxy-benzylamide, (1aS,5aR)-1,1,2-trimethyl-1,1a,5,5a-tetrahydro-3-thia-cyclopropa[a]pentalene-4-carboxylic acid 4-isobutoxy-2-methoxy-benzylamide, (1aS,5aR)-1,1,2-trimethyl-1,1a,5,5a-tetrahydro-3-thia-cyclopropa[a]pentalene-4-carboxylic acid 4-(6-hydroxy-hexyloxy)-2-methoxy-benzylamide, (1aS,5aR)-1,1,2-trimethyl-1,1a,5,5a-tetrahydro-3-thia-cyclopropa[a]pentalene-4-carboxylic acid 4-(3-hydroxy-2-hydroxymethyl-propoxy)-3,5-dimethyl-benzylamide, 3-(2-methoxy-phenyl)-1-((1aS,5aR)-1,1,2-trimethyl-1,1a,5,5a-tetrahydro-3-thia-cyclopropa[a]penta-len-4-yl)-propan-1-one, 3-[4-((S)-2,3-dihydroxy-propoxy)-2-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-(2-hydroxy-ethoxy)-2-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-[4-((R)-2,3-dihydroxy-propoxy)-3,5-dimethyl-phenyl]-1-((1aS,5aR)-1,1,2-trimethyl-1,1a,5,5a-tetrahydro-3-thia-cyclopropa[a]pentalen-4'-yl)-propan-1-one, 3-[4-(2-hydroxy-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-[4-(2-(R/S)-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-[4-(2-(2-fluoroethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, and 3-[4-(3-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one.

15. A compound according to claim 1 selected from the group consisting of:

3-[4-(3-Hydroxy-2-hydroxymethyl-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3-ethyl-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[4-((R)-2,3-dihydroxy-propoxy)-3-ethyl-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-ethyl-4-(2-hydroxy-ethoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3,5-diethyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((S)-2,3-dihydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((R)-2,3-dihydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-(2-hydroxy-ethoxy)-5-methyl-phenyl]-1-(1aS,5aR)-1,1,2-trimethyl-1,1a,5,5a-tetrahydro-3-thia-cyclopropa[a]pentalen-4-yl)-propan-1-one, 3-[3-chloro-4-(2-hydroxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4'-yl)-propan-1-one, 3-[2-chloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-(2-hydroxy-ethoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-(3-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[2-chloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3-methyl-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-2,3,5-trimethyl-phenyl]-1-((1aS,5aR)-1,1,2-trimethyl-1,1a,5,5a-tetrahydro-3-thia-cyclopropa[a]pentalen-4-yl)-propan-1-one, 3-[3,5-dichloro-4-((S)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[3,5-dichloro-4-((R)-2,3-dihydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[3,5-dichloro-4-(2-hydroxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((S)-2,3-dihydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-((R)-2,3-dihydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-(2-hydroxy-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3-fluoro-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-((R)-2,3-dihydroxy-propoxy)-3-fluoro-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[3-fluoro-4-(2-hydroxy-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-[4-(3-hydroxy-propyl)-phenyl]-1-((1aS,5aR)-1,1,2-trimethyl-1,1a,5,5a-tetrahydro-3-thia-cyclopropa[a]pentalen-4-yl)-propan-1-one, 3-[4-((S)-2,3-dihydroxy-propoxy)-3,5-dimethyl-phenyl]-1-((1aR,5aS)-2-ethyl-1,1-dimethyl-1,1a,5,5a-tetrahydro-3-thia-cyclopropa[a]pentalen-4-yl)-propan-1-one, 3-[4-((R)-2,3-dihydroxy-propoxy)-3,5-dimethyl-phenyl]-1-((1aR,5aS)-2-ethyl-1,1-dimethyl-1,1a,5,5a-tetrahydro-3-thia-cyclopropa[a]pentalen-4-yl)-propan-1-one, 1-((1aR,5aS)-2-ethyl-1,1-dimethyl-1,1a,5,5a-tetrahydro-3-thia-cyclopropa[a]pentalen-4-yl)-3-[4-(3-hydroxy-propoxy)-3,5-dimethyl-phenyl]-propan-1-one, 1-((1aR,5aS)-2-ethyl-1,1-dimethyl-1,1a,5,5a-tetrahydro-3-thia-cyclopropa[a]pentalen-4-yl)-3-[4-(2-hydroxy-propoxy)-3,5-dimethyl-phenyl]-propan-1-one, 2-(2-methoxy-phenylamino)-1-((1aS,5aR)-1,1,2-trimethyl-1,1a,5,5a-tetrahydro-3-thia-cyclopropa[a]pentalen-4-yl)-ethanone, 2-(3,5-dimethyl-phenylamino)-1-((1aS,5aR)-1,1,2-trimethyl-1,1a,5,5a-tetrahydro-3-thia-cyclopropa[a]pentalen-4-yl)-ethanone, and 2-[4-(2-hydroxy-ethyl)-phenylamino]-1-((1aS,5aR)-1,1,2-trimethyl-1,1a,5,5a-tetrahydro-3-thia-cyclopropa[a]pentalen-4-yl)-ethanone.

16. A pharmaceutical composition comprising a compound according to claim 1 and a pharmaceutically acceptable carrier material.

* * * * *

UNITED STATES PATENT AND TRADEMARK OFFICE
CERTIFICATE OF CORRECTION

PATENT NO.         : 7,750,040 B2
APPLICATION NO.    : 11/572801
DATED              : July 6, 2010
INVENTOR(S)        : Bolli et al.

It is certified that error appears in the above-identified patent and that said Letters Patent is hereby corrected as shown below:

On the Title Page, Item (73), left hand column, below the list of inventors should read:
"Assignee: Actelion Pharmaceuticals LTD., Gewerbestrasse 16, Allschwil, Switzerland Ch-4123"

Signed and Sealed this
Fifteenth Day of October, 2013

Teresa Stanek Rea
*Deputy Director of the United States Patent and Trademark Office*